US007611904B2

(12) United States Patent
Afar et al.

(10) Patent No.: US 7,611,904 B2
(45) Date of Patent: Nov. 3, 2009

(54) SERPENTINE TRANSMEMBRANE ANTIGENS EXPRESSED IN HUMAN CANCERS AND USES THEREOF

(75) Inventors: Daniel E. Afar, Pacific Palisades, CA (US); Rene S. Hubert, Los Angeles, CA (US); Kahan Leong, Playa Del Rey, CA (US); Arthur B. Raitano, Los Angeles, CA (US); Douglas C. Saffran, Los Angeles, CA (US); Stephen Chappell Mitchell, Santa Monica, CA (US)

(73) Assignee: Agensys, Inc., Santa Monica, CA (US)

( * ) Notice: Subject to any disclaimer, the term of this patent is extended or adjusted under 35 U.S.C. 154(b) by 0 days.

(21) Appl. No.: 11/580,538

(22) Filed: Oct. 12, 2006

(65) Prior Publication Data

US 2007/0104720 A1    May 10, 2007

Related U.S. Application Data

(60) Continuation of application No. 10/750,262, filed on Dec. 31, 2003, now Pat. No. 7,166,714, which is a division of application No. 10/011,095, filed on Dec. 6, 2001, now Pat. No. 7,053,186, which is a division of application No. 09/323,873, filed on Jun. 1, 1999, now Pat. No. 6,329,503.

(60) Provisional application No. 60/091,183, filed on Jun. 30, 1998, provisional application No. 60/087,520, filed on Jun. 1, 1998, provisional application No. 60/317,840, filed on Sep. 6, 2001, provisional application No. 60/370,387, filed on Apr. 5, 2002.

(51) Int. Cl.
*G01N 33/53* (2006.01)

(52) U.S. Cl. .................... 436/501; 436/518; 435/7.1; 435/7.23

(58) Field of Classification Search .................. None
See application file for complete search history.

(56) References Cited

U.S. PATENT DOCUMENTS

| | | | |
|---|---|---|---|
| 5,416,064 A | 5/1995 | Chari et al. | 514/229.5 |
| 5,859,045 A | 1/1999 | Treppendahl et al. | 424/130.1 |
| 6,048,970 A | 4/2000 | Lal et al. | 536/23.6 |
| 6,329,503 B1 | 12/2001 | Afar et al. | 530/350 |
| 6,342,219 B1 | 1/2002 | Thorpe et al. | 424/145.1 |
| 6,887,975 B2 | 5/2005 | Afar et al. | 530/300 |
| 7,053,186 B2 | 5/2006 | Afar et al. | 530/387.7 |
| 7,166,714 B2 | 1/2007 | Afar et al. | 536/23.1 |
| 2002/0022248 A1 | 2/2002 | Xu et al. | 435/69.1 |
| 2003/0045682 A1 | 3/2003 | Afar et al. | |
| 2003/0060612 A1 | 3/2003 | Goddard et al. | 536/32.1 |
| 2003/0064397 A1 | 4/2003 | Spancake et al. | 435/6 |

FOREIGN PATENT DOCUMENTS

| | | |
|---|---|---|
| EP | 0834563 | 4/1998 |
| WO | WO 94/09150 | 4/1994 |
| WO | WO 98/18489 | 5/1998 |
| WO | WO 98/37093 | 8/1998 |
| WO | WO 98/37418 | 8/1998 |
| WO | WO 98/53071 | 11/1998 |
| WO | WO 99/06548 | 2/1999 |
| WO | WO 99/06550 | 2/1999 |
| WO | WO 99/61469 | 2/1999 |
| WO | WO 99/62941 | 12/1999 |
| WO | WO 00/04149 | 1/2000 |
| WO | WO 00/35937 | 6/2000 |
| WO | WO 01/12662 | 2/2001 |
| WO | WO 01/72962 | 10/2001 |
| WO | WO 02/16429 | 2/2002 |
| WO | WO 02/26822 | 4/2002 |
| WO | WO 2005/113601 A2 | 12/2005 |
| WO | WO 03/022995 | 3/2006 |
| WO | WO 2006/034488 A2 | 3/2006 |

OTHER PUBLICATIONS

Challita-Eid Pia M., et al., "Monoclonal antibodies to six-transmembrane epithelial antigen of the prostate-1 inhibit intercellular communication in vitro and growth of human tumor xenografts in vivo", vol. 67, No. 12, pp. 5798-5805, (2007).
Faris M., et al., "Validation of STEAP-1 as a cell surface cancer therapeutic target", Proceedings of the annual meeting of the American Association for Cancer Research, vol. 43, p. 947, (2002).
Abu-Threideh et al., Jun. 1998, EMBL/GENBAK/DDBJ Databases.
Abu-Threideh et al., GENBANK (Accession No. 095034) National Library of Medicine, Bethesda MD, May 1, 1999.
Alberts et al., Molecular Biology of the Cell, 3$^{rd}$ edition (1994) p. 465.
Bellone et al., Immunolgoy Today (1999) 20(10):457-462.
Bowie et al, Science 247:1306-1310 (1990).
Burgess et al., J. Cell Biol. 111:2129-2138 (1990).
Cate et al., GENBANK (Accession No. W86309) National Library of Medicine, Bethesda MD, Nov. 1998.

(Continued)

*Primary Examiner*—Misook Yu
(74) *Attorney, Agent, or Firm*—Atulya Agarwal; Shane M. Popp, J.D., L.L.M.; Ginger R. Dreger

(57) ABSTRACT

Described is a novel family of cell surface serpentine transmembrane antigens. Two of the proteins in this family are exclusively or predominantly expressed in the prostate, as well as in prostate cancer, and thus members of this family have been termed "STEAP" (SIX Transmembrane Epithelial Antigens of the Prostate). Four particular human STEAPs are described and characterized herein. The human STEAPs exhibit a high degree of structural conservation among them but show no significant structural homology to any known human proteins. The prototype member of the STEAP family, STEAP-1, appears to be a type IIIa membrane protein expressed predominantly in prostate cells in normal human tissues. Structurally, STEAP-1 is a 339 amino acid protein characterized by a molecular topology of six transmembrane domains and intracellular N- and C-termini, suggesting that it folds in a "serpentine" manner into three extracellular and two intracellular loops. STEAP-1 protein expression is maintained at high levels across various stages of prostate cancer. Moreover, STEAP-1 is highly over-expressed in certain other human cancers.

39 Claims, 26 Drawing Sheets

OTHER PUBLICATIONS

Database EMBL Nucleotide and Protein Sequences, Aug. 25, 1996, XP002128081, AA032221, Hinxton, GB.
Database EMBL Nucleotide and Protein Sequences, May 13, 1997, XP002128082, AC002064, Hinxton, GB.
Database EMBL Nucleotide and Protein Sequences, Jun. 15, 1998, XP002128084, AC004969 (clone DJ112E10), Hinxton, GB.
Database EMBL, "Human BAC Clone CTB-167B5 form 7q21, complete sequence,", Jun. 17, 1998, XP002173859, AC003991, R. Waterston et al.
Database EMBL Nucleotide and Protein Sequences, May 1, 1999, XP002128083, O95034 (clone RG041D11), Hinxton, GB.
Diss et al., "Expression of skeletal muscle-type voltage-gated Na+ channel in rat and human prostate cancer cell lines," FEBS Letters 427:5-10 (1998).
Dulcert et al., GENBANK (Accession No. Y11840), National Library of Medicine, Bethesda MD, Feb. 11, 1999.
Fu et al., EMBO Journal 15:4392-4401 (1996).
Greenspan et al, Nature Biotechnology 7:936-937 (1999).
Grimes et al., "Electrophysiological characterization of voltage-gated NA+ current expressed in the highly metastatic Mat-LyLu cell line of rat prostate cancer," Journal of Cellular Physiology 175:50-58 (1998).
Gutierrrez et al., "Activation of a $Ca^{2+}$-permeable cation channel by two different inducers of apoptosis in a human prostatic cancer cell line," Journal of Physiology 517:95-107 (1999).
Gura, Science 278:1041-1042 (1997).
Haverstick et al., "Inhibition of human prostate cancer proliferation in vitro and in a mouse model by a compound synthesized to block $Ca^{2+}$ entry," Cancer Research pp. 1002-1008 (2000).
Herbert et al., The Dictionary of Immunology, Academic Press, $4^{th}$ edition (1995).
Hubert et al., PNAS USA 96(25):14523-14528 (1999).
Lazar et al., Mol Cell. Biol. 8(3):1247-1252 (1988).
Lepple-Weinhues et al., "K+ channels and the intracellular calcium signal in human melanoma cell proliferation," J. Membrane Biol. 151:149-157 (1996).
Marino et al., "Association between cell membrane potential and breast cancer," Tumor Biol. 15:82-89 (1994).
McClean et al., Eur. J. of Cancer 29A:2243-2248 (1993).
Nie et al., "Inhibition of proliferation of MCF-7 breast cancer cells by a blocker of $Ca^{2+}$-permeable channel," Celll Calcium 22(2):75-82 (1997).
Pancrazio et al., "Voltage-dependent ion channels in small-cell lung cancer cells," Cancer Research 49:5901-5906 (1989).
Reiger et al., Glossary of Genetics and Cytogenetics, Springer-Verlag (1976), p. 17.
Shantz et al., Int. J. Biochem. Cell Bio. 31:107-122 (1999).
Skryma et al., "Potassium conductance in the androgen-sensitive prostate cancer cell line, LNCaP: involvement in cell proliferation," The Prostate 33:112-122 (1997).
Spitler, Cancer Biotherapy 10:1-3 (1995).

FIG. 1A-1

```
             11            20            29            38            47            56
GAG ACT CAC GGT CAA GCT AAG GCG AAG AGT GGG TGG CTG AAG CCA TAC TAT TTT
--- --- --- --- --- --- --- --- --- --- --- --- --- --- --- --- --- ---

65            74            83            92           101           110
ATA GAA TTA ATG GAA AGC AGA AAA GAC ATC ACA AAC CAA GAA GAA CTT TGG AAA
--- --- --- --- --- --- --- --- --- --- --- --- --- --- --- --- --- ---
             M   E   S   R   K   D   I   T   N   Q   E   E   L   W   K 119           128           137           146           155           164
ATG AAG CCT AGG AGA AAT TTA GAA GAA GAC GAT TAT TTG CAT AAG GAC ACG GGA
--- --- --- --- --- --- --- --- --- --- --- --- --- --- --- --- --- ---
 M   K   P   R   R   N   L   E   E   D   D   Y   L   H   K   D   T   G 173           182           191           200           209           218
GAG ACC AGC ATG CTA AAA AGA CCT GTG CTT TTG CAT TTG CAC CAA ACA GCC CAT
--- --- --- --- --- --- --- --- --- --- --- --- --- --- --- --- --- ---
 E   T   S   M   L   K   R   P   V   L   L   H   L   H   Q   T   A   H 227           236           245           254           263           272
GCT GAT GAA TTT GAC TGC CCT TCA GAA CTT CAG CAC ACA CAG GAA CTC TTT CCA
--- --- --- --- --- --- --- --- --- --- --- --- --- --- --- --- --- ---
 A   D   E   F   D   C   P   S   E   L   Q   H   T   Q   E   L   F   P 281           290           299           308           317           326
CAG TGG CAC TTG CCA ATT AAA ATA GCT GCT ATT ATA GCA TCT CTG ACT TTT CTT
--- --- --- --- --- --- --- --- --- --- --- --- --- --- --- --- --- ---
 Q   W   H   L   P   I   K   I   A   A   I   I   A   S   L   T   F   L 335           344           353           362           371           380
TAC ACT CTT CTG AGG GAA GTA ATT CAC CCT TTA GCA ACT TCC CAT CAA CAA TAT
--- --- --- --- --- --- --- --- --- --- --- --- --- --- --- --- --- ---
 Y   T   L   L   R   E   V   I   H   P   L   A   T   S   H   Q   Q   Y 389           398           407           416           425           434
TTT TAT AAA ATT CCA ATC CTG GTC ATC AAC AAA GTC TTG CCA ATG GTT TCC ATC
--- --- --- --- --- --- --- --- --- --- --- --- --- --- --- --- --- ---
 F   Y   K   I   P   I   L   V   I   N   K   V   L   P   M   V   S   I 443           452           461           470           479           488
ACT CTC TTG GCA TTG GTT TAC CTG CCA GGT GTG ATA GCA GCA ATT GTC CAA CTT
--- --- --- --- --- --- --- --- --- --- --- --- --- --- --- --- --- ---
 T   L   L   A   L   V   Y   L   P   G   V   I   A   A   I   V   Q   L 497           506           515           524           533           542
CAT AAT GGA ACC AAG TAT AAG AAG TTT CCA CAT TGG TTG GAT AAG TGG ATG TTA
--- --- --- --- --- --- --- --- --- --- --- --- --- --- --- --- --- ---
 H   N   G   T   K   Y   K   K   F   P   H   W   L   D   K   W   M   L 551           560           569           578           587           596
ACA AGA AAG CAG TTT GGG CTT CTC AGT TTC TTT TTT GCT GTA CTG CAT GCA ATT
--- --- --- --- --- --- --- --- --- --- --- --- --- --- --- --- --- ---
 T   R   K   Q   F   G   L   L   S   F   F   F   A   V   L   H   A   I
```

FIG. 1A-2

```
        605             614             623             632             641             650
TAT AGT CTG TCT TAC CCA ATG AGG CGA TCC TAC AGA TAC AAG TTG CTA AAC TGG
--- --- --- --- --- --- --- --- --- --- --- --- --- --- --- --- --- ---
 Y   S   L   S   Y   P   M   R   R   S   Y   R   Y   K   L   L   N   W 659             668             677             686             695             704
GCA TAT CAA CAG GTC CAA CAA AAT AAA GAA GAT GCC TGG ATT GAG CAT GAT GTT
--- --- --- --- --- --- --- --- --- --- --- --- --- --- --- --- --- ---
 A   Y   Q   Q   V   Q   Q   N   K   E   D   A   W   I   E   H   D   V 713             722             731             740             749             758
TGG AGA ATG GAG ATT TAT GTG TCT CTG GGA ATT GTG GGA TTG GCA ATA CTG GCT
--- --- --- --- --- --- --- --- --- --- --- --- --- --- --- --- --- ---
 W   R   M   E   I   Y   V   S   L   G   I   V   G   L   A   I   L   A 767             776             785             794             803             812
CTG TTG GCT GTG ACA TCT ATT CCA TCT GTG AGT GAC TCT TTG ACA TGG AGA GAA
--- --- --- --- --- --- --- --- --- --- --- --- --- --- --- --- --- ---
 L   L   A   V   T   S   I   P   S   V   S   D   S   L   T   W   R   E 821             830             839             848             857             866
TTT CAC TAT ATT CAG AGC AAG CTA GGA ATT GTT TCC CTT CTA CTG GGC ACA ATA
--- --- --- --- --- --- --- --- --- --- --- --- --- --- --- --- --- ---
 F   H   Y   I   Q   S   K   L   G   I   V   S   L   L   L   G   T   I 875             884             893             902             911             920
CAC GCA TTG ATT TTT GCC TGG AAT AAG TGG ATA GAT ATA AAA CAA TTT GTA TGG
--- --- --- --- --- --- --- --- --- --- --- --- --- --- --- --- --- ---
 H   A   L   I   F   A   W   N   K   W   I   D   I   K   Q   F   V   W 929             938             947             956             965             974
TAT ACA CCT CCA ACT TTT ATG ATA GCT GTT TTC CTT CCA ATT GTT GTC CTG ATA
--- --- --- --- --- --- --- --- --- --- --- --- --- --- --- --- --- ---
 Y   T   P   P   T   F   M   I   A   V   F   L   P   I   V   V   L   I 983             992            1001            1010            1019            1028
TTT AAA AGC ATA CTA TTC CTG CCA TGC TTG AGG AAG AAG ATA CTG AAG ATT AGA
--- --- --- --- --- --- --- --- --- --- --- --- --- --- --- --- --- ---
 F   K   S   I   L   F   L   P   C   L   R   K   K   I   L   K   I   R 1037            1046            1055            1064            1073            1082
CAT GGT TGG GAA GAC GTC ACC AAA ATT AAC AAA ACT GAG ATA TGT TCC CAG TTG
--- --- --- --- --- --- --- --- --- --- --- --- --- --- --- --- --- ---
 H   G   W   E   D   V   T   K   I   N   K   T   E   I   C   S   Q   L 1091            1100            1109            1118            1127            1136
TAG AAT TAC TGT TTA CAC ACA TTT TTG TTC AAT ATT GAT ATA TTT TAT CAC CAA
--- --- --- --- --- --- --- --- --- --- --- --- --- --- --- --- --- ---
 *   N   Y   C   L   H   T   F   L   F   N   I   D   I   F   Y   H   Q 1145            1154            1163            1172            1181            1190
CAT TTC AAG TTT GTA TTT GTT AAT AAA ATG ATT ATT CAA GGA AAA AAA AAA AAA
--- --- --- --- --- --- --- --- --- --- --- --- --- --- --- --- --- ---
 H   F   K   F   V   F   V   N   K   M   I   I   Q   G   K   K   K   K

AAA AA 3'   SEQ ID NO:1
--- --
 K          SEQ ID NO:2
```

FIG. 1C

GGC GGA GGC GGA GGC GGA GGG CGA GGG GCG GGG AGC GCC GCC TGG AGC GCG

GCA GGT CAT ATT GAA CAT TCC AGA TAC CTA TCA TTA CTC GAT GCT GTT GAT

AAC AGC AAG     3'  SEQ ID NO:3

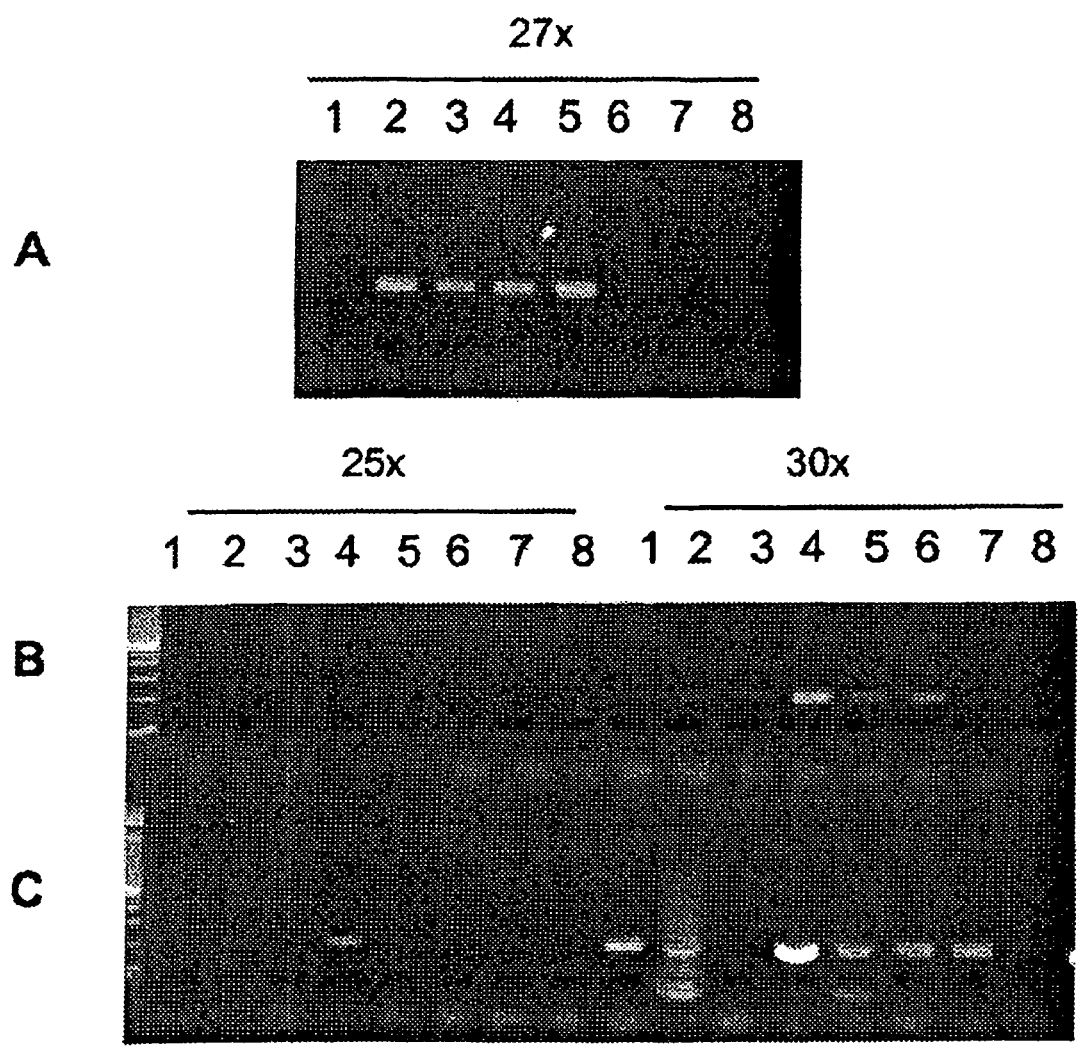

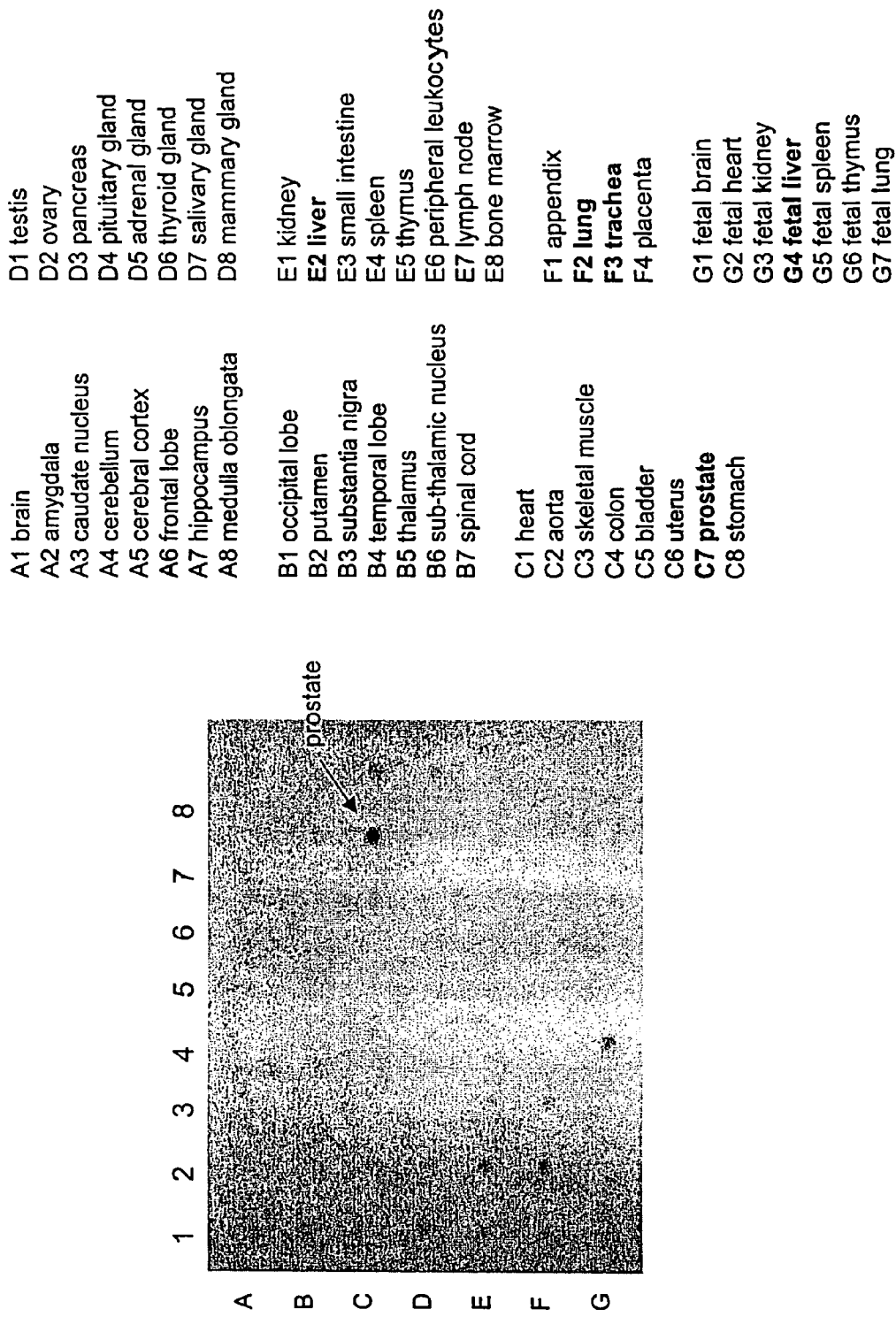

FIG. 4A

GGGGCCCGCACCTCTGGGCAGCAGCGGCAGCCGAGACTCACGGTCAAGCTAAGGCGAAGAGTGGGTGGCTGAAGCC
ATACTATTTTATAGAATTAATGGAAAGCAGAAAAGACATCACAAACCAAGAAGAACTTTGGAAAATGAAGCCTAGG
AGAAATTTAGAAGAAGACGATTATTTGCATAAGGACACGGGAGAGACCAGCATGCTAAAAAGACCTGTGCTTTTGC
ATTTGCACCAAACAGCCCATGCTGATGAATTTGACTGCCCTTCAGAACTTCAGCACACACAGGAACTCTTTCCACA
GTGGCACTTGCCAATTAAAATAGCTGCTATTATAGCATCTCTGACTTTTCTTTACACTCTTCTGAGGGAAGTAATT
CACCCCTTAGCAACTTCCCATCAACAATATTTTTATAAAATTCCAATCCTGGTCATCAACAAAGTCTTGCCAATGG
TTTCCATCACTCTCTTGGCATTGGTTTACCTGCCAGGTGTGATAGCAGCAATTGTCCAACTTCATAATGGAACCAA
GTATAAGAAGTTTCCACATTGGTTGGATAAGTGGATGTTAACAAGAAAGCAGTTTGGGCTTCTCAGTTTCTTTTTT
GCTGTACTGCATGCAATTTATAGTCTGTCTTACCCAATGAGGCGATCCTACAGATACAAGTTGCTAAACTGGGCAT
ATCAACAGGTCCAACAAAATAAAGAAGATGCCTGGATTGAGCATGATGTTTGGAGAATGGAGATTTATGTGTCTCT
GGGAATTGTGGGATTGGCAATACTGGCTCTGTTGGCTGTGACATCTATTCCATCTGTGAGTGACTCTTTGACATGG
AGAGAATTTCACTATATTCAGGTAAATAATATATAAAATAACCCTAAGAGGTAAATCTTCTTTTTGTGTTTATGAT
ATAGAATATGTTGACTTTACCCCATAAAAAATAACAAATGTTTTTCAACAGCAAAGATCTTATACTTGTTCCAATT
AATAATGTGCTCTCCTGTTGTTTTCCCTATTGCTTCTAATTAGGACAAGTGTTTCCTAGACATAAATAAAAGGCAT
TAAAATATTCTTTGTTTTTTTTTTTTGTTTGTTTGTTTTTGTTTGTTTGTTTGTTTTTTTGAGATGAAGTCTCG
CTCTGTTGCCCATGCTGGAGTACAGTGGCACGATCTCGGCTCACTGCAACCTGCGCCTCCTGGGTTCAGGCGATTC
TCTTGCCTCAGCCTCCTGAGTAGCTGGGATTACAGGCACCCATCACCATGTCCAGCTAATTTTTGTATTTTTAGTA
GAGACAGGGTTTTCCCATGTTGGCCAGGCTGGTCTCGATCTCCTGACCTCAAATGATCCGCCCACCTCGGCCTCCC
AAAGTGCTGGGATGACAGTTGTGAGCCACCACACTCAGCCTGCTCTTTCTAATATTTGAAACTTGTTAGACAATTT
GCTACCCATCTAATGTGATATTTTAGGAATCCAATATGCATGGTTTATTATTTCTTAAAAAAAATATTCTTTTACC
TGTCACCTGAATTTAGTAATGCCTTTTATGTTACACAACTTAGCACTTTCCAGAAACAAAAACTCTCTCCTTGAAA
TAATAGAGTTTTTATCTACCAAAGATATGCTAGTGTCTCATTTCAAAGGCTGCTTTTTCCAGCTTACATTTTATAT
ACTTACTCACTTGAAGTTTCTAAATATTCTTGTAATTTTAAAACTATCTCAGATTTACTGAGGTTTATCTTCTGGT
GGTAGATTATCCATAAGAAGAGTGATGTGCCAGAATCACTCTGGGATCCTTGTCTGACAAGATTCAAAGGACTAAA
TTTAATTCAGTCATGAACACTGCCAATTACCGTTTATGGGTAGACATCTTTGGAAATTTCCACAAGGTCAGACATT
CGCAACTATCCCTTCTACATGTCCACACGTATACTCCAACACTTTATTAGGCATCTGATTAGTTTGGAAAGTATGC

FIG. 4B

```
CTCCATCTGAATTAGTCCAGTGTGGCTTAGAGTTGGTACAACATTCTCACAGAATTTCCTAATTTTGTAGGTTCAG
CCTGATAACCACTGGAGTTCTTTGGTCCTCATTAAATAGCTTTCTTCACACATTGCTCTGCCTGTTACACATATGA
TGAACACTGCTTTTTAGACTTCATTAGGAATTTAGGACTGCATCTTGACAACTGAGCCTATTCTACTATATGTACA
ATACCTAGCCCATAATAGGTATACAATACACATTTGGTAAAACTAATTTTCAACCAATGACATGTATTTTTCAACT
AGTAACCTAGAAATGTTTCACTTAAAATCTGAGAACTGGTTACACTACAAGTTACCTTGGAGATTCATATATGAAA
ACGCAAACTTAGCTATTTGATTGTATTCACTGGGACTTAAGAATGCGCCTGAATAATTGTGAGTTCGATTTGTTCT
GGCAGGCTAATGACCATTTCCAGTAAAGTGAATAGAGGTCAGAAGTCGTATAAAAGAGGTGTTGTCAGAACACCGT
TGAGATTACATAGGTGAACAACTATTTTTAAGCAACTTTATTTGTGTAGTGACAAAGCATCCCAATGCAGGCTGAA
ATGTTTCATCACATCTCTGGATCTCTCTATTTGTGCAGACATTGAAAAAATTGTTCATATTATTTCCATGTTATC
AGAATATTTGATTTTTTAAAAACATAGGCCAAGTTCATTCACTTCATTATTCATTTATCAAAATCAGAGTGAATCA
CATTAGTCGCCTTCACAACTGATAAAGATCACTGAAGTCAAATTGATTTTTGCTATAATCTTCAATCTACCTATAT
TTAATTGAGAATCTAAAATGTACAAATCATTGTGTTGATTCTGCAGTGATCCTGCTATAAGTAAGACTCAGTCCCT
GATTTTAGGTATCCTGTGAAAAGCAGAATTAAGACAAATACACAAGAGACAAAGCACAAAAAATAAATATCATAAG
GGGATGAACAAAATGGTGGAGAAAGAGTAGACAAAGTTTTTGATCACCTGCCTTCAAAGAAAGGCTGTGAATTTTG
TTCACTTAGACAGCTTGGAGACAAGAAATTACCCAAAAGTAAGGTGAGGAGGATAGGCAAAAAGAGCAGAAAGATG
TGAATGGACATTGTTGAGAAATGTGATAGGAAAACAATCATAGATAAAGGATTTCCAAGCAACAGAGCATATCCAG
ATGAGGTAGGATGGGATAAACTCTTATTGAACCAATCTTCACCAATTTTGTTTTTCTTTTGCAGAGCAAGCTAGGA
ATTGTTTCCCTTCTACTGGGCACAATACACGCATTGATTTTTGCCTGGAATAAGTGGATAGATATAAAACAATTTG
TATGGTATACACCTCCAACTTTTATGATAGCTGTTTTCCTTCCAATTGTTGTCCTGATATTTAAAAGCATACTATT
CCTGCCATGCTTGAGGAAGAAGATACTGAAGATTAGACATGGTTGGGAAGACGTCACCAAAATTAACAAAACTGAG
ATATGTTCCCAGTTGTAGAATTACTGTTTACACACATTTTTGTTCAATATTGATATATTTTATCACCAACATTTCA
AGTTTGTATTTGTTAATAAAATGATTATTCAAGGAAAAAAAAAAAAAAAAAAAAAA      SEQ ID NO:6
```

FIG. 5
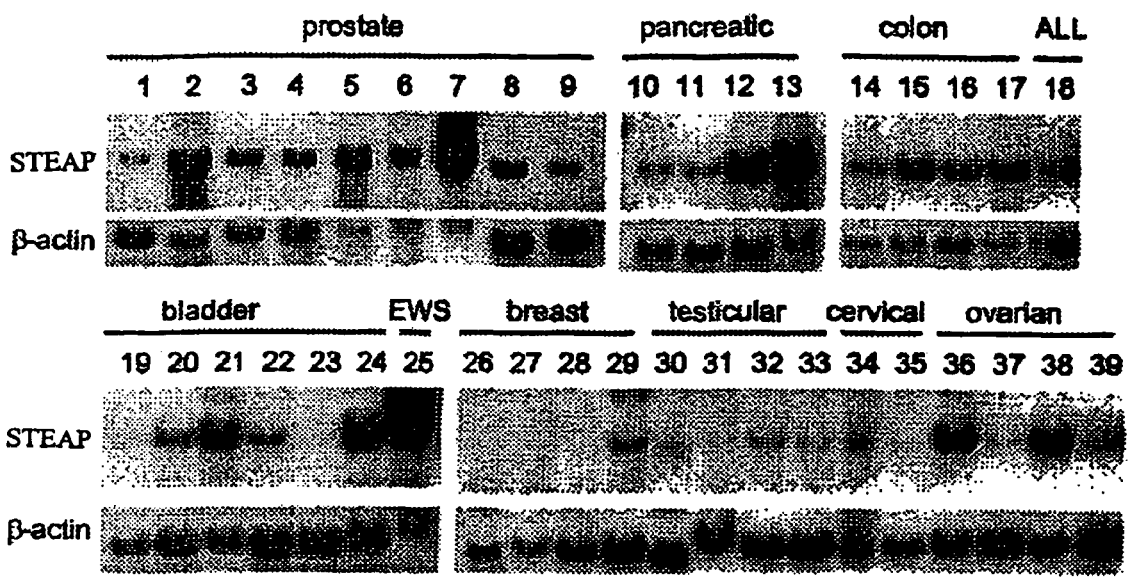
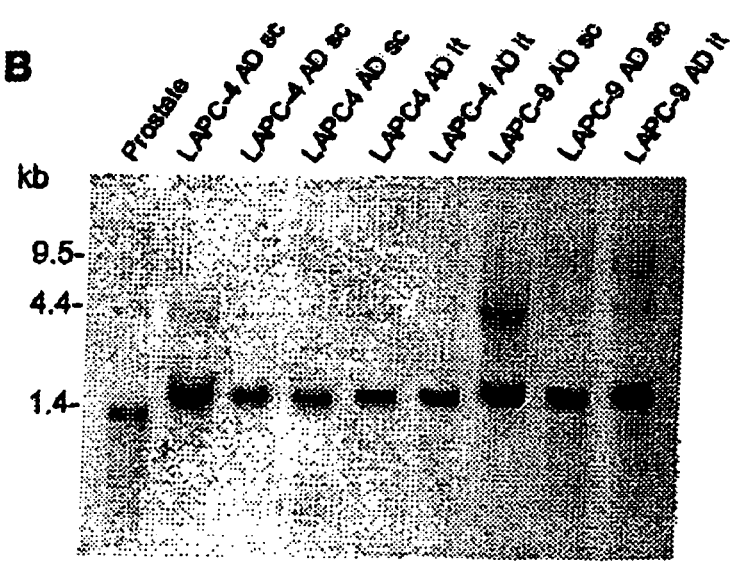

FIG. 9

```
              10              19              28              37              46              55
GAC TTT TAC AAA ATT CCT ATA GAG ATT GTG AAT AAA ACC TTA CCT ATA GTT GCC
--- --- --- --- --- --- --- --- --- --- --- --- --- --- --- --- --- ---
Asp Phe Tyr Lys Ile Pro Ile Glu Ile Val Asn Lys Thr Leu Pro Ile Val Ala
              64              73              82              91             100             109
ATT ACT TTG CTC TCC CTA GTA TAC CTC GCA GGT CTT CTG GCA GCT GCT TAT CAA
--- --- --- --- --- --- --- --- --- --- --- --- --- --- --- --- --- ---
Ile Thr Leu Leu Ser Leu Val Tyr Leu Ala Gly Leu Leu Ala Ala Ala Tyr Gln
             118             127             136             145             154             163
CTT TAT TAC GGC ACC AAG TAT AGG AGA TTT CCA CCT TGG TTG GAA ACC TGG TTA
--- --- --- --- --- --- --- --- --- --- --- --- --- --- --- --- --- ---
Leu Tyr Tyr Gly Thr Lys Tyr Arg Arg Phe Pro Pro Trp Leu Glu Thr Trp Leu
             172             181             190             199             208             217
CAG TGT AGA AAA CAG CTT GGA TTA CTA AGT TTT TTC TTC GCT ATG GTC CAT GTT
--- --- --- --- --- --- --- --- --- --- --- --- --- --- --- --- --- ---
Gln Cys Arg Lys Gln Leu Gly Leu Leu Ser Phe Phe Phe Ala Met Val His Val
             226             235             244             253             262             271
GCC TAC AGC CTC TGC TTA CCG ATG AGA AGG TCA GAG AGA TAT TTG TTT CTC AAC
--- --- --- --- --- --- --- --- --- --- --- --- --- --- --- --- --- ---
Ala Tyr Ser Leu Cys Leu Pro Met Arg Arg Ser Glu Arg Tyr Leu Phe Leu Asn
             280             289             298             307             316             325
ATG GCT TAT CAG CAG GTT CAT GCA AAT ATT GAA AAC TCT TGG AAT GAG GAA GAA
--- --- --- --- --- --- --- --- --- --- --- --- --- --- --- --- --- ---
Met Ala Tyr Gln Gln Val His Ala Asn Ile Glu Asn Ser Trp Asn Glu Glu Glu
             334             343             352             361             370             379
GTT TGG AGA ATT GAA ATG TAT ATC TCC TTT GGC ATA ATG AGC CTT GGC TTA CTT
--- --- --- --- --- --- --- --- --- --- --- --- --- --- --- --- --- ---
Val Trp Arg Ile Glu Met Tyr Ile Ser Phe Gly Ile Met Ser Leu Gly Leu Leu
             388             397             406             415             424             433
TCC CTC CTG GCA GTC ACT TCT ATC CCT TCA GTG AGC AAT GCT TTA AAC TGG AGA
--- --- --- --- --- --- --- --- --- --- --- --- --- --- --- --- --- ---
Ser Leu Leu Ala Val Thr Ser Ile Pro Ser Val Ser Asn Ala Leu Asn Trp Arg
             442             451             460             469             478             487
GAA TTC AGT TTT ATT CAG TCT ACA CTT GGA TAT GTC GCT CTG CTC ATA AGT ACT
--- --- --- --- --- --- --- --- --- --- --- --- --- --- --- --- --- ---
Glu Phe Ser Phe Ile Gln Ser Thr Leu Gly Tyr Val Ala Leu Leu Ile Ser Thr
             496             505             514
TTC CAT GTT TTA ATT TAT GGA TGG AAA CGA GCT 3'    SEQ ID NO:7
--- --- --- --- --- --- --- --- --- --- ---
Phe His Val Leu Ile Tyr Gly Trp Lys Arg Ala          SEQ ID NO:8
```

FIG. 10

STEAP-2, AA508880 (NCI_CGAP Pr6) SEQ ID NO:9
ggtcgactttttcctttattccttttgtcagagatctgattcatccatatgctagaaaccaacagagtgacttttaca
aaattcctatagagattgtgaataaaaccttacctatagttgccattactttgctctccctagtataccttgcagg
tcttctggcagctgcttatcaactttattacggcaccaagtataggagatttccaccttggttggaaacctggtta
cagtgtagaaaacagcttggattactaagttgtttcttcgctatggtccatgttgcctacagcctctgcttaccga
tgagaaggtcagagagat

STEAP-2, 98P4B6 SSH fragment SEQ ID NO:10
TTTGCAGCTTTGCAGATACCCAGACTGAGCTGGAACTGGAATTTGTCTTCCTATTGACTCTACTTCTTTAAAAGCG
GCTGCCCATTACATTCCTCAGCTGTCCTTGCAGTTAGGTGTACATGTGACTGAGTGTTGGCCAGTGAGATGAAGTC
TCCTCAAAGGAAGGCAGCATGTGTCCTTTTT

AI139607 (testis EST) SEQ ID NO:11
aagaaggagaatccatttagcacctcctcagcctggctcagtgattcatatgtggctttgggaatacttgggtttt
ttctgtttgtactcttggggaatcacttctttgccatctgttagcaatgcagtcaactggagagagttccgatttgt
ccagtccaaactgggttatttgaccctgatcttgtgtacagcccacaccctggtgtacggtgggaagagattcctc
agcccttcaaatctcagatggtatcttcctgcagcctacgtgttagggcttatcattccttgcactgtgctggtga
tcaagtttgtcctaatcatgccatgtgtagacaacacccttacaaggatccgccagggctgggaaaggaactcaaa
acactagaaaaagcattgaatggaaaatcaatatttaaaacaaagttcaatttagctggaaaaaaaaaa

R80991 (placental EST) SEQ ID NO:12
ggccgcggcanccgctacgacctggtcaacctggcagtcaagcaggtcttggccanacaagagccacctctgggtg
aaggaggaggtctggcggatggagatctacctctccctgggagtgctggccctcggcacgttgtccctgctggccg
tgacctcactgccgtccattgcaaactcgctcaactggagggagttcagcttcgttcagtcctcactgggctttgt
ggccntcgtgctgagcacactncacacgctcacctacggctggacccgcgccttcgaggagagccgctacaagttc
tacctncctcccaccttcacgntcacgctgctggtgccctgcgttcgttcatcctgggccaaagccctgtttntac
tgccttgcattcagccgnaga

FIG. 11A

```
STEAP-1   106  FYKIPILVINKVLPMVSITLLALVYLPGVIAAIVQLHNGTKYKKPPHWLDKWMLTRKQPG
STEAP-2     2  FYKIPIBIVNKTLPIVAITLLSLVYLAGLLAAAYQLYYGTKYRRFPPWLETWLQCRKQLG
               *****  ** ** * **** **** * ** ** **** ** ** *   *** *

STEAP-1   166  LLSFFFAVLHAIYSLSYPMRRSYRYKLLNWAYQQVQQNKEDAWIEHDVWRMEIYVSLGIV
STEAP-2    62  LLSFFFAMVHVAYSLCLPMRRSERYLFLNMAYQQVHANIENSWNEEEVWRIEMYISFGIM
               ******* * *** ***** ** ** ***** * *  * *  *** * * * **

STEAP-1   226  GLAILALLAVTSIPSVSDSLTWREPHYIQSKLGIVSLLLGTIHALIFAWNK   PORTION OF SEQ ID NO:2
STEAP-2   122  SLGLLSLLAVTSIPSVSNALNWREFSFIQSTLGYVALLISTFHVLIYGWKR   PORTION OF SEQ ID NO:8
               *  * *********** * **** *** ** * ** * ** * * ** *
```

FIG. 11B

```
              15 16           30 31           45 46           60 61           75 76            90
          1                                                                                             90
STEAP-1   MESRDITNQEELWK MKPRRNLEEDDYLHK DTGETSMLKRPVLLH LHQTAHADEFDCPSE LQHTQELPPQWHLPI KIAAIIASLTFLYTL      90
STEAP-2   --------------- --------------- --------------- --------------- --------------- ---------------  0
STEAP-3   --------------- --------------- --------------- --------------- --------------- ---------------  0
STEAP-4   --------------- --------------- --------------- --------------- --------------- ---------------  0

105 106         120 121         135 136         150 151         165 166          180
          91                                                                                           180
STEAP-1   LREVIHPLATSHQY FYKIPILVINWVLPW VSITLLAVLVIPGVI AAIVQLANGTKYKKF PWMLDKWMLTRKQFG LLSFFFAVLHAIYSI     180
STEAP-2   --------------D FYKLPILVYRNTLFI VALTLSSLVYTLAGLL AANYQLYYSTKYRRF DPWLETWLQ-RKQIQ LLSFFFAMVEVAIEI     76
STEAP-3   --------------- --------------- --------------- --------------- --------------- ---------------   0
STEAP-4   --------------- --------------- --------------- --------------- --------------- ---------------   0

195 196         210 211         225 226         240 241         255 256          270
          181                                                                                          270
STEAP-1   SYPMRRSYRYKLFNW AYQQVQQNKEDAWIE EDVWRMEIYVSLGIV GLAILALLAVTSIPS VSDSLTWREFHYIQS XLGIVSLLLGTIHAL    270
STEAP-2   CLFMRRSERYLFLNM AYQQVHANIENSRNE EVIERISFQIN SGLGLLSLLAVTSIPS VSNALNWREFSFIQS TLGYVLALLISTPHVI    166
STEAP-3   --------------- --------------- --------------- --------------- VSNAVNWREFRFVQS KLGYLTLILCTPAHTL    68
STEAP-4   ------ATTRSIW QSSRSWPKGSHLMVK KEVWRMEIYLSLGYV ALGTLSLLAVTBLPS IANSLAWREFSFVQS SLQFVAMVLSTLHTL     82

285 286         300 301         315 316         330 331         345 346          360
          271                                                                                          360
STEAP-1   IPAMRKWIDIKQFVM YLPPTFMCLAVTLPIV VLIPTSILFLTFCLPRK KLKIRHGEDVTKI NKTEICSQL                339   SEQ ID NO:2
STEAP-2   ITGWKRA-------- --------------- ---IYGWKRA---- ------------- ---                      173   SEQ ID NO:8
STEAP-3   VYGGKRFLSPSNLRM YLPAAYVLGLIIPCI FLVLGYVLLDMPCVDN TLTEIFQCWERNSKH ---                   128   SEQ ID NO:33
STEAP-4   TYGWTRAFEESEIKF YLPPTFIXYLLIVPCV RSSMAKALFXLPCIQ P--                                  128   SEQ ID NO:34
```

A
1. Brain
2. Heart
3. Kidney
4. Liver
5. Lung
6. Pancreas
7. Placenta
8. Skeletal Muscle

B
1. Colon
2. Ovary
3. Leukocytes
4. Prostate
5. Small Intestine
6. Spleen
7. Testis
8. Thymus A
1. Brain
2. Heart
3. Kidney
4. Liver
5. Lung
6. Pancreas
7. Placenta
8. Skeletal Muscle B
1. Colon
2. Ovary
3. Leukocytes
4. Prostate
5. Small Intestine
6. Spleen
7. Testis
8. Thymus

A
1. Brain
2. Prostate
3. LAPC-4 AD
4. LAPC-4 AI
5. LAPC-9 AD
6. HeLa
7. Murine cDNA
8. Neg. control

B
1. Colon
2. Ovary
3. Leukocytes
4. Prostate
5. Small Intestine
6. Spleen
7. Testis
8. Thymus

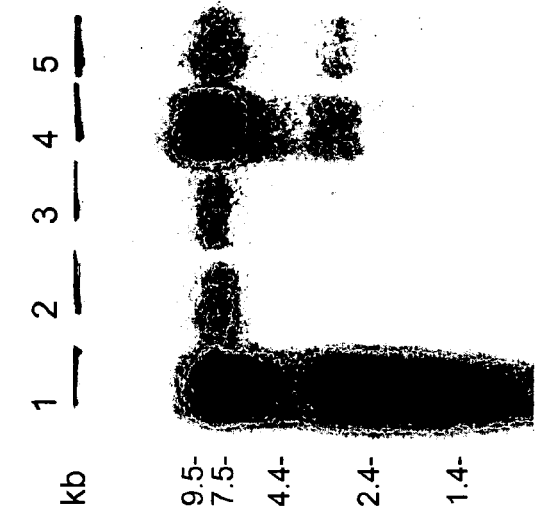
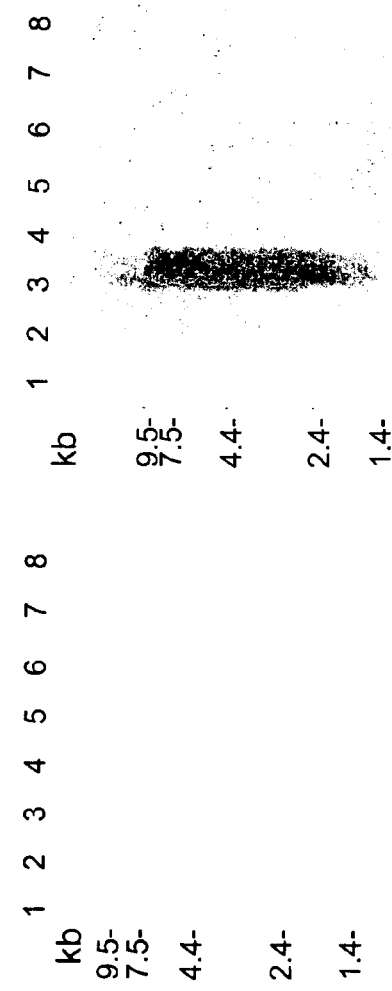
FIG. 15
FIG. 15A
FIG. 15B
FIG. 15C
A
1. Heart
2. Brain
3. Placenta
4. Lung
5. Liver
6. Skeletal Muscle
7. Kidney
8. Pancreas
B
1. Spleen
2. Thymus
3. Prostate
4. Testis
5. Ovary
6. Small Intestine
7. Colon
8. Leukocytes
C
1. Prostate
2. LAPC-4 AD
3. LAPC-4 AI
4. LAPC-9 AD
5. LAPC-9 AI

Lanes
1) 1kb ladder
2) human female genomic
3) 12P11 BAC mus
4) human female genomic
5) 12P11 BAC mus
6) 3T3

SERPENTINE TRANSMEMBRANE ANTIGENS EXPRESSED IN HUMAN CANCERS AND USES THEREOF

CROSS-REFERENCE TO RELATED APPLICATIONS

This application is a continuation of U.S. patent application Ser. No. 10/750,262, filed Dec. 31, 2003, now U.S. Pat. No. 7,166,714 which is a divisional of U.S. patent application Ser. No. 10/011,095, filed Dec. 6, 2001, now issued as U.S. Pat. No. 7,053,186 on May 30, 2006, which is a divisional of U.S. patent application Ser. No. 09/323,873, filed Jun. 1, 1999, now issued as U.S. Pat. No. 6,329,503 on Dec. 11, 2001, which claims the benefit of U.S. Provisional Application No. 60/091,183, filed Jun. 30, 1998 and U.S. Provisional Application No. 60/087,520, filed Jun. 1, 1998. This application relates to U.S. Provisional Application No. 60/317,840, filed Sep. 6, 2001, U.S. Provisional Application No. 60/370,387, filed Apr. 5, 2002, 2002, U.S. patent application Ser. No. 10/010,667, filed Dec. 6, 2001, now issued as U.S. Pat. No. 6,887,975 on May 3, 2005, U.S. patent application Ser. No. 10/858,887, filed Jun. 1, 2004, U.S. patent application Ser. No. 11/225,661, filed Sep. 12, 2005, U.S. patent application Ser. No. 10/236,878, filed Sep. 6, 2002, U.S. patent application Ser. No. 10/830,899, filed Apr. 23, 2004, and U.S. patent application Ser. No. 10/861,662, filed Jun. 4, 2004. The contents of the applications listed in this paragraph are fully incorporated by reference herein.

FIELD OF THE INVENTION

The invention described herein relates to a family of novel genes and their encoded proteins and tumor antigens, termed STEAPs, and to diagnostic and therapeutic methods and compositions useful in the management of various cancers, particularly including prostate cancer, colon cancer, bladder cancer, ovarian cancer and pancreatic cancer.

BACKGROUND OF THE INVENTION

Cancer is the second leading cause of human death next to coronary disease. Around the world, millions of people die from cancer every year. In the United States alone, cancer cause the death of well over a half-million people each year, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the leading causes of cancer death. These and virtually all other carcinomas share a common lethal feature. With very few exceptions, metastatic disease from a carcinoma is fatal. Moreover, even for those cancer patients that initially survive their primary cancers, common experience has shown that their lives are dramatically altered. Many cancer patients experience strong anxieties driven by the awareness of the potential for recurrence or treatment failure. Many cancer patients experience physical debilitations following treatment.

Generally speaking, the fundamental problem in the management of the deadliest cancers is the lack of effective and non-toxic systemic therapies. Molecular medicine, still very much in its infancy, promises to redefine the ways in which these cancers are managed. Unquestionably, there is an intensive worldwide effort aimed at the development of novel molecular approaches to cancer diagnosis and treatment. For example, there is a great interest in identifying truly tumor-specific genes and proteins that could be used as diagnostic and prognostic markers and/or therapeutic targets or agents. Research efforts in these areas are encouraging, and the increasing availability of useful molecular technologies has accelerated the acquisition of meaningful knowledge about cancer. Nevertheless, progress is slow and generally uneven.

Recently, there has been a particularly strong interest in identifying cell surface tumor-specific antigens which might be useful as targets for various immunotherapeutic or small molecule treatment strategies. A large number of such cell-surface antigens have been reported, and some have proven to be reliably associated with one or more cancers. Much attention has been focused on the development of novel therapeutic strategies which target these antigens. However, few truly effective immunological cancer treatments have resulted.

The use of monoclonal antibodies to tumor-specific or over-expressed antigens in the treatment of solid cancers is instructive. Although antibody therapy has been well researched for some 20 years, only very recently have corresponding pharmaceuticals materialized. One example is the humanized anti-HER2/neu monoclonal antibody, Herceptin, recently approved for use in the treatment of metastatic breast cancers overexpressing the HER2/neu receptor. Another is the human/mouse chimeric anti-CD20/B cell lymphoma antibody, Rituxan, approved for the treatment of non-Hodgkin's lymphoma. Several other antibodies are being evaluated for the treatment of cancer in clinical trials or in pre-clinical research, including a fully human IgG2 monoclonal antibody specific for the epidermal growth factor receptor (Yang et al., 1999, Cancer Res. 59: 1236). Evidently, antibody therapy is finally emerging from a long embryonic phase. Nevertheless, there is still a very great need for new, more-specific tumor antigens for the application of antibody and other biological therapies. In addition, there is a corresponding need for tumor antigens which may be useful as markers for antibody-based diagnostic and imaging methods, hopefully leading to the development of earlier diagnosis and greater prognostic precision.

As discussed below, the management of prostate cancer serves as a good example of the limited extent to which molecular biology has translated into real progress in the clinic. With limited exceptions, the situation is more or less the same for the other major carcinomas mentioned above.

Worldwide, prostate cancer is the fourth most prevalent cancer in men. In North America and Northern Europe, it is by far the most common male cancer and is the second leading cause of cancer death in men. In the United States alone, well over 40,000 men die annually of this disease, second only to lung cancer. Despite the magnitude of these figures, there is still no effective treatment for metastatic prostate cancer. Surgical prostatectomy, radiation therapy, hormone ablation therapy, and chemotherapy remain as the main treatment modalities. Unfortunately, these treatments are clearly ineffective for many. Moreover, these treatments are often associated with significant undesirable consequences.

On the diagnostic front, the serum PSA assay has been a very useful tool. Nevertheless, the specificity and general utility of PSA is widely regarded as lacking in several respects. Neither PSA testing, nor any other test nor biological marker has been proven capable of reliably identifying early-stage disease. Similarly, there is no marker available for predicting the emergence of the typically fatal metastatic stage of the disease. Diagnosis of metastatic prostate cancer is achieved by open surgical or laparoscopic pelvic lymphadenectomy, whole body radionuclide scans, skeletal radiography, and/or bone lesion biopsy analysis. Clearly, better imaging and other less invasive diagnostic methods offer the promise of easing the difficulty those procedures place on a patient, as well as improving therapeutic options. However, until there are prostate tumor markers capable of reliably identifying early-stage disease, predicting susceptibility to metastasis, and precisely imaging tumors, the management of prostate cancer will continue to be extremely difficult. Accordingly, more specific molecular tumor markers are clearly needed in the management of prostate cancer.

There are some known markers which are expressed predominantly in prostate, such as prostate specific membrane antigen (PSM), a hydrolase with 85% identity to a rat neuropeptidase (Carter et al., 1996, Proc. Natl. Acad. Sci. USA 93: 749; Bzdega et al., 1997, J. Neurochem. 69: 2270). However, the expression of PSM in small intestine and brain (Israeli et al., 1994, Cancer Res. 54: 1807), as well its potential role in neuropeptide catabolism in brain, raises concern of potential neurotoxicity with anti-PSM therapies. Preliminary results using an Indium-111 labeled, anti-PSM monoclonal antibody to image recurrent prostate cancer show some promise (Sodee et al., 1996, Clin. Nuc. Med. 21: 759-766). More recently identified prostate cancer markers include PCTA-1 (Su et al., 1996, Proc. Natl. Acad. Sci. USA 93: 7252) and prostate stem cell antigen (PSCA) (Reiter et al., 1998, Proc. Natl. Acad. Sci. USA 95: 1735). PCTA-1, a novel galectin, is largely secreted into the media of expressing cells and may hold promise as a diagnostic serum marker for prostate cancer (Su et al., 1996). PSCA, a GPI-linked cell surface molecule, was cloned from LAPC 4 cDNA and is unique in that it is expressed primarily in basal cells of normal prostate tissue and in cancer epithelia (Reiter et al., supra). Vaccines for prostate cancer are also being actively explored with a variety of antigens, including PSM and PSA.

SUMMARY OF THE INVENTION

The present invention relates to a novel family of cell surface serpentine transmembrane antigens. Two of the proteins in this family are exclusively or predominantly expressed in the prostate, as well as in prostate cancer, and thus members of this family have been termed "STEAP" (Six Transmembrane Epithelial Antigens of the Prostate). Four particular human STEAPs are described and characterized herein. The human STEAPs exhibit a high degree of structural conservation among them but show no significant structural homology to any known human proteins.

The prototype member of the STEAP family, STEAP-1, appears to be a type IIIa membrane protein expressed predominantly in prostate cells in normal human tissues. Structurally, STEAP-1 is a 339 amino acid protein characterized by a molecular topology of six transmembrane domains and intracellular N— and C-termini, suggesting that it folds in a "serpentine" manner into three extracellular and two intracellular loops. STEAP-1 protein expression is maintained at high levels across various stages of prostate cancer. Moreover, STEAP-1 is highly over-expressed in certain other human cancers. In particular, cell surface expression of STEAP-1 has been definitively confirmed in a variety of prostate and prostate cancer cells, bladder cancer cells and colon cancer cells. These characteristics indicate that STEAP-1 is a specific cell-surface tumor antigen expressed at high levels in prostate, bladder, colon, and other cancers.

STEAP-2, STEAP-3 and STEAP-4 are also described herein. All are structurally related, but show unique expression profiles. STEAP-2, like STEAP-1, is prostate-specific in normal human tissues and is also expressed in prostate cancer. In contrast, STEAP-3 and STEAP-4 appear to show a different restricted expression pattern.

The invention provides polynucleotides corresponding or complementary to all or part of the STEAP genes, mRNAs, and/or coding sequences, preferably in isolated form, including polynucleotides encoding STEAP proteins and fragments thereof, DNA, RNA, DNA/RNA hybrid, and related molecules, polynucleotides or oligonucleotides complementary to the STEAP genes or mRNA sequences or parts thereof, and polynucleotides or oligonucleotides which hybridize to the STEAP genes, mRNAs, or to STEAP-encoding polynucleotides. Also provided are means for isolating cDNAs and the genes encoding STEAPs. Recombinant DNA molecules containing STEAP polynucleotides, cells transformed or transduced with such molecules, and host-vector systems for the expression of STEAP gene products are also provided. The invention further provides STEAP proteins and polypeptide fragments thereof. The invention further provides antibodies that bind to STEAP proteins and polypeptide fragments thereof, including polyclonal and monoclonal antibodies, murine and other mammalian antibodies, chimeric antibodies, humanized and fully human antibodies, and antibodies labeled with a detectable marker, and antibodies conjugated to radionuclides, toxins or other therapeutic compositions. The invention further provides methods for detecting the presence of STEAP polynucleotides and proteins in various biological samples, as well as methods for identifying cells that express a STEAP. The invention further provides various therapeutic compositions and strategies for treating prostate cancer, including particularly, antibody, vaccine and small molecule therapy.

BRIEF DESCRIPTION OF THE FIGURES

FIG. 2. Predominant expression of STEAP-1 in prostate tissue. First strand cDNA was prepared from 16-normal tissues, the LAPC xenografts (4AD, 4AI and 9AD) and HeLa cells. Normalization was performed by PCR using primers to actin and GAPDH. Semi-quantitative PCR, using primers derived from STEAP-1 (8P1D4) cDNA (FIG. 1A), shows predominant expression of STEAP-1 in normal prostate and the LAPC xenografts. The following primers were used to amplify STEAP-1:

```
8P1D4.1
5' ACTTTGTTGATGACCAGGATTGGA 3'    (SEQ ID NO: 4)

8P1D4.2
5' CAGAACTTCAGCACACACAGGAAC 3'    (SEQ ID NO: 5)
```

Figure 3A:
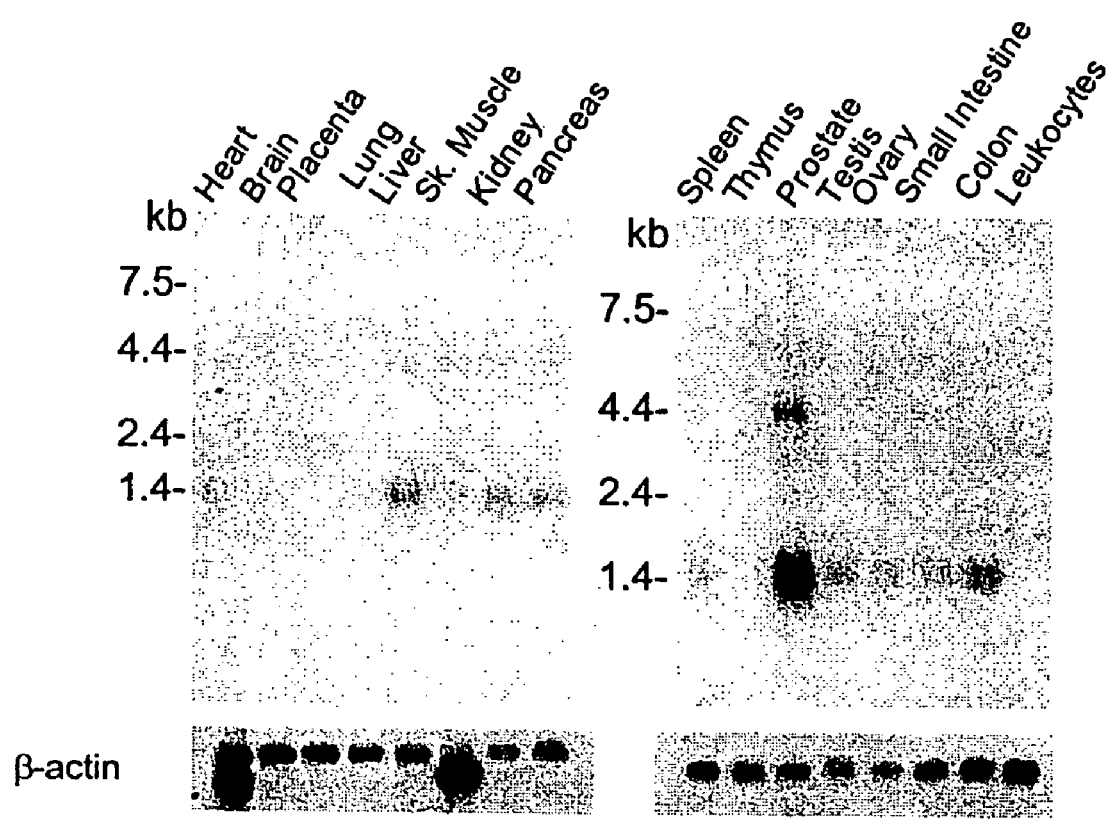

FIG. 3. Northern blot analyses of STEAP-1 expression in various normal human tissues and prostate cancer xenografts, showing predominant expression of STEAP-1 in prostate tissue. FIG. 3A: Two multiple tissue northern blots (Clontech) were probed with a full length STEAP cDNA clone 10 (FIG. 1A; SEQ ID NO: 1). Size standards in kilobases (kb) are indicated on the side. Each lane contains 2 μg of mRNA that was normalized by using a β-actin probe. FIG. 3B: Multiple tissue RNA dot blot (Clontech, Human Master Blot cat#7770-1) probed with STEAP-1 cDNA clone 10 (FIG. 1A; SEQ ID NO: 1), showing approximately five-fold greater expression in prostate relative to other tissues with significant detectable expression.

FIG. 4A-4B. Nucleotide sequence of STEAP-1 GTH9 clone (SEQ ID NO: 6) corresponding to the 4 kb message on northern blots (FIG. 3A). The sequence contains an intron of 2399 base pairs relative to the STEAP-1 clone 10 sequence of FIG. 1A; coding regions are nucleotides 96-857 and 3257-3510 (indicated in bold). The start ATG is in bold and underlined, the STOP codon is in bold and underlined, and the intron-exon boundaries are underlined.

FIG. 5. Expression of STEAP-1 in prostate and multiple cancer cell lines and prostate cancer xenografts. Xenograft and cell line filters were prepared with 10 μg of total RNA per lane. The blots were analyzed using the STEAP-1 clone 10 as probe. All RNA samples were normalized by ethidium bromide staining and subsequent analysis with a β-actin probe. FIG. 5A: Expression in various cancer cell lines and xenografts and prostate. Lanes as follows: (1) PrEC cells, (2) normal prostate tissue, (3) LAPC-4 AD xenograft, (4) LAPC-4 AI xenograft, (5) LAPC-9 AD xenograft, (6) LAPC-9 AI xenograft, (7) LNCaP cells, (8) PC-3 cells, (9) DU145 cells, (10) PANC-1 cells, (11) BxPC-3 cells, (12) HPAC cells, (13) Capan-1 cells, (14) CACO-2 cells, (15) LOVO cells, (16) T84 cells, (17) COLO-205 cells, (18) KCL-22 cells (acute lymphocytic leukemia, ALL), (19) HT1197 cells, (20) SCABER cells, (21) UM-UC-3 cells, (22) TCCSUP cells, (23) J82 cells, (24) 5637 cells, (25) RD-ES cells (Ewing sarcoma, EWS), (26) CAMA-1 cells, (27) DU4475 cells, (28) MCF-7 cells, (29) MDA-MB435s cells, (30) NTERA-2 cells, (31) NCCIT cells, (32) TERA-1 cells, (33) TERA-2 cells, (34) A431 cells, (35) HeLa cells, (36) OV-1063 cells, (37) PA-1 cells, (38) SW 626 cells, (39) CAOV-3 cells. FIG. 5B: The expression of STEAP-1 in subcutaneously (sc) grown LAPC xenografts compared to the expression in LAPC 4 and LAPC-9 xenografts grown in the tibia (it) of mice.

Figure 6:
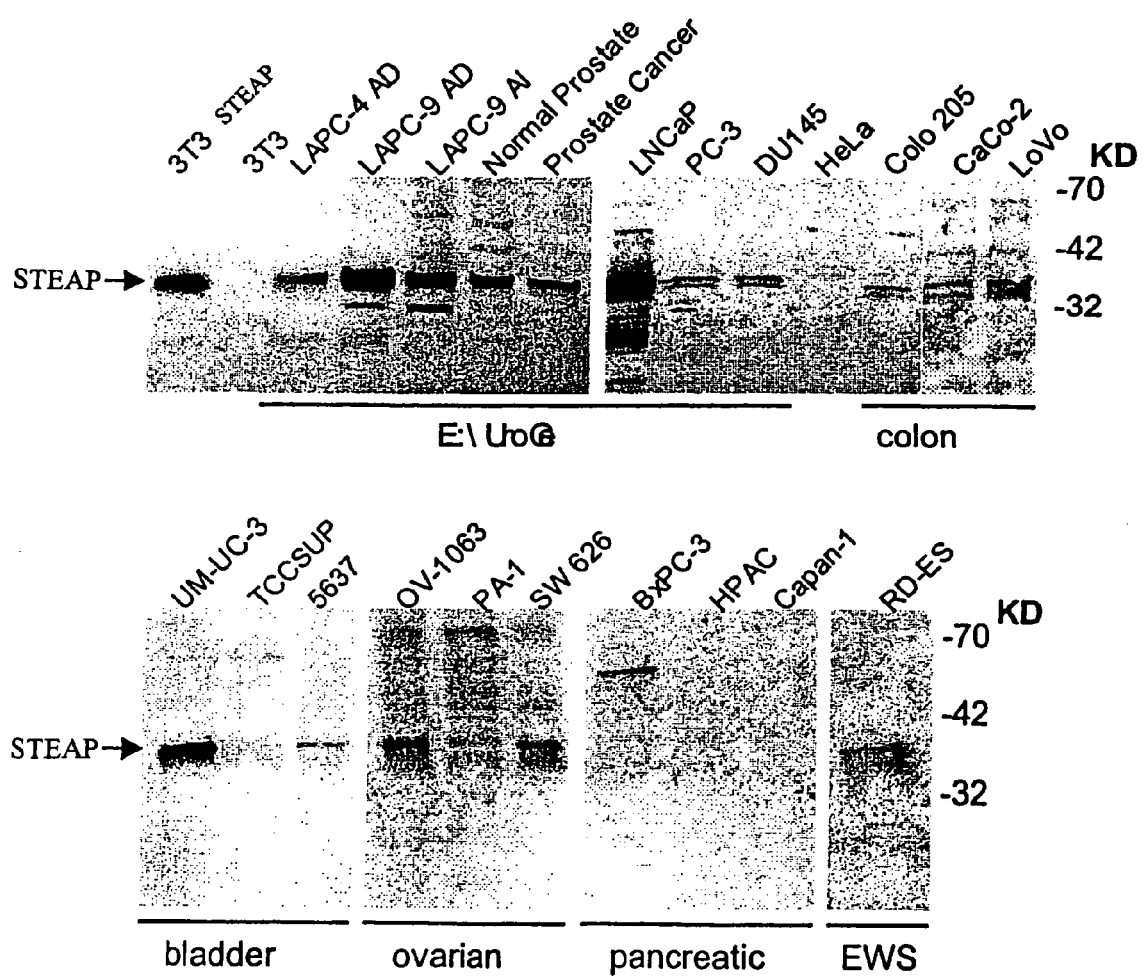

FIG. 6. Western blot analysis of STEAP-1 protein expression in tissues and multiple cell lines. Western blots of cell lysates prepared from prostate cancer xenografts and cell lines were probed with a polyclonal anti-STEAP-1 antibody preparation (see Example 3C for details). The samples contain 20 μg of protein and were normalized with anti-Grb-2 probing of the Western blots.

Figure 7:
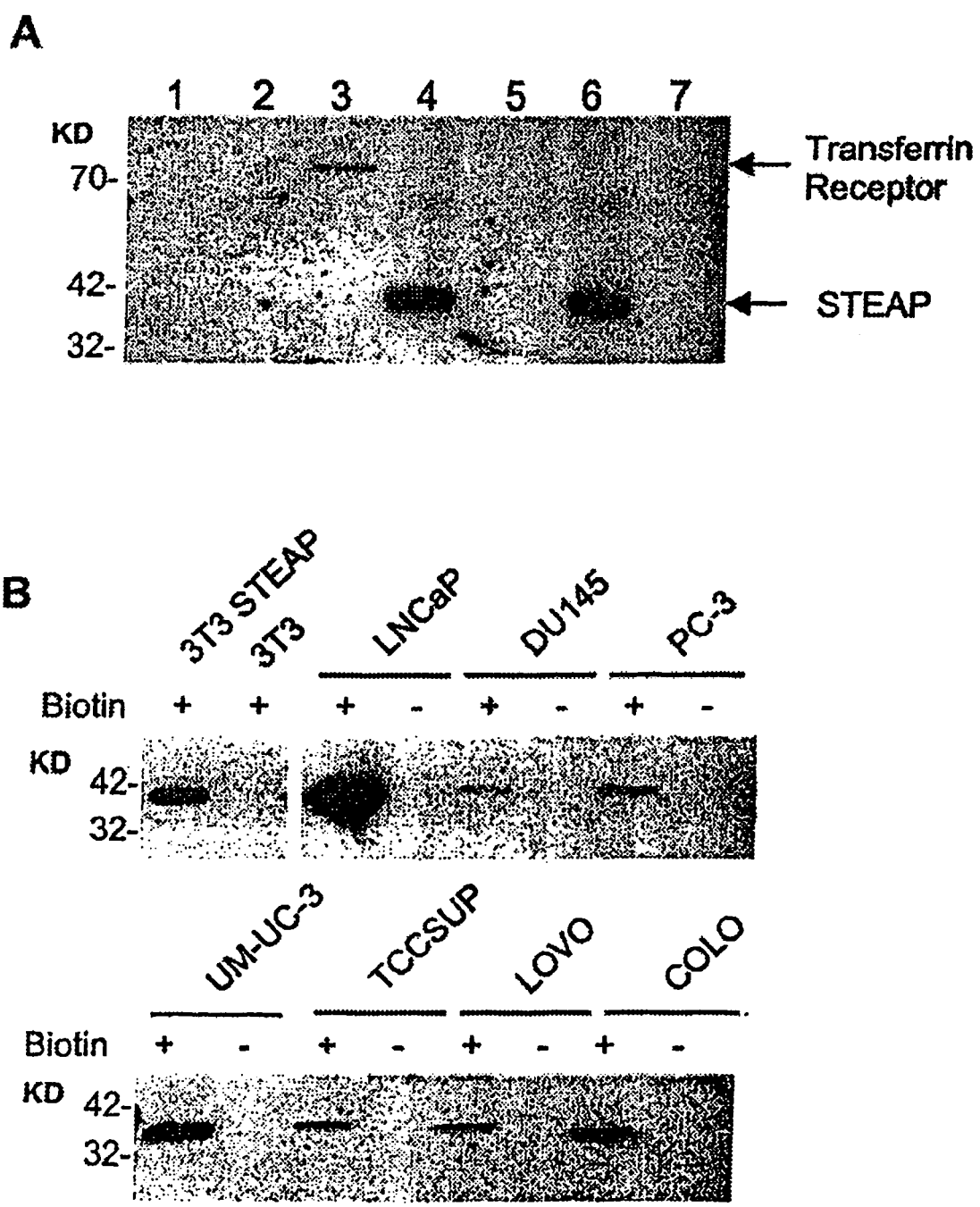

FIG. 7. Cell surface biotinylation of STEAP-1. FIG. 7A: Cell surface biotinylation of 293T cells transfected with vector alone or with vector containing cDNA encoding 6His-tagged STEAP-1. Cell lysates were immunoprecipitated with specific antibodies, transferred to a membrane and probed with horseradish peroxidase-conjugated streptavidin. Lanes 1-4 and 6 correspond to immunoprecipitates from lysates prepared from STEAP-1 expressing 293T cells. Lanes 5 and 7 are immunoprecipitates from vector transfected cells. The immunoprecipitations were performed using the following antibodies: (1) sheep non-immune, (2) anti-Large T antigen, (3) anti-CD71 (transferrin receptor), (4) anti-His, (5) anti-His, (6) anti-STEAP-1, (7) anti-STEAP-1. FIG. 7B: Prostate cancer (LNCaP, PC-3, DU145), bladder cancer (UM-UC-3, TCCSUP) and colon cancer (LOVO, COLO) cell lines were either biotinylated (+) or not (−) prior to lysis. Western blots of streptavidin-gel purified proteins were probed with anti-STEAP-1 antibodies. Molecular weight markers are indicated in kilodaltons (kD).

Figure 8:
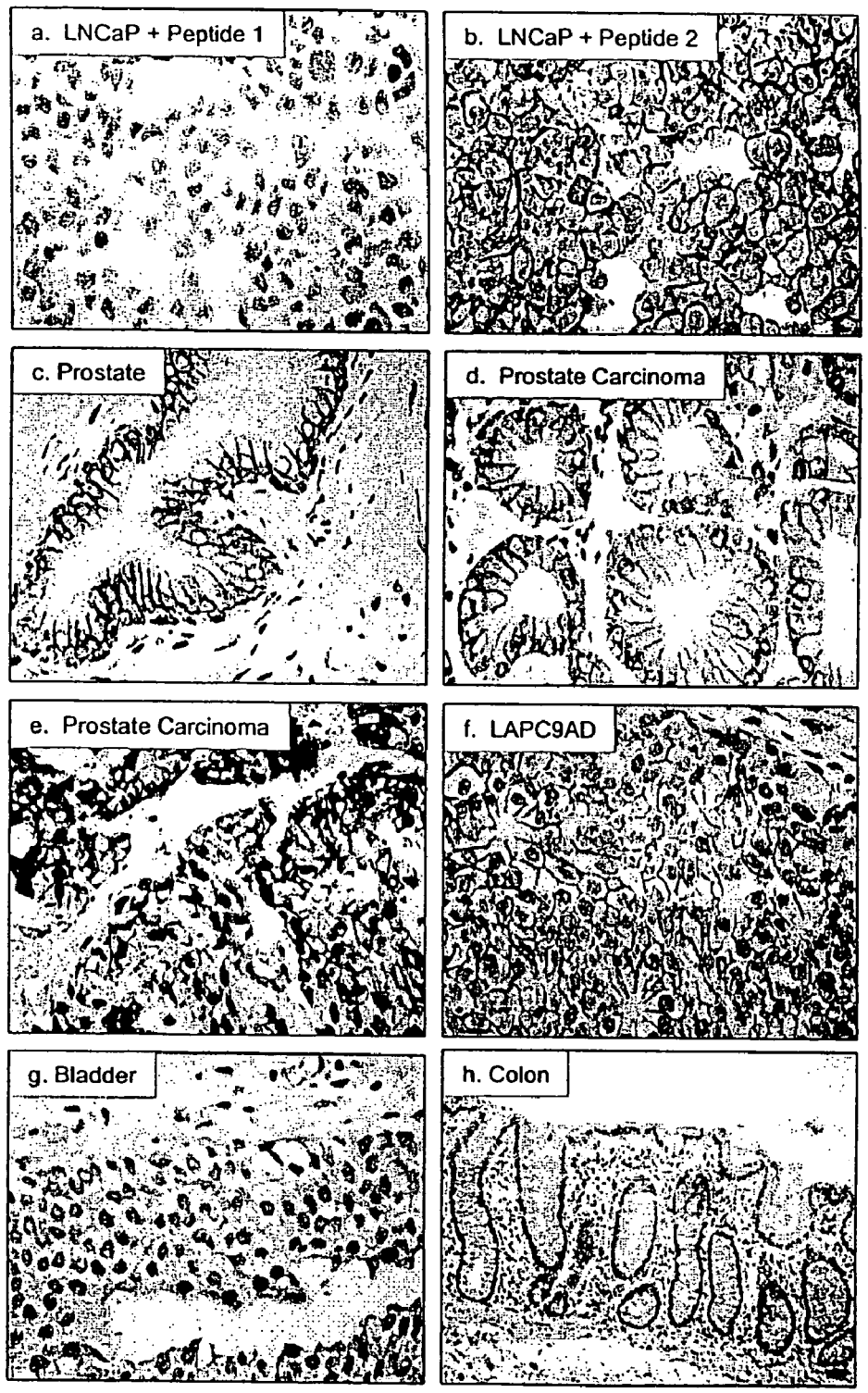

FIG. 8. Immunohistochemical analysis of STEAP-1 expression using anti-STEAP-1 polyclonal antibody. Tissues were fixed in 10% formalin and embedded in paraffin. Tissue sections were stained using anti-STEAP-1 polyclonal antibodies directed towards the N-terminal peptide. Samples include: (a) LNCaP cells probed in the presence of N-terminal STEAP-1 peptide 1, (b) LNCaP plus non specific peptide 2, (c) normal prostate tissue, (d) grade 3 prostate carcinoma, (e) grade 4 prostate carcinoma, (f) LAPC-9 AD xenograft, (g) normal bladder, (h) normal colon. All images are at 400× magnification.

FIG. 9. Partial nucleotide and deduced amino acid sequences of STEAP-2 (98P4B6) clone GTA3 cDNA (SEQ ID NOs: 7 and 8, respectively). The 5' end sequence of this clone contains an ORF of 173 amino acids.

FIG. 10. Nucleotide sequences of additional STEAP family members identified by searching the dbest database with the protein sequence of STEAP-1. In addition to STEAP-1, another three STEAP family members are indicated with their GenBank accession numbers. One of these corresponds to the gene 98P4B6 that was identified by SSH. AA5058880/ SEQ ID NO: 9; 98P4B6/SEQ ID NO: 10; AI139607/SEQ ID NO: 11; R80991/SEQ ID NO: 12.

FIG. 11. Primary structural comparison of STEAP family proteins. FIG. 11A. Amino acid sequence-alignment of STEAP-1 (8P1D4 CLONE 10; SEQ ID NO:2) and STEAP-2 (98P4B6; SEQ ID NO:8) sequences. The alignment was performed using the SIM alignment program of the Baylor College of Medicine Search Launcher Web site. Results show a 61.4% identity in a 171 amino acid overlap; Score: 576.0; Gap frequency: 0.0%. FIG. 11B. Amino acid sequence alignment of STEAP-1 with partial ORF sequences of STEAP-2 and two other putative family member proteins (SEQ ID NO:33 and SEQ ID NO:34) using the PIMA program; transmembrane domains identified by the SOSUI program are in bold.

Figure 12:
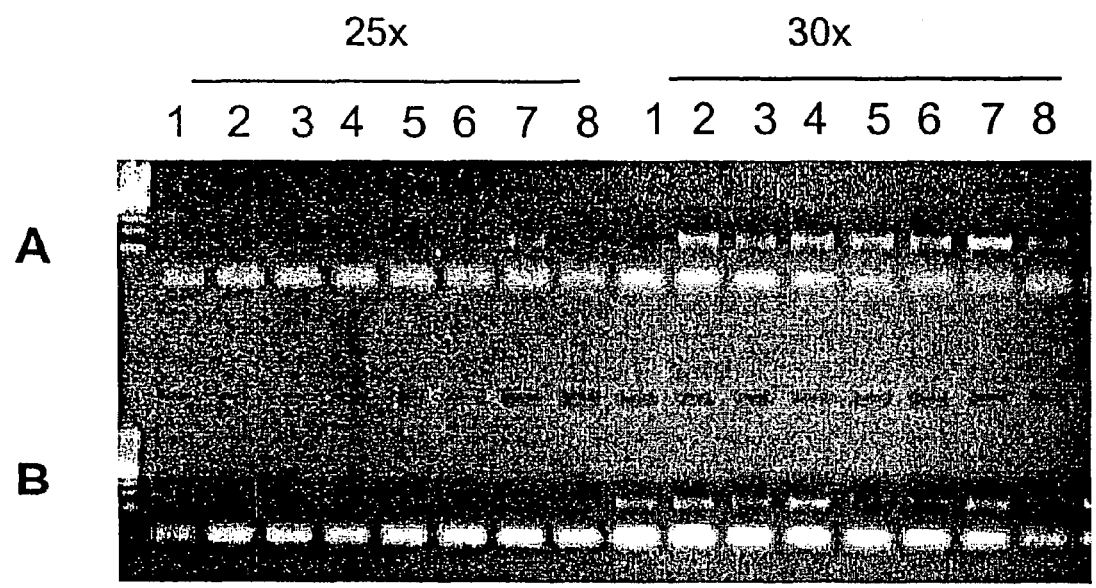

FIG. 12. Predominant expression of AI139607 in placenta and prostate. First strand cDNA was prepared from 16 normal tissues. Normalization was performed by PCR using primers to actin and GAPDH. Semi-quantitative PCR, using primers to AI139607, shows predominant expression of AI139607 in placenta and prostate after 25 cycles of amplification. The following primers were used to amplify AI139607:

```
AI139607.1
5' TTAGGACAACTTGATCACCAGCA 3'      (SEQ ID NO: 13)

AI139607.2
5' TGTCCAGTCCAAACTGGGTTATTT 3'     (SEQ ID NO: 14)
```

Figure 13:
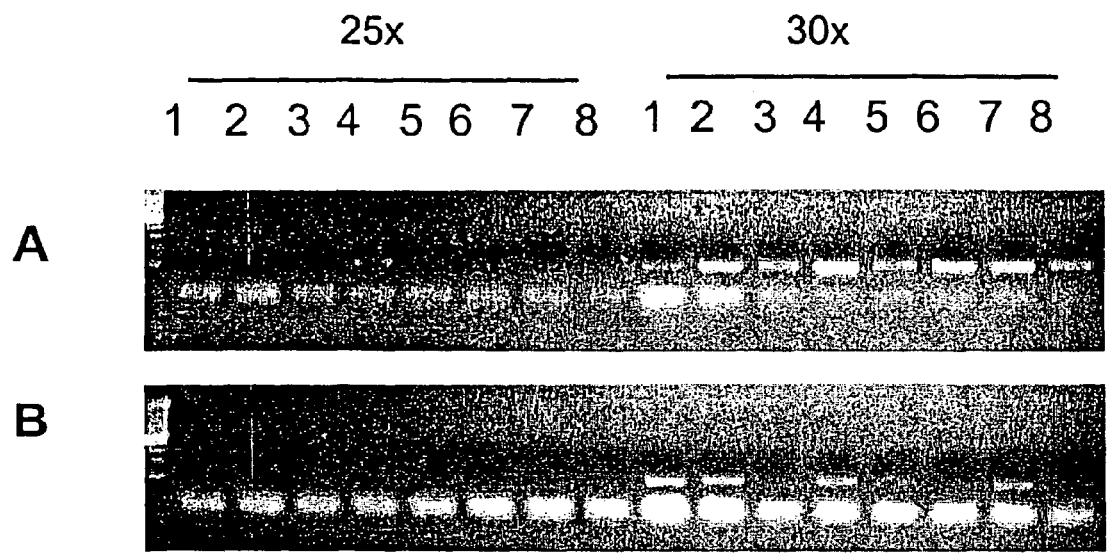

FIG. 13. Predominant expression of R80991 in liver. First strand cDNA was prepared from 16 normal tissues. Normalization was performed by PCR using primers to actin and GAPDH. Semi-quantitative PCR, using primers to R80991, shows predominant expression of R80991 in liver after 25 cycles of amplification. The following primers were used to amplify R80991:

```
R80991.1
5' AGGGAGTTCAGCTTCGTTCAGTC 3'      (SEQ ID NO: 15)

R80991.2
5' GGTAGAACTTGTAGCGGCTCTCCT 3'     (SEQ ID NO: 16)
```

Figure 14:
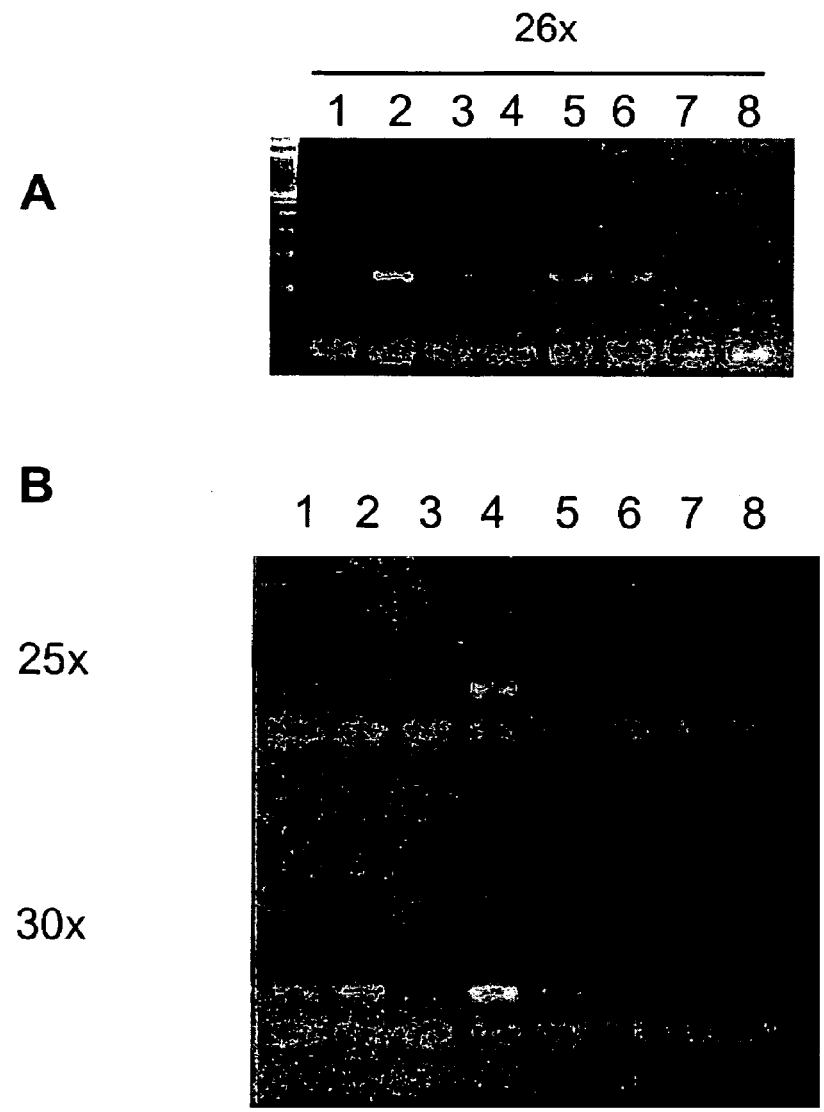

FIG. 14. Predominant expression of STEAP-2 (98P4B6) in prostate tissue. First strand cDNA was prepared from 8 normal tissues, the LAPC xenografts (4AD, 4AI and 9AD) and HeLa cells. Normalization was performed by PCR using primers to actin and GAPDH. Semi-quantitative PCR, using primers to 98P4B6, shows predominant expression of 98P4B6 in normal prostate and the LAPC xenografts. The following primers were used to amplify STEAP II:

```
98P4B6.1
5' GACTGAGCTGGAACTGGAATTTGT 3'    (SEQ ID NO: 17)

98P4B6.2
5' TTTGAGGAGACTTCATCTCACTGG 3'    (SEQ ID NO: 18)
```

FIG. 15. Lower expression of the prostate-specific STEAP-2/98P4B6 gene in prostate cancer xenografts determined by Northern blot analysis. Human normal tissue filters (A and B) were obtained from CLONTECH and contain 2 µg of mRNA per lane. Xenograft filter (C) was prepared with 10 µg of total RNA per lane. The blots were analyzed using the SSH derived 98P4B6 clone as probe. All RNA samples were normalized by ethidium bromide staining.

Figure 16:
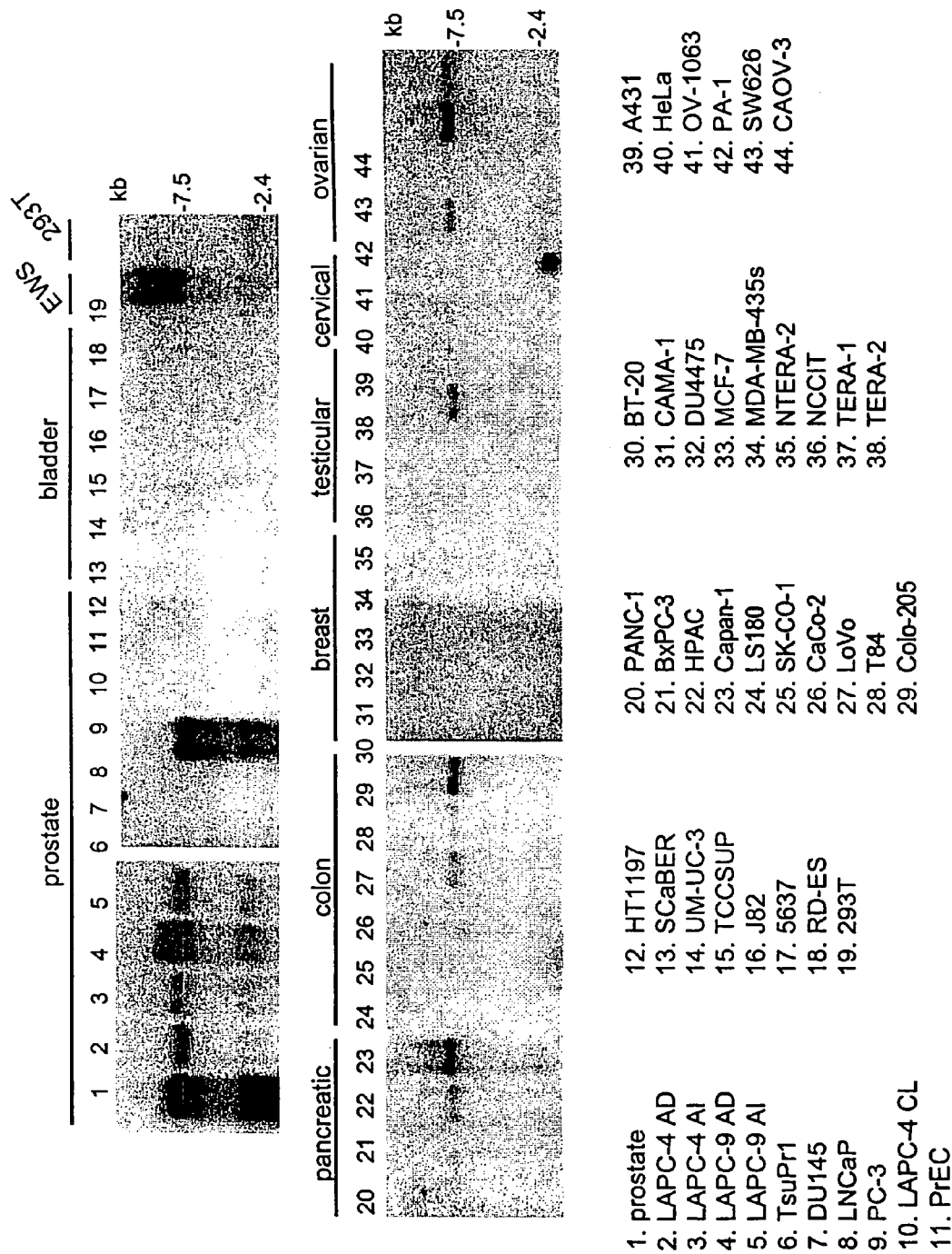

FIG. 16. Expression of STEAP-2 in prostate and select cancer cell lines as determined by Northern blot analysis. Xenograft and cell line filters were prepared with 10 µg total RNA per lane. The blots were analyzed using an SSH derived 98P4B6 clone as probe. All RNA samples were normalized by ethidium bromide staining.

Figure 17:
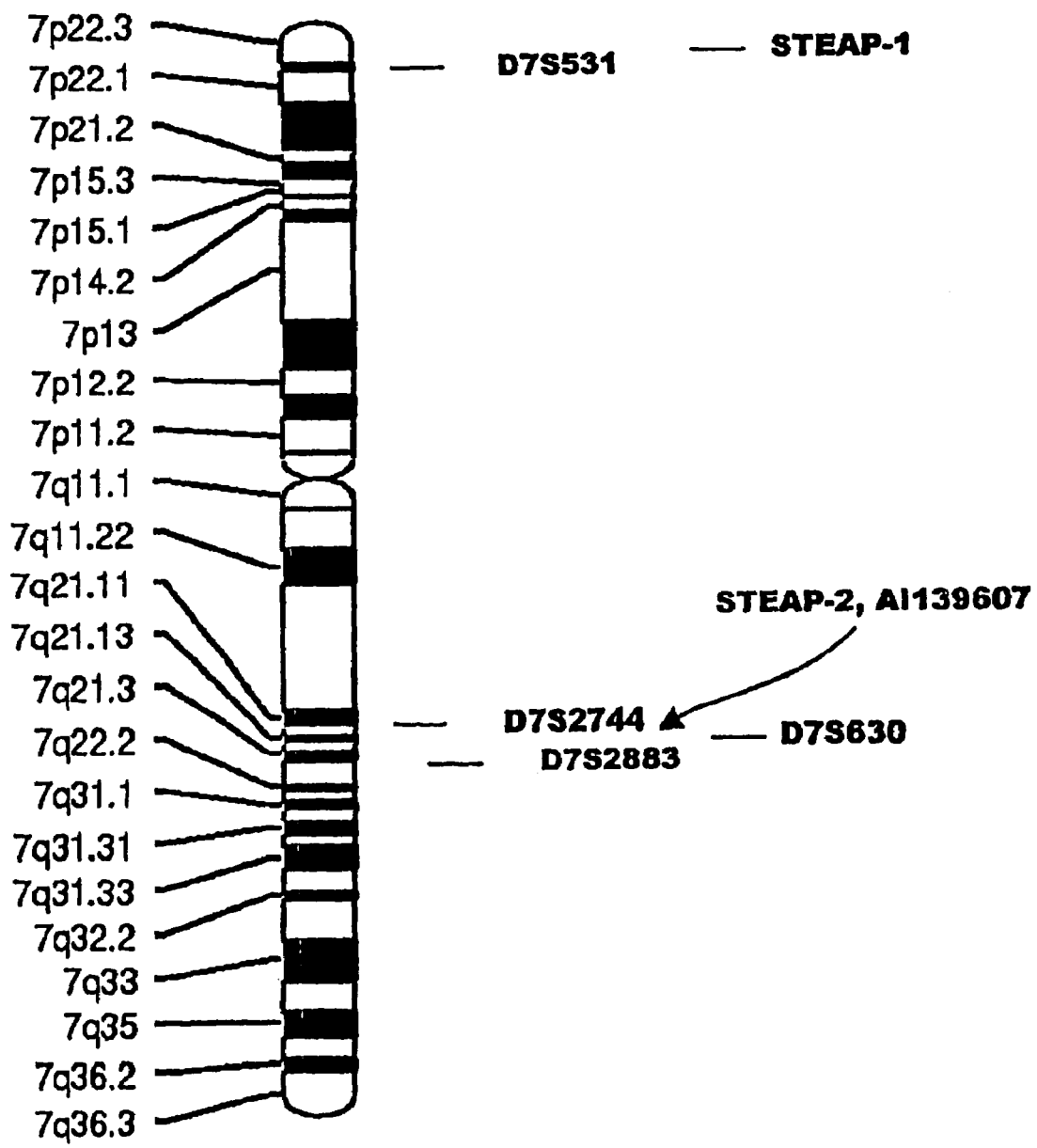

FIG. 17. Chromosomal localization of STEAP family members. The chromosomal localizations of the STEAP genes described herein were determined using the GeneBridge4 radiation hybrid panel (Research Genetics, Huntsville Ala.). The mapping for STEAP-2 and AI139607 was performed using the Stanford G3 radiation hybrid panel (Research Genetics, Huntsville Ala.).

Figure 18:

FIG. 18. Schematic representation of Intron-Exon boundaries within the ORF of human STEAP-1 gene. A total of 3 introns (i) and 4 exons (e) were identified.

Figure 19:
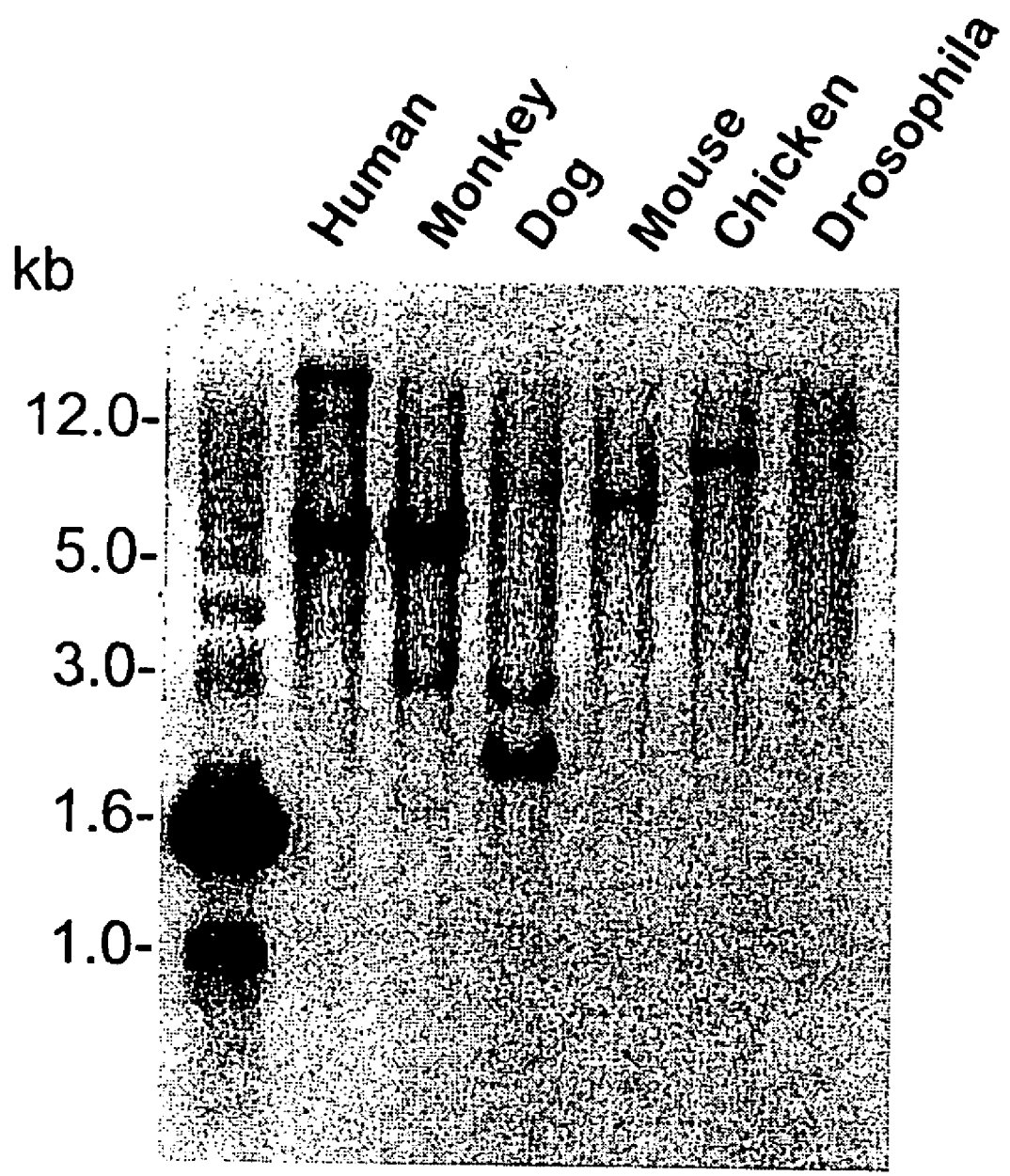

FIG. 19. Zooblot southern analysis of STEAP-1 gene in various species. Genomic DNA was prepared from several different organisms including human, monkey, dog, mouse, chicken and *Drosophila*. Ten micrograms of each DNA sample was digested with EcoRI, blotted onto nitrocellulose and probed with a STEAP-1 probe. Size standards are indicated on the side in kilobases (kb).

Figure 20:
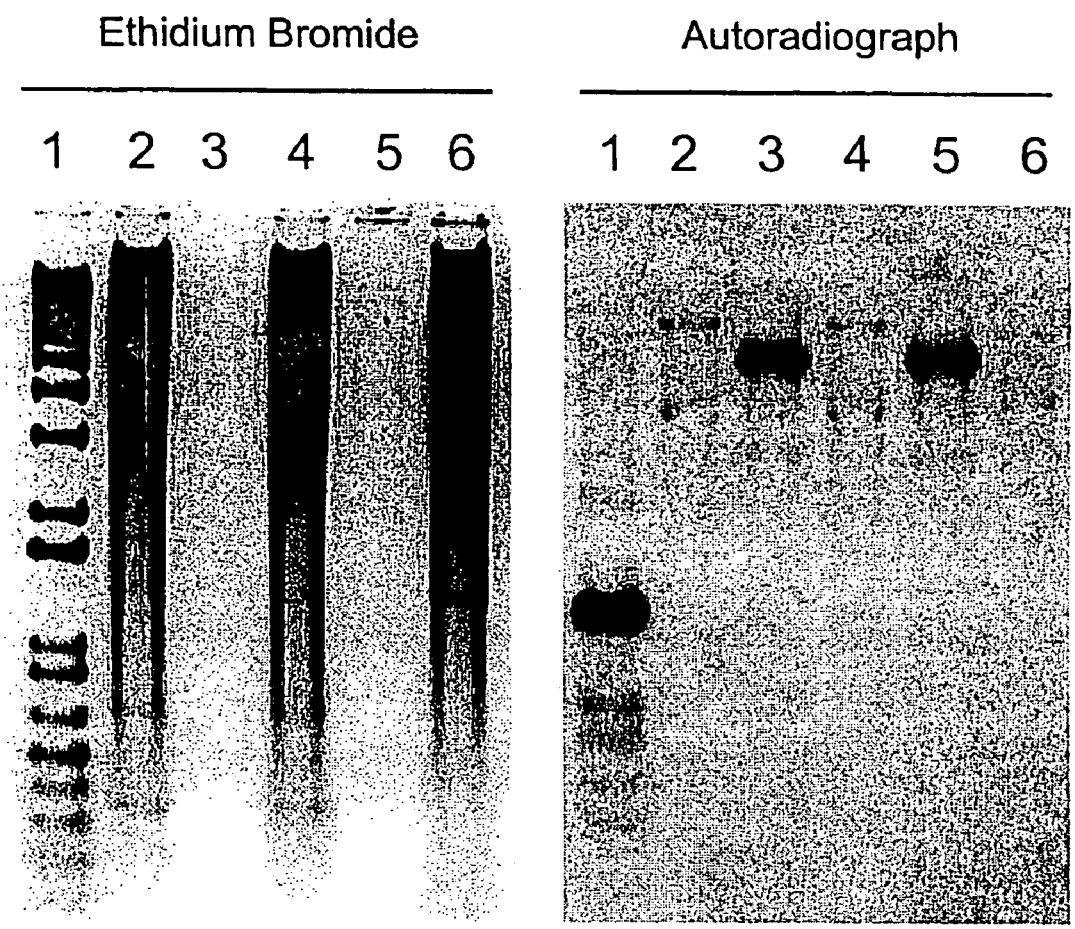

FIG. 20. Southern blot analysis of mouse BAC with a STEAP-1 probe. DNA was prepared from human cells to isolate genomic DNA and from a mouse BAC clone (12P11) that contains the mouse STEAP gene. Each DNA sample was digested with EcoRI, blotted onto nitrocellulose and probed. Eight micrograms of genomic DNA was compared to 250 ng of mouse BAC DNA.

DETAILED DESCRIPTION OF THE INVENTION

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used-herein, the terms "advanced prostate cancer", "locally advanced prostate cancer", "advanced disease" and "locally advanced disease" mean prostate cancers which have extended through the-prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

As used herein, the terms "metastatic prostate cancer" and "metastatic disease" mean prostate cancers which have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is the preferred treatment modality. Patients with metastatic prostate cancer eventually develop an androgen-refractory state within 12 to 18 months of treatment initiation, and approximately half of these patients die within 6 months thereafter. The most common site for prostate cancer metastasis is bone. Prostate cancer bone metastases are, on balance, characteristically osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA.

As used herein, the term "polypeptide" means a polymer of at least 10 amino acids. Throughout the specification, standard three letter or single letter designations for amino acids are used.

As used herein, the terms "hybridize", "hybridizing", "hybridizes" and the like, used in the context of polynucleotides, are meant to refer to conventional hybridization conditions, preferably such as hybridization in 50% formamide/6×SSC/0.1% SDS/100 µg/ml ssDNA, in which temperatures for hybridization are above 37 degrees C. and temperatures for washing in 0.1×SSC/0.1% SDS are above 55 degrees C., and most preferably to stringent hybridization conditions.

In the context of amino acid sequence comparisons, the term "identity" is used to express the percentage of amino acid residues at the same relative position which are the same. Also in this context, the term "homology" is used to express the percentage of amino acid residues at the same relative positions which are either identical or are similar, using the conserved amino acid criteria of BLAST analysis, as is generally understood in the art. Further details regarding amino acid substitutions, which are considered conservative under such criteria, are provided below.

Additional definitions are provided throughout the subsections which follow.

Molecular and Biochemical Features of the STEAPs

The invention relates to a novel family of proteins, termed STEAPs. Four STEAPs are specifically described herein by way of structural, molecular and biochemical features. As is further described in the Examples which follow, the STEAPs have been characterized in a variety of ways. For example, analyses of nucleotide coding and amino acid sequences were conducted in order to identify conserved structural elements within the STEAP family. Extensive RT-PCR and Northern blot analyses of STEAP mRNA expression were conducted in order to establish the range of normal and cancerous tissues expressing the various STEAP messages. Western blot, immunohistochemical and flow cytometric analyses of STEAP protein expression were conducted to determine protein expression profiles, cell surface localization and gross molecular topology of STEAP.

Figure 1B:
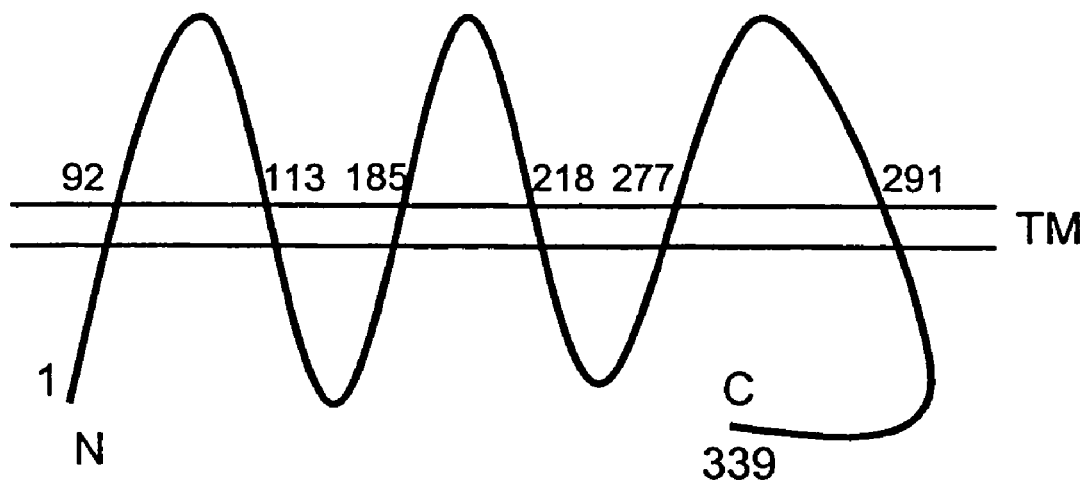
FIG. 1. STEAP-1 structure. 1A-1-1A-2: Nucleotide and deduced amino acid sequences of STEAP-1 (8P1B4) clone 10 cDNA (SEQ ID NOs. 1 and 2, respectively). The start Methionine is indicated in bold at amino acid residue position 1 and six putative transmembrane domains are indicated in bold and are underlined. 1B: Schematic representation of STEAP-1 transmembrane orientation; amino acid residues bordering the predicted extracellular domains are indicated and correspond to the numbering scheme of FIG. 1A. 1C: G/C rich 5' non-coding sequence of the STEAP-1 gene (SEQ ID NO: 3) as determined by overlapping sequences of clone 10 and clone 3.

The prototype member of the STEAP family, STEAP-1, is a six-transmembrane cell surface protein of 339 amino acids with no identifiable homology to any known human protein. The cDNA nucleotide and deduced amino acid sequences of human STEAP-1 are shown in FIG. 1A. A gross topological schematic of the STEAP-1 protein integrated within the cell membrane is shown in FIG. 1B. STEAP-1 expression is predominantly prostate-specific in normal tissues. Specifically, extensive analysis of STEAP-1 mRNA and protein expression in normal human tissues shows that STEAP-1 protein is predominantly expressed in prostate and, to a far smaller degree, in bladder. STEAP-1 mRNA is also relatively prostate specific, with only very low level expression detected in a few other normal tissues. In cancer, STEAP-1 mRNA and protein is consistently expressed at high levels in prostate cancer and during all stages of the disease. STEAP-1 is also expressed in other cancers. Specifically, STEAP-1 mRNA is expressed at very high levels in bladder, colon, pancreatic, and ovarian cancer (as well as other cancers). In addition, cell surface expression of STEAP-1 protein has been established in prostate, bladder and colon cancers. Therefore, STEAP-1 has all of the hallmark characteristics of an excellent therapeutic target for the treatment of certain cancers, including particularly prostate, colon and bladder carcinomas.

STEAP-2 is a highly homologous transmembrane protein encoded by a distinct gene. The STEAP-1 and STEAP-2 sequences show a high degree of structural conservation, particularly throughout their predicted transmembrane domains. The partial cDNA nucleotide and deduced amino acid sequences of STEAP-2 are shown in FIG. 9. Both the STEAP-1 and STEAP-2 genes are located on chromosome 7, but on different arms. STEAP-2 exhibits a markedly different mRNA and protein expression profile relative to STEAP-1, suggesting that these two STEAP family members may be differentially regulated. STEAP-2 appears to be very prostate-specific, as significant mRNA expression is not detected in a variety of normal tissues. In prostate cancer, STEAP-2 also-appears to follow a different course relative to STEAP-1, since STEAP-2 expression is down-regulated in at least some prostate cancers. In addition, STEAP-2 expression in other non-prostate cancers tested seems generally absent, although high level expression of STEAP-2 (like STEAP-1) is detected in Ewing sarcoma.

STEAP-3 and STEAP 4 appear to be closely related to both STEAP-1 and STEAP-2 on a structural level, and both appear to be transmembrane proteins as well. STEAP-3 and STEAP 4 show unique expression profiles. STEAP-3, for example, appears to have an expression pattern which is predominantly restricted to placenta and, to a smaller degree, expression is seen in prostate but not in other normal tissues tested. STEAP-4 seems to be expressed predominantly in liver. Neither STEAP-3 nor STEAP-4 appear to be expressed in prostate cancer xenografts which exhibit high level STEAP-1 and STEAP-2 expression.

Three of the four STEAPs described herein map to human chromosome 7 (STEAP-1, -2 and 3). Interestingly, STEAP-1 maps within 7p22 (7p22.3), a large region of allelic gain reported for both primary and recurrent prostate cancers (Visakorpi et al., 1995 Cancer Res. 55: 342, Nupponen et al., 1998 Am. J. Pathol. 153: 141), suggesting that up-regulation of STEAP-1 in cancer might include genomic mechanisms.

The function of the STEAPs are not known. Other cell surface molecules that contain six transmembrane domains include ion channels (Dolly and Parcej, 1996 J Bioenerg. Biomembr. 28:231) and water channels or aquaporins (Reizer et al., 1993 Crit. Rev. Biochem. Mol. Biol. 28:235). Structural studies show that both types of molecules assemble into tetrameric complexes to form functional channels (Christie; 1995, Clin. Exp. Pharmacol. Physiol. 22:944, Walz et al., 1997 Nature 387:624, Cheng et al., 1997 Nature 387:627). Immunohistochemical staining of STEAP-1 in the prostate gland seems to be concentrated at the cell-cell boundaries, with less staining detected at the luminal side. This may suggest a role for STEAP-1 in tight-junctions, gap-junctions or cell adhesion. In order to test these possibilities, xenopus oocytes (or other cells) expressing STEAP may being analyzed using voltage-clamp and patch-clamp experiments to determine if STEAP functions as an ion-channel. Oocyte cell volume may also be measured to determine if STEAP exhibits water channel properties. If STEAPs function as channel or gap-junction proteins, they may serve as excellent targets for inhibition using, for example, antibodies, small molecules, and polynucleotides capable of inhibiting expression or function. The restricted expression pattern in normal tissue, and the high levels of expression in cancer tissue suggest that interfering with STEAP function may selectively kill cancer cells.

Since the STEAP gene family is predominantly expressed in epithelial tissue, it seems possible that the STEAP proteins function as ion channels or gap-junction proteins in epithelial cell function. Ion channels have been implicated in proliferation and invasiveness of prostate cancer cells (Lalani et al., 1997, Cancer Metastasis Rev. 16:29). Both rat and human prostate cancer cells contain sub-population of cells with higher and lower expression levels of sodium channels. Higher levels of sodium channel expression correlate with more aggressive invasiveness in vitro (Smith et al., 1998, FEBS Lett. 423:19). Similarly, it has been shown that a specific blockade of sodium channels inhibits the invasiveness of PC-3 cells in vitro (Laniado et al., 1997, Am. J. Pathol. 150: 1213), while specific inhibition of potassium channels in LNCaP cells inhibited cell proliferation (Skryma et al., 1997, Prostate 33:112). These reports suggest a role for ion channels in prostate cancer and also demonstrate that small molecules that inhibit ion channel function may interfere with prostate cancer proliferation.

STEAP Polynucleotides

One aspect of the invention provides polynucleotides corresponding or complementary to all or part of a STEAP gene, mRNA, and/or coding sequence, preferably in isolated form, including polynucleotides encoding a STEAP protein and fragments thereof, DNA, RNA, DNA/RNA hybrid, and related molecules, polynucleotides or oligonucleotides complementary to a STEAP gene or mRNA sequence or a part thereof, and polynucleotides or oligonucleotides which hybridize to a STEAP gene, mRNA, or to a STEAP-encoding polynucleotide (collectively, "STEAP polynucleotides"). As used herein, STEAP genes and proteins are meant to include the STEAP-1 and STEAP-2 genes and proteins, the genes and proteins corresponding to GeneBank Accession numbers AI139607 and R80991 (STEAP-3 and STEAP-4, respectively), and the genes and proteins corresponding to other STEAP proteins and structurally similar variants of the foregoing. Such other STEAP proteins and variants will generally have coding sequences which are highly homologous to the STEAP-1 and/or STEAP-2 coding sequences, and preferably will share at least about 50% amino acid identity and at least about 60% amino acid homology (using BLAST criteria), more preferably sharing 70% or greater homology (using BLAST criteria).

The STEAP family member gene sequences described herein encode STEAP proteins sharing unique highly conserved amino acid sequence domains which distinguish them from other proteins. Proteins which include one or more of these unique highly conserved domains may be related to the STEAP family members or may represent new STEAP proteins. Referring to FIG. 11A, which is an amino acid sequence alignment of the full STEAP-1 and partial STEAP-2 protein sequences, the STEAP-1 and STEAP-2 sequences share 61% identity and 79% homology, with particularly close sequence conservation in the predicted transmembrane domains. Referring to FIG. 11B, which is an amino acid alignment of the available structures of the four STEAP family members, very close conservation is apparent in the overlapping regions, particularly in the fourth-and fifth transmembrane domains and the predicted intracellular loop between them. Amino acid sequence comparisons show that (1) STEAP-2 and STEAP-3 are 50% identical and 69% homologous in their overlapping sequences; (2) STEAP-2 and STEAP-4 are 56% identical and 87% homologous in their overlapping sequences; (3) STEAP-3 and STEAP-1 are 37% identical and 63% homologous in their overlapping sequences; (4) STEAP-3 and STEAP-4 are 38% identical and 57% homologous in their overlapping sequences; and (5) STEAP-4 and STEAP-1 are 42% identical and 65% homologous in their overlapping sequences.

A STEAP polynucleotide may comprise a polynucleotide having the nucleotide sequence of human STEAP-1 as shown in FIG. 1A (SEQ ID NO. 1) or the nucleotide sequence of human STEAP-2 as shown in FIG. 9 (SEQ ID NO: 7), a sequence complementary to either of the foregoing, or a polynucleotide fragment of any of the foregoing. Another embodiment comprises a polynucelotide which encodes the human STEAP-1 protein amino acid sequence as shown in FIG. 1A (SEQ ID NO. 2) or which encodes the human STEAP-2 protein amino acid sequence as shown in FIG. 9 (SEQ ID NO: 8), a sequence complementary to either of the foregoing, or a polynucleotide fragment of any of the foregoing. Another embodiment comprises a polynucleotide which is capable of hybridizing under stringent hybridization conditions to the human STEAP-1 cDNA shown in FIG. 1A (SEQ ID NO. 1) or to a polynucleotide fragment thereof. Another embodiment comprises a polynucleotide which is capable of hybridizing under stringent hybridization conditions to the human STEAP-2 cDNA shown in FIG. 9 (SEQ D NO.7) or to a polynucleotide fragment thereof.

Specifically contemplated are genomic DNA, cDNAs, ribozymes, and antisense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the STEAP polynucleotides and polynucleotide sequences disclosed herein.

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of a STEAP polynucleotide in a sample and as a means for detecting a cell expressing a STEAP protein. Examples of such probes include polypeptides comprising all or part of the human STEAP-1 cDNA sequence shown in FIG. 1A (SEQ ID NO. 1) and polypeptides comprising all or part of the human STEAP-2 cDNA sequence shown in FIG. 1A (SEQ ID NO. 7). Examples of primer pairs capable of specifically amplifying STEAP mRNAs are also described in the Examples which follow. As will be understood by the skilled artisan, a great many different primers and probes may be prepared based on the sequences provided in herein and used effectively to amplify and/or detect a STEAP mRNA or an mRNA encoding a particular STEAP family member (e.g., STEAP-1).

As used herein, a polynucleotide is said to be "isolated" when it is substantially separated from contaminant polynucleotides which correspond or are complementary to genes other than the STEAP gene or which encode polypeptides other than STEAP gene product or fragments thereof. A skilled artisan can readily employ nucleic acid isolation procedures to obtain an isolated STEAP polynucleotide.

The STEAP polynucleotides of the invention are useful for a variety of purposes, including but not limited to their use as probes and primers for the amplification and/or detection of the STEAP gene(s), mRNA(s), or fragments thereof; as reagents for the diagnosis and/or prognosis of prostate cancer and other cancers; as coding sequences capable of directing the expression of STEAP polypeptides; as tools for modulating or inhibiting the expression of the STEAP gene(s) and/or translation of the STEAP transcript(s); and as therapeutic agents.

Methods for Isolating STEAP-Encoding Nucleic Acid Molecules

The STEAP cDNA sequences described herein enable the isolation of other polynucleotides encoding STEAP gene product(s), as well as the isolation of polynucleotides encoding STEAP gene product homologues, alternatively spliced isoforms, allelic variants, and mutant forms of the STEAP gene product. Various molecular cloning methods that can be employed to isolate full length cDNAs encoding a STEAP gene are well known (See, for example, Sambrook, J. et al., Molecular Cloning: A Laboratory Manual, 2d edition., Cold Spring Harbor Press, N.Y., 1989; Current Protocols in Molecular Biology. Ausubel et al., Eds., Wiley and Sons, 1995). For example, lambda phage cloning methodologies may be conveniently employed, using commercially available cloning systems (e.g., Lambda ZAP Express, Stratagene). Phage clones containing STEAP gene cDNAs may be identified by probing with a labeled STEAP cDNA or a fragment thereof. For example, in one embodiment, the STEAP-1 cDNA (FIG. 1A) or a portion thereof can be synthesized and used as a probe to retrieve overlapping and full length cDNAs corresponding to a STEAP gene. Similarly, the STEAP-2 cDNA sequence may be employed. A STEAP gene may be isolated by screening genomic DNA libraries, bacterial artificial chromosome libraries (BACs), yeast artificial chromosome libraries (YACs), and the like, with STEAP DNA probes or primers.

Recombinant DNA Molecules and Host-Vector Systems

The invention also provides recombinant DNA or RNA molecules containing a STEAP polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, for example, Sambrook et al., 1989, supra).

The invention further provides a host-vector system comprising a recombinant DNA molecule containing a STEAP polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 cell). Examples of suitable mammalian cells include various prostate cancer cell lines such LnCaP, PC-3, DU145, LAPC-4, TsuPr1, other transfectable or transducible prostate cancer cell lines, as well as a number of mammalian cells routinely used for the expression of recombinant proteins (e.g., COS, CHO, 293, 293T cells). More particularly, a polynucleotide comprising the coding sequence of a STEAP may be used to generate STEAP proteins or fragments thereof using any number of host-vector systems routinely used and widely known in the art.

A wide range of host-vector systems suitable for the expression of STEAP proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, Mol. Cell. Biol. 11:1785). Using these expression vectors, STEAP may be preferably expressed in several prostate cancer and non-prostate cell lines, including for example 293, 293T, rat-1, 3T3, PC-3, LNCaP and TsuPr1. The host-vector systems of the invention are useful for the production of a STEAP protein or fragment thereof. Such host-vector systems may be employed to study the functional properties of STEAP and STEAP mutations.

Proteins encoded by the STEAP genes, or by fragments thereof, will have a variety of uses, including but not limited to generating antibodies and in methods for identifying ligands and other agents and cellular constituents that bind to a STEAP gene product. Antibodies raised against a STEAP protein or fragment thereof may be useful in diagnostic and prognostic assays, imaging methodologies (including, particularly, cancer imaging), and therapeutic methods in the management of human cancers characterized by expression of a STEAP protein, such as prostate, colon, breast, cervical and bladder carcinomas, ovarian cancers, testicular cancers and pancreatic cancers. Various immunological assays useful for the detection of STEAP proteins are contemplated, including but not limited to various types of radioimmunoassays, enzyme-linked immunosorbent assays (ELISA), enzyme-linked immunofluorescent assays (ELIFA), immunocytochemical methods, and the like. Such antibodies may be labeled and used as immunological imaging reagents capable of detecting prostate cells (e.g., in radioscintigraphic imaging methods). STEAP proteins may also be particularly useful in generating cancer vaccines, ss further described below.

STEAP Proteins

Another aspect of the present invention provides various STEAP proteins and polypeptide fragments thereof. As used herein, a STEAP protein refers to a protein that has or includes the amino acid sequence of human STEAP-1 as provided in FIG. 1A (SEQ ID NO. 2), human STEAP-2 as provided in FIG. 9 (SEQ ID NO. 8), the amino acid sequence of other mammalian STEAP homologues and variants, as well as allelic variants and conservative substitution mutants of these proteins that have STEAP biological activity.

The STEAP proteins of the invention include those specifically identified herein, as well as allelic variants, conservative substitution variants and homologs that can be isolated/generated and characterized without undue experimentation following the methods outlined below. Fusion proteins which combine parts of different STEAP proteins or fragments thereof, as well as fusion proteins of a STEAP protein and a heterologous polypeptide are also included. Such STEAP proteins will be collectively referred to as the STEAP proteins, the proteins of the invention, or STEAP. As used herein, the term "STEAP polypeptide" refers to a polypeptide fragment or a STEAP protein of at least 10 amino acids, preferably at least 15 amino acids.

A specific embodiment of a STEAP protein comprises a polypeptide having the amino acid sequence of human STEAP-1 as shown in FIG. 1A (SEQ ID NO. 2). Another embodiment of a STEAP protein comprises a polypeptide containing the partial STEAP-2 amino acid sequence as shown in FIG. 9 (SEQ ID NO. 8). Another embodiment comprises a polypeptide containing the partial STEAP-3 amino acid sequence of shown in FIG. 11B. Yet another embodiment comprises a polypeptide containing the partial STEAP-4 amino acid sequence of shown in FIG. 11B.

In general, naturally occurring allelic variants of human STEAP will share a high degree of structural identity and homology (e.g., 90% or more identity). Typically, allelic variants of the STEAP proteins will contain conservative amino acid substitutions within the STEAP sequences described herein or will contain a substitution of an amino acid from a corresponding position in a STEAP homologue. One class of STEAP allelic variants will be proteins that share a high degree of homology with at least a small region of a particular STEAP amino acid sequence, but will further contain a radical departure form the sequence, such as a non-conservative substitution, truncation, insertion or frame shift. Such alleles represent mutant STEAP proteins that typically do not perform the same biological functions or do not have all of the biological characteristics.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

STEAP proteins may be embodied in many forms, preferably in isolated form. As used herein, a protein is said to be "isolated" when physical, mechanical or chemical methods are employed to remove the STEAP protein from cellular constituents that are normally associated with the protein. A skilled artisan can readily employ standard purification methods to obtain an isolated STEAP protein. A purified STEAP protein molecule will be substantially free of other proteins or molecules which impair the binding of STEAP to antibody or other ligand. The nature and degree of isolation and purification will depend on the intended use. Embodiments of a STEAP protein include a purified STEAP protein and a functional, soluble STEAP protein. In one form, such functional, soluble STEAP proteins or fragments thereof retain the ability to bind antibody or other ligand.

The invention also provides STEAP polypeptides comprising biologically active fragments of the STEAP amino acid sequence, such as a polypeptide corresponding to part of the amino acid sequences for STEAP-1 as shown in FIG. 1A (SEQ ID NO: 2), STEAP-2 as shown in FIG. 9 (SEQ ID NO: 8), or STEAP-3 (SEQ ID NO:33), or STEAP-4 (SEQ ID NO:34), as shown in FIG. 11B. Such polypeptides of the invention exhibit properties of a STEAP protein, such as the ability to elicit the generation of antibodies which specifically bind an epitope associated with a STEAP protein. Polypeptides comprising amino acid sequences which are unique to a particular STEAP protein (relative to other STEAP proteins) may be used to generate antibodies which will specifically react with that particular STEAP protein. For example, referring to the amino acid alignment of the STEAP-1 and STEAP-2 structures shown in FIG. 11A, the skilled artisan will readily appreciate that each molecule contains stretches of sequence unique to its structure. These unique stretches can be used to generate STEAP-1 or STEAP-2 specific antibodies.

STEAP polypeptides can be generated using standard peptide synthesis technology or using chemical cleavage methods well known in the art based on the amino acid sequences of the human STEAP proteins disclosed herein. Alternatively, recombinant methods can be used to generate nucleic acid molecules that encode a polypeptide fragment of a STEAP protein. In this regard, the STEAP-encoding nucleic acid molecules described herein provide means for generating defined fragments of STEAP proteins. STEAP polypeptides are particularly useful in generating and characterizing domain specific antibodies (e.g., antibodies recognizing an extracellular or intracellular epitope of a STEAP protein), in generating STEAP family member specific antibodies (e.g., anti-STEAP-1, anti-STEAP 2 antibodies), identifying agents or cellular factors that bind to a particular STEAP or STEAP domain, and in various therapeutic contexts, including but not limited to cancer vaccines. STEAP polypeptides containing particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments containing such structures are particularly useful in generating subunit specific anti-STEAP antibodies or in identifying cellular factors that bind to STEAP.

STEAP Antibodies

Another aspect of the invention provides antibodies that bind to STEAP proteins and polypeptides. The most preferred antibodies will selectively bind to a STEAP protein and will not bind (or will bind weakly) to non-STEAP proteins and polypeptides. Anti-STEAP antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule which binds to its target, i.e., the antigen binding region.

For some applications, it may be desirable to generate antibodies which specifically react with a particular STEAP protein and/or an epitope within a particular structural domain. For example, preferred antibodies useful for cancer therapy and diagnostic imaging purposes are those which react with an epitope in an extracellular region of the STEAP protein as expressed in cancer cells. Such antibodies may be generated by using the STEAP proteins described herein, or using peptides derived from predicted extracellular domains thereof, as an immunogen. In this regard, with reference to the STEAP-1 protein topological schematic shown in FIG. 1B, regions in the extracellular loops between the indicated transmembrane domains may be selected as used to design appropriate immunogens for raising extracellular-specific antibodies.

STEAP antibodies of the invention may be particularly useful in prostate cancer therapeutic strategies, diagnostic and prognostic assays, and imaging methodologies. The invention provides various immunological assays useful for the detection and quantification of STEAP and mutant STEAP proteins and polypeptides. Such assays generally comprise one or more STEAP antibodies capable of recognizing and binding a STEAP or mutant STEAP protein, as appropriate, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting prostate cancer are also provided by the invention, including but limited to radioscintigraphic imaging methods using labeled STEAP antibodies. Such assays may be clinically useful in the detection, monitoring, and prognosis of prostate cancer, particularly advanced prostate cancer.

STEAP antibodies may also be used in methods for purifying STEAP and mutant STEAP proteins and polypeptides and for isolating STEAP homologues and related molecules. For example, in one embodiment, the method of purifying a STEAP protein comprises incubating a STEAP antibody, which has been coupled to a solid matrix, with a lysate or other solution containing STEAP under conditions which permit the STEAP antibody to bind to STEAP; washing the solid matrix to eliminate impurities; and eluting the STEAP from the coupled antibody. Other uses of the STEAP antibodies of the invention include generating anti-idiotypic antibodies that mimic the STEAP protein.

STEAP antibodies may also be used therapeutically by, for example, modulating or inhibiting the biological activity of a STEAP protein or targeting and destroying prostate cancer cells expressing a STEAP protein. Antibody therapy of prostate and other cancers is more specifically described in a separate subsection below.

Various methods for the preparation of antibodies are well known in the art. For example, antibodies may be prepared by immunizing a suitable mammalian host using a STEAP protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of STEAP may also be used, such as a STEAP GST-fusion protein. In a particular embodiment, a GST fusion protein comprising all or most of the open reading frame amino acid sequence of FIG. 1A may be produced and used as an immunogen to generate appropriate antibodies. Cells expressing or overexpressing STEAP may also be used for immunizations. Similarly, any cell engineered to express STEAP may be used. Such strategies may result in the production of monoclonal antibodies with enhanced capacities for recognizing endogenous STEAP. Another useful immunogen comprises STEAP proteins linked to the plasma membrane of sheep red blood cells.

The amino acid sequence of STEAP as shown in FIG. 1A (SEQ ID NO. 2) may be used to select specific regions of the STEAP protein for generating antibodies. For example, hydrophobicity and hydrophilicity analyses of the STEAP amino acid sequence may be used to identify hydrophilic regions in the STEAP structure. Regions of the STEAP protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. For the generation of antibodies which specifically recognize a mutant STEAP protein, amino acid sequences unique to the mutant (relative to wild type STEAP) are preferable.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a STEAP immunogen is conducted generally by injection over a suitable time period and with use of a suitable adjuvant, as is generally understood in the art. During the immunization schedule, titers of antibodies can be taken to determine adequacy of antibody formation.

STEAP monoclonal antibodies are preferred and may be produced by various means well known in the art. For example, immortalized cell lines which secrete a desired monoclonal antibody may be prepared using the standard method of Kohler and Milstein or modifications which effect immortalization of lymphocytes or spleen cells, as is generally known. The immortalized cell lines secreting the desired antibodies are screened by immunoassay in which the antigen is the STEAP protein or STEAP fragment. When the appropriate immortalized cell culture secreting the desired antibody is identified, the cells may be expanded and antibodies produced either from in vitro cultures or from ascites fluid.

As mentioned above, numerous STEAP polypeptides may be used as immunogens for generating monoclonal antibodies using traditional methods. A particular embodiment comprises an antibody which immunohistochemically stains 293T cells transfected with an expression plasmid carrying the STEAP-1 coding sequence, the transfected cells expressing STEAP-1 protein, but does immunohistochemically stain untransfected 293T cells. An assay for characterizing such antibodies is provided in Example 5 herein.

In another embodiment, STEAP-1 monoclonal antibodies may be generated using NIH 3T3 cells expressing STEAP-1 as an immunogen to generate mAbs that recognize the cell surface epitopes of STEAP-1. Reactive mAbs may be screened by cell-based ELISAs using PC-3 cells over-expressing STEAP-1. In another specific embodiment, 3 peptides representing the extracellular regions of the STEAP-1 protein (specifically, REVIHPLATSHQQYFYKIPILV (SEQ ID NO: 19), RRSYRYKLLNWAYQQVQQNKEDAWIEH-DVWRMEI (SEQ ID NO: 20) and WIDIKQFVWYTPPTF (SEQ ID NO: 21) are coupled to sheep red blood cells for immunization. In another specific embodiment, recombinant STEAP-1 protein generated with an amino-terminal His-tag using a suitable expression system (e.g., baculovirus expression system pBlueBac4.5, Invitrogen) is purified using a Nickel column and used as immunogen.

The antibodies or fragments may also be produced, using current technology, by recombinant means. Regions that bind specifically to the desired regions of the STEAP protein can also be produced in the context of chimeric or CDR grafted antibodies of multiple species origin. Humanized or human STEAP antibodies may also be produced and are preferred for use in therapeutic contexts. Various approaches for producing such humanized antibodies are known, and include chimeric and CDR grafting methods; methods for producing fully human monoclonal antibodies include phage display and transgenic methods (for review, see Vaughan et al., 1998, Nature Biotechnology 16: 535-539).

Fully human STEAP monoclonal antibodies may be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45-64 (1993); Burton and Barbas, Human Antibodies from combinatorial libraries. Id., pp 65-82). Fully human STEAP monoclonal antibodies may also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607-614). This method avoids the in vitro manipulation required with phage display technology and efficiently produces high affinity authentic human antibodies.

Reactivity of STEAP antibodies with a STEAP protein may be established by a number of well known means, including Western blot, immunoprecipitation, ELISA, and FACS analyses using, as appropriate, STEAP proteins, peptides, STEAP-expressing cells or extracts thereof.

A STEAP antibody or fragment thereof of the invention may be labeled with a detectable marker or conjugated to a second molecule, such as a cytotoxic agent, and used for targeting the second molecule to a STEAP positive cell (Vitetta, E. S. et al., 1993, Immunotoxin therapy, in DeVita, Jr., V. T. et al., eds, Cancer: Principles and Practice of Oncology, 4th ed., J. B. Lippincott Co., Philadelphia, 2624-2636). Suitable detectable markers include, but are not limited to, a radioisotope, a fluorescent compound, a bioluminescent compound, chemiluminescent compound, a metal chelator or an enzyme.

Methods for the Detection of STEAP

Another aspect of the present invention relates to methods for detecting STEAP polynucleotides and STEAP proteins, as well as methods for identifying a cell which expresses STEAP.

More particularly, the invention provides assays for the detection of STEAP polynucleotides in a biological sample, such as serum, bone, prostate, and other tissues, urine, semen, cell preparations, and the like. Detectable STEAP polynucleotides include, for example, a STEAP gene or fragments thereof, STEAP mRNA, alternative splice variant STEAP mRNAs, and recombinant DNA or RNA molecules containing a STEAP polynucleotide. A number of methods for amplifying and/or detecting the presence of STEAP polynucleotides are well known in the art and may be employed in the practice of this aspect of the invention.

In one embodiment, a method for detecting a STEAP mRNA in a biological sample comprises producing cDNA from the sample by reverse transcription using at least one primer; amplifying the cDNA so produced using a STEAP polynucleotides as sense and antisense primers to amplify STEAP cDNAs therein; and detecting the presence of the amplified STEAP cDNA. In another embodiment, a method of detecting a STEAP gene in a biological sample comprises first isolating genomic DNA from the sample; amplifying the isolated genomic DNA using STEAP polynucleotides as sense and antisense primers to amplify the STEAP gene therein; and detecting the presence of the amplified STEAP gene. Any number of appropriate sense and antisense probe combinations may be designed from the nucleotide sequences provided for STEAP-1 (FIG. 1A; SEQ ID NO. 1), STEAP-2 (FIG. 9; SEQ ID NO. 7), STEAP-3 (FIG. 10; SEQ ID NO. 11), or STEAP-4 (FIG. 10; SEQ ID NO. 12), as appropriate, and used for this purpose.

The invention also provides assays for detecting the presence of a STEAP protein in a tissue of other biological sample such as serum, bone, prostate, and other tissues, urine, cell preparations, and the like. Methods for detecting a STEAP protein are also well known and include, for example, immunoprecipitation, immunohistochemical analysis, Western Blot analysis, molecular binding assays, ELISA, ELIFA and the like.

For example, in one embodiment, a method of detecting the presence of a STEAP protein in a biological sample comprises first contacting the sample with a STEAP antibody, a STEAP-reactive fragment thereof, or a recombinant protein containing an antigen binding region of a STEAP antibody; and then detecting the binding of STEAP protein in the sample thereto.

Methods for identifying a cell which expresses STEAP are also provided. In one embodiment, an assay for identifying a cell which expresses a STEAP gene comprises detecting the presence of STEAP mRNA in the cell. Methods for the detection of particular mRNAs in cells are well known and include, for example, hybridization assays using complementary DNA probes (such as in situ hybridization using labeled STEAP riboprobes, Northern blot and related techniques) and various nucleic acid amplification assays (such as RT-PCR using complementary primers specific for STEAP, and other amplification type detection methods, such as, for example, branched DNA, SISBA, TMA and the like). Alternatively, an assay for identifying a cell which expresses a STEAP gene comprises detecting the presence of STEAP protein in the cell or secreted by the cell. Various methods for the detection of proteins are well known in the art and may be employed for the detection of STEAP proteins and STEAP expressing cells.

STEAP expression analysis may also be useful as a tool for identifying and evaluating agents which modulate STEAP gene expression. For example, STEAP-1 expression is significantly upregulated in colon, bladder, pancreatic, ovarian and other cancers. Identification of a molecule or biological agent that could inhibit STEAP-1 over-expression may be of therapeutic value in the treatment of cancer. Such an agent may be identified by using a screen that quantifies STEAP expression by RT-PCR, nucleic acid hybridization or antibody binding.

Assays for Determining STEAP Expression Status

Determining the status of STEAP expression patterns in an individual may be used to diagnose cancer and may provide prognostic information useful in defining appropriate therapeutic options. Similarly, the expression status of STEAP may provide information useful for predicting susceptibility to particular disease stages, progression, and/or tumor aggressiveness. The invention provides methods and assays for determining STEAP expression status and diagnosing cancers which express STEAP.

In one aspect, the invention provides assays useful in determining the presence of cancer in an individual, comprising detecting a significant increase in STEAP mRNA or protein expression in a test cell or tissue sample relative to expression levels in the corresponding normal cell or tissue. In one embodiment, the presence of STEAP-1 mRNA is evaluated in tissue samples of the colon, pancreas, bladder, ovary, cervix, testis or breast. The presence of significant STEAP-1 expression in any of these tissues may be useful to indicate the emergence, presence and/or severity of these cancers, since the corresponding normal tissues do not express STEAP-1 mRNA. In a related embodiment, STEAP-1 expression status may be determined at the protein level rather than at the nucleic acid level. For example, such a method or assay would comprise determining the level of STEAP-1 protein expressed by cells in a test tissue sample and comparing the level so determined to the level of STEAP expressed in a corresponding normal sample. In one embodiment, the presence of STEAP-1 protein is evaluated, for example, using immunohistochemical methods. STEAP antibodies or binding partners capable of detecting STEAP protein expression may be used in a variety of assay formats well known in the art for this purpose.

Peripheral blood may be conveniently assayed for the presence of cancer cells, including prostate, colon, pancreatic, bladder and ovarian cancers, using RT-PCR to detect STEAP-1 expression. The presence of RT-PCR amplifiable STEAP-1 mRNA provides an indication of the presence of one of these types of cancer. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25: 373-384; Ghossein et al., 1995, J. Clin. Oncol. 13: 1195-2000; Heston et al., 1995, Clin. Chem. 41: 1687-1688). RT-PCR assays are well known in the art.

In another approach, a recently described sensitive assay for detecting and characterizing carcinoma cells in blood may be used (Racila et al., 1998, Proc. Natl. Acad. Sci. USA 95: 4589-4594). This assay combines immunomagnetic enrichment with multiparameter flow cytometric and immunohistochemical analyses, and is highly sensitive for the detection of cancer cells in blood, reportedly capable of detecting one epithelial cell in 1 ml of peripheral blood.

A related aspect of the invention is directed to predicting susceptibility to developing cancer in an individual. In one embodiment, a method for predicting susceptibility to cancer comprises detecting STEAP mRNA or STEAP protein in a tissue sample, its presence indicating susceptibility to cancer, wherein the degree of STEAP mRNA expression present is proportional to the degree of susceptibility.

Yet another related aspect of the invention is directed to methods for gauging tumor aggressiveness. In one embodiment, a method for gauging aggressiveness of a tumor comprises determining the level of STEAP mRNA or STEAP protein expressed by cells in a sample of the tumor, comparing the level so determined to the level of STEAP mRNA or STEAP protein expressed in a corresponding normal tissue taken from the same individual or a normal tissue reference sample, wherein the degree of STEAP mRNA or STEAP protein expression in the tumor sample relative to the normal sample indicates the degree of aggressiveness.

Methods for detecting and quantifying the expression of STEAP mRNA or protein are described herein and use standard nucleic acid and protein detection and quantification technologies well known in the art. Standard methods for the detection and quantification of STEAP mRNA include in situ hybridization using labeled STEAP riboprobes, Northern blot and related techniques using STEAP polynucleotide probes, RT-PCR analysis using primers specific for STEAP, and other amplification type detection methods, such as, for example, branched DNA, SISBA, TMA and the like. In a specific embodiment, semi-quantitative RT-PCR may be used to detect and quantify STEAP mRNA expression as described in-the Examples which follow. Any number of primers capable of amplifying STEAP may be used for this purpose, including but not limited to the various primer sets specifically described herein. Standard methods for the detection and quantification of protein may be used for this purpose. In a specific embodiment, polyclonal or monoclonal antibodies specifically reactive with the wild-type STEAP protein may be used in an immunohistochemical assay of biopsied tissue.

Diagnostic Imaging of Human Cancers

The expression profiles of STEAP-1 and STEAP-2 indicate antibodies specific therefor may be particularly useful in radionuclide and other forms of diagnostic imaging of certain cancers. For example, immunohistochemical analysis of STEAP-1 protein suggests that in normal tissues STEAP-1 is predominantly restricted to prostate and bladder. The transmembrane orientation of STEAP-1 (and presumably STEAP-2) provides a target readily identifiable by antibodies specifically reactive with extracellular epitopes. This tissue restricted expression, and the localization of STEAP to the cell surface of multiple cancers makes STEAP an ideal candidate for diagnostic imaging. Accordingly, in vivo imaging techniques may be used to image human cancers expressing a STEAP protein.

For example, cell surface STEAP-1 protein is expressed at very high levels in several human cancers, particularly prostate, bladder, colon and ovarian cancers, and Ewing sarcoma. Moreover, in normal tissues, STEAP-1 protein expression is largely restricted to prostate. Thus, radiolabeled antibodies specifically reactive with extracellular epitopes of STEAP-1 may be particularly useful in in vivo imaging of solid tumors of the foregoing cancers. Such labeled anti-STEAP-1 antibodies may provide very high level sensitivities for the detection of metastasis of these cancers.

Preferably, monoclonal antibodies are used in the diagnostic imaging methods of the invention.

Cancer Immunotherapy and Cancer Vaccines

The invention provides various immunotherapeutic methods for treating prostate cancer, including antibody therapy, in vivo vaccines, and ex vivo immunotherapy methods, which utilize polynucleotides and polypeptides corresponding to STEAP and STEAP antibodies. These therapeutic applications are described further in the following subsections.

Applicants have accumulated strong and compelling evidence that STEAP-1 is strongly expressed uniformly over the surface of glandular epithelial cells within prostate and prostate cancer cells. See, for details, immunohistochemical and Western blot analyses of STEAP-1 protein expression presented in Examples 3C and 3D as well as the STEAP-1 mRNA expression profiles obtained from the Northern blot and RT-PCR generated data presented in Examples 1, 3A and 3B. In particular, immunohistochemical analysis results show that the surface of human prostate epithelial cells (normal and cancer) appear to be uniformly coated with STEAP-1. Biochemical analysis confirms the cell surface localization of STEAP-1 initially suggested by its putative 6-transmembrane primary structural elements and by the pericellular staining plainly visualized by immunohistochemical staining.

STEAP-1 is uniformly expressed at high levels over the surface of prostate glandular epithelia, an ideal situation for immunotherapeutic intervention strategies which target extracellular STEAP epitopes. Systemic administration of STEAP-immunoreactive compositions would be expected to result in extensive contact of the composition with prostate epithelial cells via binding to STEAP-1 extracellular epitopes. Moreover, given the near absence of STEAP-1 protein expression in normal human tissues, there is ample reason to expect exquisite sensitivity without toxic, non-specific and/or non-target effects caused by the binding of the immunotherapeutic composition to STEAP-1 on non-target organs and tissues.

In addition to the high level expression of STEAP-1 in prostate and prostate cancer cells, STEAP-1 appears to be substantially over-expressed in a variety of other human cancers, including bladder, colon, pancreatic and ovarian cancers. In particular, high level STEAP-1 mRNA expression is detected in all tested prostate cancer tissues and cell lines, and in most of the pancreatic, colon, and bladder cancer cell lines tested. High level expression of STEAP-1 is also observed in some ovarian cancer cell lines. Lower level expression is observed in some breast, testicular, and cervical cancer cell lines. Very high level expression is also detected in a Ewing sarcoma cell line. Applicants have shown that cell surface STEAP-1 protein is expressed in bladder and colon cancers, while there is no detectable cell surface (or intracellular) STEAP-1 protein in normal colon and low expression in normal bladder. Antibodies specifically reactive with extracellular domains of STEAP-1 may be useful to treat these cancers systemically, either as toxin or therapeutic agent conjugates or as naked antibodies capable of inhibiting cell proliferation or function.

STEAP-2 protein is also expressed in prostate cancer, and may be expressed in other cancers as well. STEAP-2 mRNA analysis by RT-PCR and Northern blot show that expression is restricted to prostate in normal tissues, is also expressed in some prostate, pancreatic, colon, testicular, ovarian and other cancers. Therefore, antibodies reactive with STEAP-2 may be useful in the treatment of prostate and other cancers. Similarly, although not yet characterized by applicants, the expression of STEAP-3 and STEAP-4 (as well as other STEAPs) may be associated with some cancers. Thus antibodies reactive with these STEAP family member proteins may also be useful therapeutically.

STEAP antibodies may be introduced into a patient such that the antibody binds to STEAP on the cancer cells and mediates the destruction of the cells and the tumor and/or inhibits the growth of the cells or the tumor. Mechanisms by which such antibodies exert a therapeutic effect may include complement-mediated cytolysis, antibody-dependent cellular cytotoxicity, modulating the physiologic function of STEAP, inhibiting ligand binding or signal transduction pathways, modulating tumor cell differentiation, altering tumor angiogenesis factor profiles, and/or by inducing apoptosis. STEAP antibodies conjugated to toxic or therapeutic agents may also be used therapeutically to deliver the toxic or therapeutic agent directly to STEAP-bearing tumor cells.

Cancer immunotherapy using anti-STEAP antibodies may follow the teachings generated from various approaches which have been successfully employed with respect to other types of cancer, including but not limited to colon cancer (Arlen et al., 1998, Crit. Rev. Immunol. 18: 133-138), multiple myeloma (Ozaki et al., 1997, Blood 90: 3179-3186; Tsunenari et al., 1997, Blood 90: 2437-2444), gastric cancer (Kasprzyk et al., 1992, Cancer Res. 52: 2771-2776), B-cell lymphoma (Funakoshi et al., 1996, J. Immunther. Emphasis Tumor Immunol. 19: 93-101), leukemia (Zhong et al., 1996, Leuk. Res. 20: 581-589), colorectal cancer (Moun et al., 1994, Cancer Res. 54: 6160-6166); Velders et al., 1995, Cancer Res. 55: 4398-4403), and breast cancer (Shepard et al., 1991, J. Clin. Immunol. 11: 117-127).

Although STEAP antibody therapy may be useful for all stages of the foregoing cancers, antibody therapy may be particularly appropriate and in advanced or metastatic cancers. Combining the antibody therapy method of the invention with a chemotherapeutic or radiation regimen may be preferred in patients who have not received chemotherapeutic treatment, whereas treatment with the antibody therapy of the invention may be indicated for patients who have received one or more chemotherapy. Additionally, antibody therapy may also enable the use of reduced dosages of concomitant chemotherapy, particularly in patients that do not tolerate the toxicity of the chemotherapeutic agent very well.

It may be desirable for non-prostate cancer patients to be evaluated for the presence and level of STEAP over-expression, preferably using immunohistochemical assessments of tumor tissue, quantitative STEAP imaging, or other techniques capable of reliably indicating the presence and degree of STEAP overexpression. Immunohistochemical analysis of tumor biopsies or surgical specimens may be preferred for this purpose. Methods for immunohistochemical analysis of tumor tissues are well known in the art.

Anti-STEAP monoclonal antibodies useful in treating prostate and other cancers include those which are capable of initiating a potent immune response against the tumor and those which are capable of direct cytotoxicity. In this regard, anti-STEAP mAbs may elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, anti-STEAP mAbs which exert a direct biological effect on tumor growth are useful in the practice of the invention. Potential mechanisms by which such directly cytotoxic mAbs may act include inhibition of cell growth, modulation of cellular differentiation, modulation of tumor angiogenesis factor profiles, and the induction of apoptosis. The mechanism by which a particular anti-STEAP mAb exerts an anti-tumor effect may be evaluated using any number of in vitro assays designed to determine ADCC, ADMMC, complement-mediated cell lysis, and so forth, as is generally known in the art.

The anti-tumor activity of a particular anti-STEAP mAb, or combination of anti-STEAP mAbs, may be evaluated in vivo using a suitable animal model. For example, xenogenic prostate cancer models wherein human prostate cancer explants or passaged xenograft tissues are introduced into immune compromised animals, such as nude or SCID mice, are appropriate in relation to prostate cancer and have been described (Klein et al., 1997, Nature Medicine 3: 402-408). For Example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy may be predicted using assays which measure inhibition of tumor formation, tumor regression or metastasis, and the like.

It should be noted that the use of murine or other non-human monoclonal antibodies, human/mouse chimeric mAbs may induce moderate to strong immune responses in some patients. In the most severe cases, such an immune response may lead to the extensive formation of immune complexes which, potentially, can cause renal failure. Accordingly, preferred monoclonal antibodies used in the practice of the therapeutic methods of the invention are those which are either fully human or humanized and which bind specifically to the target 20P1F12/MPRSS2 antigen with high affinity but exhibit low or no antigenicity in the patient.

The method of the invention contemplate the administration of single anti-STEAP mAbs as well as combinations, or "cocktails", of different mAbs. Such mAb cocktails may have certain advantages inasmuch as they contain mAbs which exploit different effector mechanisms or combine directly cytotoxic mAbs with mAbs that rely on immune effector functionality. Such mAbs in combination may exhibit synergistic therapeutic effects. In addition, the administration of anti-STEAP mAbs may be combined with other therapeutic agents, including but not limited to various chemotherapeutic agents, androgen-blockers, and immune modulators (e.g., IL-2, GM-CSF). The anti-STEAP mAbs may be administered in their "naked" or unconjugated form, or may have therapeutic agents conjugated to them.

The anti-STEAP monoclonal antibodies used in the practice of the method of the invention may be formulated into pharmaceutical compositions comprising a carrier suitable for the desired delivery method. Suitable carriers include any material which when combined with the anti-STEAP mAbs retains the anti-tumor function of the antibody and is non-reactive with the subject's immune systems. Examples include, but are not limited to, any of a number of standard pharmaceutical carriers such as sterile phosphate buffered saline solutions, bacteriostatic water, and the like.

The anti-STEAP antibody formulations may be administered via any route capable of delivering the antibodies to the tumor site. Potentially effective routes of administration include, but are not limited to, intravenous, intraperitoneal, intramuscular, intratumor, intradermal, and the like. The preferred route of administration is by intravenous injection. A preferred formulation for intravenous injection comprises the anti-STEAP mAbs in a solution of preserved bacteriostatic water, sterile unpreserved water, and/or diluted in polyvinylchloride or polyethylene bags containing 0.9% sterile Sodium Chloride for Injection, USP. The anti-STEAP mAb preparation may be lyophilized and stored as a sterile powder, preferably under vacuum, and then reconstituted in bacteriostatic water containing, for example, benzyl alcohol preservative, or in sterile water prior to injection.

Treatment will generally involve the repeated administration of the anti-STEAP antibody preparation via an acceptable route of administration such as intravenous injection (IV), typically at a dose in the range of about 0.1 to about 10 mg/kg body weight. Doses in the range of 10-500 mg mAb per week may be effective and well tolerated. Based on clinical experience with the Herceptin mAb in the treatment of metastatic breast cancer, an initial loading dose of approximately 4 mg/kg patient body weight IV followed by weekly doses of about 2 mg/kg IV of the anti-STEAP mAb preparation may represent an acceptable dosing regimen. Preferably, the initial loading dose is administered as a 90 minute or longer infusion. The periodic maintenance dose may be administered as a 30 minute or longer infusion, provided the initial dose was well tolerated. However, as one of skill in the art will understand, various factors will influence the ideal dose regimen in a particular case. Such factors may include, for example, the binding affinity and half life of the mAb or mAbs used, the degree of STEAP overexpression in the patient, the extent of circulating shed STEAP antigen, the desired steady-state antibody concentration level, frequency of treatment, and the influence of chemotherapeutic agents used in combination with the treatment method of the invention.

Optimally, patients should be evaluated for the level of circulating shed STEAP antigen in serum in order to assist in the determination of the most effective dosing regimen and related factors. Such evaluations may also be used for monitoring purposes throughout therapy, and may be useful to gauge therapeutic success in combination with evaluating other parameters (such as serum PSA levels in prostate cancer therapy).

Cancer Vaccines

The invention further provides prostate cancer vaccines comprising a STEAP protein or fragment thereof. The use of a tumor antigen in a vaccine for generating humoral and cell-mediated immunity for use in anti-cancer therapy is well known in the art and has been employed in prostate cancer using human PSMA and rodent PAP immunogens (Hodge et al., 1995, Int. J. Cancer 63:231-237; Fong et al., 1997, J. Immunol. 159: 3113-3117). Such methods can be readily practiced by employing a STEAP protein, or fragment thereof, or a STEAP-encoding nucleic acid molecule and recombinant vectors capable of expressing and appropriately presenting the STEAP immunogen.

For example, viral gene delivery systems may be used to deliver a STEAP-encoding nucleic acid molecule. Various viral gene delivery systems which can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658-663). Non-viral delivery systems may also be employed by using naked DNA encoding a STEAP protein or fragment thereof introduced into the patient (e.g., intramuscularly) to induce an anti-tumor response. In one embodiment, the full-length human STEAP cDNA may be employed. In another embodiment, STEAP nucleic acid molecules encoding specific cytotoxic T lymphocyte (CTL) epitopes may be employed. CTL epitopes can be determined using specific algorithms (e.g., Epimer, Brown University) to identify peptides within a STEAP protein which are capable of optimally binding to specified HLA alleles.

Various ex vivo strategies may also be employed. One approach involves the use of dendritic cells to present STEAP antigen to a patient's immune system. Dendritic cells express MHC class I and II, B7 costimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28: 65-69; Murphy et al., 1996, Prostate 29: 371-380). Dendritic cells can be used to present STEAP peptides to T cells in the context of MHC class I and II molecules. In one embodiment, autologous dendritic cells are pulsed with STEAP peptides capable of binding to MHC molecules. In another embodiment, dendritic cells are pulsed with the complete STEAP protein. Yet another embodiment involves engineering the overexpression of the STEAP gene in dendritic cells using various implementing vectors known in the art, such as adenovirus (Arthur et al., 1997, Cancer Gene Ther. 4: 17-25), retrovirus (Henderson et al., 1996, Cancer Res. 56: 3763-3770), lentivirus, adeno-associated virus, DNA transfection (Ribas et al., 1997, Cancer Res. 57: 2865-2869), and tumor-derived RNA transfection (Ashley et al., 1997, J. Exp. Med. 186: 1177-1182).

Anti-idiotypic anti-STEAP antibodies can also be used in anti-cancer therapy as a vaccine for inducing an immune response to cells expressing a STEAP protein. Specifically, the generation of anti-idiotypic antibodies is well known in the art and can readily be adapted to generate anti-idiotypic anti-STEAP antibodies that mimic an epitope on a STEAP protein (see, for example, Wagner et al., 1997, Hybridoma 16: 33-40; Foon et al., 1995, J. Clin. Invest. 96: 334-342; Herlyn et al., 1996, Cancer Immunol. Immunother. 43: 65-76). Such an anti-idiotypic antibody can be used in anti-idiotypic therapy as presently practiced with other anti-idiotypic antibodies directed against tumor antigens.

Genetic immunization methods may be employed to generate prophylactic or therapeutic humoral and cellular immune responses directed against cancer cells expressing STEAP. Constructs comprising DNA encoding a STEAP protein/immunogen and appropriate regulatory sequences may be injected directly into muscle or skin of an individual, such that the cells of the muscle or skin take-up the construct and express the encoded STEAP protein/immunogen. Expression of the STEAP protein immunogen results in the generation of prophylactic or therapeutic humoral and cellular immunity against prostate cancer. Various prophylactic and therapeutic genetic immunization techniques known in the art may be used (for review, see information and references published at Internet address www.genweb.com).

Kits

For use in the diagnostic and therapeutic applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe which is or can be detectably labeled. Such probe may be an antibody or polynucleotide specific for a STEAP protein or a STEAP gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radionucleotide label.

EXAMPLES

Various aspects of the invention are further described and illustrated by way of the several examples which follow, none of which are intended to limit the scope of the invention.

Example 1

Isolation of cDNA Fragment of STEAP-1 Gene

Materials and Methods

Cell Lines and Human Tissues

All human cancer cell lines used in this study were obtained from the ATCC. All cell lines were maintained in DMEM with 10% fetal calf serum. PrEC (primary prostate epithelial cells) were obtained from Clonetics and were grown in PrEBM media supplemented with growth factors (Clonetics).

All human prostate cancer xenografts were originally provided by Charles Sawyers (UCLA) (Klein et al., 1997). LAPC-4 AD and LAPC-9 AD xenografts were routinely passaged as small tissue chunks in recipient SCID males. LAPC-4 AI and LAPC-9 AI xenografts were derived as described previously (Klein et al., 1997) and were passaged in castrated males or in female SCID mice. A benign prostatic hyperplasia tissue sample was patient-derived.

Human tissues for RNA and protein analyses were obtained from the Human Tissue Resource Center, (HTRC) at the UCLA (Los Angeles, Calif.) and from QualTek, Inc. (Santa Barbara, Calif.).

RNA Isolation:

Tumor tissue and cell lines were homogenized in Trizol reagent (Life Technologies, Gibco BRL) using 10 ml/g tissue or 10 ml/108 cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.

```
RSACDN (cDNA synthesis primer):
                                      (SEQ ID NO: 22)
5'TTTTGTACAAGCTT303'

Adaptor 1:
                                      (SEQ ID NO: 23)
5'CTAATACGACTCACTATAGGGCTCGAGCGGCCGCCCGGGCAGGT3'

(SEQ ID NO: 24)
3'GGCCCGTCCA5'

Adaptor 2:
                                      (SEQ ID NO: 25)
5'GTAATACGACTCACTATAGGGCAGCGTGGTCGCGGCCGAGGT3'

(SEQ ID NO: 26)
3'CGGCTCCA5'

PCR primer 1:
                                      (SEQ ID NO: 27)
5'CTAATACGACTCACTATAGGGC3'

Nested primer (NP)1:
                                      (SEQ ID NO: 28)
5'TCGAGCGGCCGCCCGGGCAGGT3'

Nested primer (NP)2:
                                      (SEQ ID NO: 29)
5'AGCGTGGTCGCGGCCGAGGT3'
```

Suppression Subtractive Hybridization:

Suppression Subtractive Hybridization (SSH) was used to identify cDNAs corresponding to genes which may be up-regulated in androgen dependent prostate cancer compared to benign prostatic hyperplasia.

Double stranded cDNAs corresponding to the LAPC-4 AD xenograft (tester) and the BPH tissue (driver) were synthesized from 2 µg of poly(A)+ RNA isolated from xenograft and BPH tissue, as described above, using CLONTECH's PCR-Select cDNA Subtraction Kit and 1 ng of oligonucleotide RSACDN as primer. First- and second-strand synthesis were carried out as described in the Kit's user manual protocol (CLONTECH Protocol No. PT1117-1, Catalog No. K1804-1). The resulting cDNA was digested with Rsa I for 3 hrs. at 37° C. Digested cDNA was extracted with phenol/chloroform (1:1) and ethanol precipitated.

Driver cDNA (BPH) was generated by combining in a 4 to 1 ratio Rsa I digested BPH cDNA with digested cDNA from mouse liver, in order to ensure that murine genes were subtracted from the tester cDNA (LAPC-4 AD).

Tester cDNA (LAPC-4 AD) was generated by diluting 1 µl of Rsa I digested LAPC-4 AD cDNA (400 ng) in 5 µl of water. The diluted cDNA (2 µl, 160 ng) was then ligated to 2 µl of adaptor 1 and adaptor 2 (10 µM), in separate ligation reactions, in a total volume of 10 µl at 16° C. overnight, using 400 u of T4 DNA ligase (CLONTECH). Ligation was terminated with 1 µl of 0.2 M EDTA and heating at 72° C. for 5 min.

The first hybridization was performed by adding 1.5 µl (600 ng) of driver cDNA to each of two tubes containing 1.5 µl (20 ng) adaptor 1- and adaptor 2-ligated tester cDNA. In a final volume of 4 µl, the samples were overlayed with mineral oil, denatured in an MJ Research thermal cycler at 98° C. for 1.5 minutes, and then were allowed to hybridize for 8 hrs at 68° C. The two hybridizations were then mixed together with an additional 1 µl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10× reaction buffer (CLONTECH) and 0.5 μl 50× Advantage cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10-12 cycles of 94° C. for 10 sec, 68° C. for 30 sec, 72° C. for 1.5 minutes. The PCR products were analyzed using 2% agarose gel electrophoresis.

The PCR products were inserted into pCR2.1 using the T/A vector cloning kit (Invitrogen). Transformed *E. coli* were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis:

First strand cDNAs were generated from 1 μg of mRNA with oligo (dT)12-18 priming using the Gibco-BRL Superscript Preamplification system. The manufacturers protocol was used and included an incubation for 50 min at 42° C. with reverse transcriptase followed by RNAse H treatment at 37° C. for 20 min. After completing the reaction, the volume was increased to 200 μl with water prior to normalization. First strand cDNAs from 16 different normal human tissues were obtained from Clontech.

Normalization of the first strand cDNAs from multiple tissues was performed by using the primers 5'atatcgccgcgctcgtcgtcgacaa3' (SEQ ID NO: 35) and 5'agccacacgcagctcattgtagaagg3' (SEQ ID NO: 36) to amplify β-actin. First strand cDNA (5 μl) was amplified in a total volume of 50 μl containing 0.4 μM primers, 0.2 μM each dNTPs, 1×PCR buffer (Clontech, 10 mM Tris-HCL, 1.5 mM MgCl$_2$, 50 mM KCl, pH8.3) and 1× Klentaq DNA polymerase (Clontech). Five μl of the PCR reaction was removed at 18, 20, and 22 cycles and used for agarose gel electrophoresis. PCR was performed using an MJ Research thermal cycler under the following conditions: initial denaturation was at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization were required to achieve equal band intensities in all tissues after 22 cycles of PCR.

To determine expression levels of the 8P1D4 gene, 5 μl of normalized first strand cDNA was analyzed by PCR using 25, 30, and 35 cycles of amplification using the following primer pairs, which were designed with the assistance of (MIT; for details, see, www.genome.wi.mit.edu):

```
                                       (SEQ ID NO: 30)
5' ACT TTG TTG ATG ACC AGG ATT GGA 3'

(SEQ ID NO: 31)
5' CAG AAC TTC AGC ACA CAC AGG AAC 3'
```

Semi quantitative expression analysis was achieved by comparing the PCR products at cycle numbers that give light band intensities.

Results:

Several SSH experiments were conduced as described in the Materials and Methods, supra, and led to the isolation of numerous candidate gene fragment clones. All candidate clones were sequenced and subjected to homology analysis against all sequences in the major public gene and EST databases in order to provide information on the identity of the corresponding gene and to help guide the decision to analyze a particular gene for differential expression. In general, gene fragments which had no homology to any known sequence in any of the searched databases, and thus considered to represent novel genes, as well as gene fragments showing homology to previously sequenced expressed sequence tags (ESTs), were subjected to differential expression analysis by RT-PCR and/or Northern analysis.

One of the cDNA clones, designated 8P1D4, was 436 bp in length and showed homology to an EST sequence in the NCI-CGAP tumor gene database. The full length cDNA encoding the 8P1D4 gene was subsequently isolated using this cDNA and re-named STEAP-1 (Example 2, below). The 8P1D4 cDNA nucleotide sequence corresponds to nucleotide residues 150 through 585 in the STEAP-1 cDNA sequence as shown in FIG. 1A. Another clone, designated 28P3E1, 561 bp in length showed homology to a number of EST sequences in the NCI-CGAP tumor gene database or in other databases. Part of the 28P3E1 sequence (356 bp) is identical to an EST derived from human fetal tissue. After the full length STEAP-1 cDNA was obtained and sequenced, it became apparent that this clone also corresponds to STEAP-1 (more specifically, to residues 622 through the 3' end of the STEAP-1 nucleotide sequence as shown in FIG. 1A).

Differential expression analysis by RT-PCR using primers derived from the 8P1D4 cDNA clone showed that the 8P1D4 (STEAP-1) gene is expressed at approximately equal levels in normal prostate and the LAPC-4 and LAPC-9 xenografts (FIG. 2, panel A). Further RT-PCR expression analysis of first strand cDNAs from 16 normal tissues showed greatest levels of 8P1D4 expression in prostate. Substantially lower level expression in several other normal tissues (i.e., colon, ovary, small intestine, spleen and testis) was detectable only at 30 cycles of amplification in brain, pancreas, colon and small intestine (FIG. 2, panels B and C).

Example 2

Isolation of Full Length STEAP-1 Encoding cDNA

The 436 bp 8P1D4 gene fragment (Example 1) was used to isolate additional cDNAs encoding the 8P1D4/STEAP-1 gene. Briefly, a normal human prostate cDNA library (Clontech) was screened with a labeled probe generated from the 436 bp 8P1D4 cDNA. One of the positive clones, clone 10, is 1195 bp in length and encodes a 339 amino acid protein having nucleotide and encoded amino acid sequences bearing no significant homology to any known human genes or proteins (homology to a rat Kidney Injury Protein recently described in International Application WO98/53071). The encoded protein contains at least 6 predicted transmembrane motifs implying a cell surface orientation (see FIG. 1A, predicted transmembrane motifs underlined). These structural features led to the designation "STEAP", for "Six Transmembrane Epithelial Antigen of the Prostate". Subsequent identification of additional STEAP proteins led to the re-designation of the 8P1D4 gene product as "STEAP-1". The STEAP-1 cDNA and encoded amino acid sequences are shown in FIG. 1A and correspond to SEQ ID NOS: 1 and 2, respectively. STEAP-1 cDNA clone 10 has been deposited with the American Type Culture Collection ("ATCC") (Mannassas, Va.) as plasmid 8P1D4 clone 10.1 on Aug. 26, 1998 as ATCC Accession Number 98849. The STEAP-1 cDNA clone can be excised therefrom using EcoRI/XbaI double digest (EcoRI at the 5'end, XbaI at the 3'end).

This deposit was made under the provisions of the Budapest Treaty on the International Recognition of the Deposit of Microorganisms for the Purpose of Patent Procedure and the Regulations there under (Budapest Treaty). This assures maintenance of a viable culture of the deposit for 30 years from the date of deposit and for at least five (5) years after the most recent request for the furnishing of a sample of the deposit received by the depository. The deposits will be made available by ATCC under the terms of the Budapest Treaty, and subject to an agreement between Genentech, Inc. and ATCC, which assures that all restrictions imposed by the depositor on the availability to the public of the deposited material will be irrevocably removed upon the granting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. § 122 and the Commissioner's rules pursuant thereto (including 37 C.F.R. § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Example 3

STEAP-1 Gene and Protein Expression Analysis

In order to begin to characterize the biological characteristics of STEAP-1, an extensive evaluation of STEAP-1 mRNA and STEAP-1 protein expression across a variety of human tissue specimens was undertaken. This evaluation included Northern blot, Western blot and immunohistochemical analysis of STEAP-1 expression in a large number of normal human tissues, human prostate cancer xenografts and cell lines, and various other human cancer cell lines.

Example 3A

Northern Blot Analysis of STEAP-1 mRNA Expression in Normal Human Tissues

Initial analysis of STEAP-1 mRNA expression in normal human tissues was conducted by Northern blotting two multiple tissue blots obtained from Clontech (Palo Alto, Calif.), comprising a total of 16 different normal human tissues, using labeled STEAP-1 clone 10 as a probe. RNA samples were quantitatively normalized with a β-actin probe. The results are shown in FIG. 3A. The highest expression level was detected in normal prostate, with an approximately 5-10 fold lower level of expression detected in colon and liver. These northern blots showed two transcripts of approximately 1.4 kb and 4.0 kb, the former of which corresponds to the full length STEAP-1 clone 10 cDNA, which encodes the entire STEAP-1 open reading frame. The larger transcript was separately cloned as a 3627 bp cDNA from a normal prostate library, the sequence of which contains a 2399 bp intron (FIG. 4).

This initial analysis was extended by using the STEAP-1 clone 10 probe to analyze an RNA dot blot matrix of 37 normal human tissues (Clontech, Palo Alto, Calif.; Human Master Blot™). The results are shown in FIG. 3B and show strong STEAP-1 expression only in prostate. Very low level STEAP-1 RNA expression was detected in liver, lung, trachea and fetal liver tissue, at perhaps a 5-fold lower level compared to prostate. No expression was detected in any of the remaining tissues. Based on these analyses, significant STEAP-1 expression appears to be prostate specific in normal tissues.

Example 3B

Northern Blot Analysis of STEAP-1 mRNA Expression in Prostate Cancer Xenografts and Cell Lines To analyze STEAP-1 expression in human cancer tissues and cell lines, RNAs derived from human-prostate cancer xenografts and an extensive panel of prostate and non-prostate cancer cell lines were-analyzed by Northern blot using STEAP-1 cDNA clone 10 as probe. All RNA samples were quantitatively normalized by ethiduim bromide staining and subsequent analysis with a labeled β-actin probe.

The results, presented in FIG. 5, show high level STEAP-1 expression in all the LAPC xenografts and all of the prostate cancer cell lines. Expression in the LAPC-9 xenografts was higher compared to the LAPC-4 xenografts, with no significant difference observed between androgen-dependent and androgen-independent sublines (FIG. 5A). Expression in the LAPC-4 xenografts was comparable to expression in normal prostate. Lower levels of expression were detected in PrEC cells (Clonetics), which represent the basal cell compartment of the prostate. Analysis of prostate cancer cell lines showed highest expression levels in LNCaP, an androgen dependent prostate carcinoma cell line. Significant expression was also detected in the androgen-independent cell lines PC-3 and DU145. High levels of STEAP expression were also detected in LAPC-4 and LAPC-9 tumors that were grown within the tibia of mice as a model of prostate cancer bone metastasis (FIG. 5B).

Significantly, very strong STEAP-1 expression was also detected in many of the non-prostate human cancer cell lines analyzed (FIG. 5A). Particularly high level expression was observed in RD-ES cells, an Ewing sarcoma (EWS) derived cell line. Additionally, very high level expression was also detected in several of the colon cancer cell lines (e.g., CaCo-2, LoVo, T84 and Colo-205), bladder carcinoma cell lines (e.g., SCABER, UM-UC-3, TCCSUP and 5637), ovarian cancer cell lines (e.g., OV-1063 and SW 626) and pancreatic cancer cell lines (e.g., HPAC, Capan-1, PANC-1 and BxPC-3). These results, combined with the absence of strong expression in the corresponding normal tissues (FIG. 3), indicate that STEAP-1 may be generally up-regulated in these types (as well as other types) of human cancers.

Example 3C

Western Blot Analysis of STEAP-1 Protein Expression in Prostate and Other Cancers A 15 mer peptide corresponding to amino acid residues 14 through 28 of the STEAP-1 amino acid sequence as shown in FIG. 1A (WKMKPRRNLEEDDYL) (SEQ ID NO: 39) was synthesized and used to immunize sheep for the generation of sheep polyclonal antibodies towards the amino-terminus of the protein (anti-STEAP-1) as follows. The peptide was conjugated to KLH (keyhole limpet hemocyanin). The sheep was initially immunized with 400 μg of peptide in complete Freund's adjuvant. The animal was subsequently boosted every two weeks with 200 μg of peptide in incomplete Freund's adjuvant. Anti-STEAP antibody was affinity-purified from sheep serum using STEAP peptide coupled to Affi-Gel 10 (Bio-Rad). Purified antibody is stored in phosphate-buffered saline with 0.1% sodium azide.

To test antibody specificity, the cDNA of STEAP-1 was cloned into a retroviral expression vector (pSR?tkneo, Muller et al., 1991, MCB 11:1785). NIH 3T3 cells were infected with retroviruses encoding STEAP-1 and were selected in G418 for 2 weeks. Western blot analysis of protein extracts of infected and un-infected NIH 3T3 cells showed expression of a protein with an apparent molecular weight of 36 kD only in the infected cells (FIG. 6, lanes marked "3T3 STEAP" AND "3T3").

The anti-STEAP-1 polyclonal antibody was used to probe Western blots of cell lysates prepared from a variety of prostate cancer xenograft tissues, prostate cancer cell lines and other non-prostate cancer cell lines. Protein samples (20 μg each) were quantitatively normalized by probing the blots with an anti-Grb-2 antibody.

The results are shown in FIG. 6. STEAP-1 protein was detected in all of the LAPC prostate cancer xenografts, all of the prostate cancer cell lines, a primary prostate cancer specimen and its matched normal prostate control. Highest STEAP-1 protein expression was detected in the LAPC-9 xenograft and in LNCaP cells, in agreement with the Northern blot analysis described immediately above. High level expression was also observed in the bladder carcinoma cell line UM-UC-3. Expression in other cancer cell lines was also detectable (FIG. 6).

Example 3D

Immunohistochemical Analysis of STEAP-1 Protein Expression in Prostate Tumor Biopsy and Surgical Specimens To determine the extent of STEAP-1 protein expression in clinical materials, tissue sections were prepared from a variety of prostate cancer biopsies and surgical samples for immunohistochemical analysis. Tissues were fixed in 10% formalin, embedded in paraffin, and sectioned according to standard protocol. Formalin-fixed, paraffin-embedded sections of LNCaP cells were used as a positive control. Sections were stained with an anti-STEAP-1 polyclonal antibody directed against a STEAP-1 N-terminal epitope (as described immediately above). LNCaP sections were stained in the presence of an excess amount of the STEAP-1 N-terminal peptide immunogen used to generate the polyclonal antibody (peptide 1) or a non-specific peptide derived from a distinct region of the STEAP-1 protein (peptide 2; YQQVQQNKEDAWIEH (SEQ ID NO: 32))

The results are shown in FIG. 8. LNCaP cells showed uniformly strong peri-cellular staining in all cells (FIG. 8b). Excess STEAP N-terminal peptide (peptide 1) was able to competitively inhibit antibody staining (FIG. 8a), while peptide 2 had no effect (FIG. 8b). Similarly, uniformly strong peri-cellular staining was seen in the LAPC-9 (FIG. 8f) and LAPC-4 prostate cancer xenografts (data not shown). These results are clear and suggest that the staining is STEAP specific. Moreover, these results visually localize STEAP to the plasma membrane, corroborating the biochemical findings presented in Example 4 below.

The results obtained with the various clinical specimens are show in FIG. 8c (normal prostate tissue), FIG. 8d (grade 3 prostatic carcinoma), and FIG. 8e (grade 4 prostatic carcinoma), and are also-included in the summarized results shown in TABLE 1. Light to strong staining was observed in the glandular epithelia of all prostate cancer samples tested as well as in all samples derived from normal prostate or benign disease. The signal appears to be strongest at the cell membrane of the epithelial cells, especially at the cell-cell junctions (FIG. 8c, d and e) and is also inhibited with excess STEAP N-terminal peptide 1 (data not shown). Some basal cell staining is also seen in normal prostate (FIG. 8c), which is more apparent when examining atrophic glands (data not shown). STEAP-1 seems to be expressed at all stages of prostate cancer since lower grades (FIG. 8d), higher grades (FIG. 8e) and metastatic prostate cancer (represented by LAPC-9; FIG. 8f) all exhibit strong staining.

Immunohistochemical staining of a large panel of normal non-prostate tissues showed no detectable STEAP-1 expression in 24 of 27 of these normal tissues (Table 1). Only three tissue samples showed some degree of anti-STEAP-1 staining. In particular, normal bladder exhibited low levels of cell surface staining in the transitional epithelium (FIG. 8g). Pancreas and pituitary showed low levels of cytoplasmic staining (Table 1). It is unclear whether the observed cytoplasmic staining is specific or is due to non-specific binding of the antibody, since northern blotting showed little to no STEAP-1 expression in pancreas (FIG. 3). Normal colon, which exhibited higher mRNA levels than pancreas by Northern blotting (FIG. 3), exhibited no detectable staining with anti-STEAP antibodies (FIG. 8h). These results indicate that cell surface expression of STEAP-1 in normal tissues appears to be restricted to prostate and bladder.

TABLE 1

IMMUNOHISTOCHEMICAL STAINING OF HUMAN TISSUES WITH ANTI-STEAP-1 POLYCLONAL ANTIBODY

| STAINING INTENSITY | TISSUE |
|---|---|
| NONE | cerebellum, cerebral cortex, spinal cord, heart, skeletal muscle, artery, thymus, spleen, bone marrow, lymph node, lung, colon, liver, stomach, kidney, testis, ovary, fallopian tubes, placenta, uterus, breast, adrenal gland, thyroid gland, skin, bladder (3/5) |

TABLE 1-continued

IMMUNOHISTOCHEMICAL STAINING OF HUMAN TISSUES
WITH ANTI-STEAP-1 POLYCLONAL ANTIBODY

| STAINING INTENSITY | TISSUE |
|---|---|
| LIGHT TO MODERATE | bladder (2/5), pituitary gland (cytoplasmic), pancreas (cytoplasmic), BPH (3/5), prostate cancer (3/10) |
| STRONG | prostate (2/2), BPH (2/5), prostate cancer** (7/10) |

* In cases where more than one sample is analyzed per tissue, the numbers in brackets indicates how many samples correspond to the staining category/total analyzed.
**Prostate cancer grades ranged from Gleason grades 3 to 5.

Example 4

Biochemical Characterization of STEAP-1 Protein

To initially characterize the STEAP-1 protein, cDNA clone 10 (SEQ ID NO. 1) was cloned into the pcDNA 3.1 Myc-His plasmid (Invitrogen), which encodes a 6His tag at the carboxyl-terminus, transfected into 293T cells, and analyzed by flow cytometry using anti-His monoclonal antibody (His-probe, Santa Cruz) as well as the anti-STEAP-1 polyclonal antibody described above. Staining of cells was performed on intact cells as well as permeabilized cells. The results indicated that only permeabilized cells stained with both antibodies, suggesting that both termini of the STEAP-1 protein are localized intracellularly. It is therefore possible that one or more of the STEAP-1 protein termini are associated with intracellular organelles rather than the plasma membrane.

To determine whether STEAP-1 protein is expressed at the cell surface, intact STEAP-1-transfected 293T cells were labeled with a biotinylation reagent that does not enter live cells. STEAP-1 was then immunoprecipitated from cell extracts using the anti-His and anti-STEAP antibodies. SV40 large T antigen, an intracellular protein that is expressed at high levels in 293T cells, and the endogenous cell surface transferrin receptor were immunoprecipitated as negative and positive controls, respectively. After immunoprecipitation, the proteins were transferred to a membrane and visualized with horseradish peroxidase-conjugated streptavidin. The results of this analysis are shown in FIG. 7. Only the transferrin receptor (positive control) and STEAP-1 were labeled with biotin, while the SV40 large T antigen (negative control) was not detectably labeled (FIG. 7A). Since only cell surface proteins are labeled with this technique, it is clear from these results that STEAP-1 is a cell surface protein. Combined with the results obtained from the flow cytometric analysis, it is clear that STEAP-1 is a cell surface protein with intracellular amino- and carboxyl-termini.

Furthermore, the above results together with the STEAP-1 secondary structural predictions, shows that STEAP-1 is a type IIIa membrane protein with a molecular topology of six potential transmembrane domains, 3 extracellular loops, 2 intracellular loops and two intracellular termini. A schematic representation of STEAP-1 protein topology relative to the cell membrane is shown in FIG. 1B.

In addition, prostate, bladder and colon cancer cells were directly analyzed for cell surface expression of STEAP-1 by biotinylation studies. Briefly, biotinylated cell surface proteins were affinity purified with streptavidin-gel and probed with the anti-STEAP-1 polyclonal antibody described above. Western blotting of the streptavidin purified proteins clearly show cell surface biotinylation of endogenous STEAP-1 in all prostate (LNCaP, PC-3, DU145), bladder (UM-UC-3, TCCSUP) and colon cancer (LoVo, Colo) cells tested, as well as in NIH 3T3 cells infected with a STEAP-1 encoding retrovirus, but not in non-expressing NIH 3T3 cells used as a negative control (FIG. 7B). In a further negative control, STEAP-1 protein was not detected in streptavidin precipitates from non-biotinylated STEAP expressing cells (FIG. 7B).

Example 5

Identification and Structural Analysis of STEAP-2 and Other Human STEAP Family Members STEAP-1 has no homology to any known human genes. In an attempt to identify additional genes that are homologous to STEAP-1, the protein sequence of STEAP-1 was used as an electronic probe to identify family members in the public EST (expression sequence tag) database (dbest). Using the "tblastn" function in NCBI (National Center for Biotechnology Information), the dbest database was queried with the STEAP-1 protein sequence. This analysis revealed additional putative STEAP-1 homologues or STEAP family members, as further described below.

In addition, applicants cloning experiments also identified a STEAP-1 related SSH cDNA fragment, clone 98P4B6. This clone was isolated from SSH cloning using normal prostate cDNA as tester and LAPC-4 AD cDNA as driver. A larger partial sequence of the 98P4B6 clone was subsequently isolated from a normal prostate library; this clone encodes an ORF of 173 amino acids with close homology to the primary structure of STEAP-1, and thus was designated STEAP-2.

The STEAP-2 partial nucleotide and encoded ORF amino acid sequences are shown in FIG. 9. An amino acid alignment of the STEAP-1 and partial STEAP-2 primary structures is shown in FIG. 11A. STEAP-1 and -2 share 61% identity over their 171 amino acid residue overlap (FIG. 11A). Despite their homology, STEAP-1 and -2 show significantly divergent expression patterns in normal and cancerous tissues and cells, and also map to distinct locations on opposite arms of human chromosome 7 (see Examples 6 and 7 below).

Two ESTs identified by electronic probing with the STEAP-1 protein sequence, AI139607 and R80991, encode ORFs bearing close homology to the STEAP-1 and STEAP-2 sequences and thus appear to represent two additional STEAPs. Their nucleotide sequences are reproduced in FIG. 10 and their encoded ORF STEAP-like amino acid sequences are shown in FIG. 11B. The ORFs encoded by these ESTs are unique but show very clear structural relationships to both STEAP-1 and STEAP-2, particularly in the conserved transmembrane domains. Accordingly these ESTs appear to correspond to distinct STEAP family members and have thus been designated as STEAP-3 (corresponding to AI139607) and STEAP-4 (corresponding to R80991).

An amino acid alignment of the complete STEAP-1 protein sequence with the predicted partial STEAP-2, STEAP-3 and STEAP-4 amino acid sequences is shown in FIG. 11B. This alignment shows a close structural similarity between all four STEAP family proteins, particularly in the predicted transmembrane domains, even though only partial sequence information was available for three of them. The STEAP-3 and STEAP-4 proteins appear to be more closely related to STEAP-2 than to STEAP-1 or each other. Specifically, STEAP-3 shows 50% identity and 69% homology to STEAP-2, versus 37% identity and 63% homology to STEAP-1. STEAP-4 shows 56% identity and 87% homology to STEAP- 2, versus 42% identity and 65% homology to STEAP-1. STEAP-3 and STEAP-4 are 38% identical and 57% homologous to each other. These figures are estimates based upon incomplete sequence information. However, these figures suggest conservation of at least some of the transmembrane domains, suggesting common topological characteristics if not functional characteristics.

Example 6

Expression Analysis of STEAP-2 and Other Human STEAP Family Members

Example 6A

Tissue Specific Expression of STEAP Family Members in Normal Human Tissues

Expression analysis of STEAP family members in normal tissues was performed by RT-PCR. All STEAP family members appeared to exhibit tissue restricted expression patterns. AI139607 expression is detected in placenta and prostate after 25 cycles of amplification (FIG. 12). After 30 cycles, AI139607 expression is also detected in other tissues. R80991 expression is highest in normal liver, although expression is also detected in other tissues after 30 cycles of amplification (FIG. 13). Neither R80991, nor AI139607 expression was detected in the LAPC prostate cancer xenografts by RT-PCR.

RT-PCR analysis of STEAP-2 shows expression in all the LAPC prostate cancer xenografts and in normal prostate (FIG. 14, panel A). Analysis of 8 normal human tissues shows prostate-specific expression after 25 cycles of amplification (FIG. 14, panel B). Lower level expression in other tissues was detected only after 30 cycles of amplification. Northern blotting for STEAP-2 shows a pattern of 2 transcripts (approximately 3 and 8 kb in size) expressed only in prostate (and at significantly lower levels in the LAPC xenografts), with no detectable expression in any of the 15 other normal human tissues analyzed (FIG. 15, panel C). Thus, STEAP-2 expression in normal human tissues appears to be highly prostate-specific.

Example 6B

Expression of STEAP-2 in Various Cancer Cell Lines

The RT-PCR results above suggested that the different STEAP family members exhibit different tissue expression patterns. Interestingly, STEAP-2, which appears very prostate-specific, seems to be expressed at lower levels in the LAPC xenografts. This is in contrast to STEAP-1, which is highly expressed in both normal and malignant prostate tissue.

To better characterize this suggested difference in the STEAP-2 prostate cancer expression profile (relative to STEAP-1), Northern blotting was performed on RNA derived from the LAPC xenografts, as well as several prostate and other cancer cell lines, using a STEAP-2 specific probe (labeled-cDNA clone 98P4B6). The results are shown in FIG. 16 and can be summarized as follows. STEAP-2 is highly expressed in normal prostate and in some of the prostate cancer xenografts and cell lines. More particularly, very strong expression was observed in the LAPC-9 AD xenograft and the LNCaP cells. Significantly attenuated or no expression was observed in the other prostate cancer xenografts and cell lines. Very strong expression was also evident in the Ewing Sarcoma cell line RD-ES. Unlike STEAP-1, which is highly expressed in cancer cell lines derived from bladder, colon, pancreatic and ovarian tumors, STEAP-2 showed low to non-detectable expression in these same cell lines (compare with FIG. 5). Interestingly, STEAP-2 was also non-detectable in PrEC cells, which are representative of the normal basal cell compartment of the prostate. These results suggests that expression of STEAP-1 and STEAP-2 are differentially regulated. While STEAP-1 may be a gene that is generally up-regulated in cancer, STEAP-2 may be a gene that is more restricted to normal prostate and prostate cancer.

Example 7

Chromosomal Localization of STEAP Genes

The chromosomal localization of STEAP-1 was determined using the GeneBridge 4 Human/Hamster radiation hybrid (RH) panel (Walter et al., 1994, Nat. Genetics 7:22) (Research Genetics, Huntsville Ala.), while STEAP-2 and the STEAP homologues were mapped using the Stanford G3 radiation hybrid panel (Stewart et al., 1997, Genome Res. 7:422).

The following PCR primers were used for STEAP-1:

```
8P1D4.1
5' ACTTTGTTGATGACCAGGATTGGA 3'      (SEQ ID NO: 4)

8P1D4.2
5' CAGAACTTCAGCACACACAGGAAC 3'      (SEQ ID NO: 5)
```

The resulting STEAP-1 mapping vector for the 93 radiation hybrid panel DNAs (2100000201101010001000000010 111010122100011100111011010100010001000101001021 000 001111001010000), and the mapping program available at the internet address for the Whitehead Institute for Biomedical Research, localized the STEAP-1 gene to chromosome 7p22.3, telomeric to D7S531.

The following PCR primers were used for 98P4B6/STEAP-2:

```
98P4B6.1
5' GACTGAGCTGGAACTGGAATTTGT 3'      (SEQ ID NO: 17)

98P4B6.2
5' TTTGAGGAGACTTCATCTCACTGG 3'      (SEQ ID NO: 18)
```

The resulting vector (00000100100000000000000000 000000100100000000001000100000000000000100001010 1010010011), and the mapping program available at the internet address for the Stanford Human Genome Center, maps the 98P4B6 (STEAP-2) gene to chromosome 7q21.

The following PCR primers were used for AI139607:

```
AI139607.1
5' TTAGGACAACTTGATCACCAGCA 3'       (SEQ ID NO: 13)

AI139607.2
5' TGTCCAGTCCAAACTGGGTTATTT 3'      (SEQ ID NO: 14)
```

The resulting vector (000000001000000000000000001 0001000002000000010001000000010000010001000101 0000010), and the mapping program available at the internet address for the Stanford Human Genome Center, maps AI139607 to chromosome 7q21.

The following PCR primers were used for R80991:

```
R80991.3
5' ACAAGAGCCACCTCTGGGTGAA 3'      (SEQ ID NO: 37)

R80991.4
5' AGTTGAGCGAGTTTGCAATGGAC 3'     (SEQ ID NO: 38)
```

The resulting vector (00000000000200001020000000010000000000000000000001000000000100001110000000100100001), and the mapping program available at the internet address for the Stanford Human Genome Center, maps R80991 to chromosome 2q14-q21, near D2S2591.

In summary, the above results show that three of the putative human STEAP family members localize to chromosome 7, as is schematically depicted in FIG. 17. In particular, the STEAP-1 gene localizes to the far telomeric region of the short arm of chromosome 7, at 7p22.3, while STEAP-2 and AI139607 localize to the long arm of chromosome 7, at 7q21 (FIG. 17). R80991 maps to chromosome 2q14-q21.

Example 8

Identification of Intron-Exon Boundaries of STEAP-1

Genomic clones for STEAP-1 were identified by searching GenBank for BAC clones containing STEAP-1 sequences, resulting in the identification of accession numbers AC004969 (PAC DJ1121E10) and AC005053 (BAC RG041D11). Using the sequences derived from the PAC and BAC clones for STEAP the intron-exon boundaries were defined (FIG. 18). A total of 4 exons and 3 introns were identified within the coding region of the STEAP gene. Knowledge of the exact exon-intron structure of the STEAP-1 gene may be used for designing primers within intronic sequences which in turn may be used for genomic amplification of exons. Such amplification permits single-stranded conformational polymorphism (SSCP) analysis to search for polymorphisms associated with cancer. Mutant or polymorphic exons may be sequenced and compared to wild type STEAP. Such analysis may be useful to identify patients who are more susceptible to aggressive prostate cancer, as well as other types of cancer, particularly colon, bladder, pancreatic, ovarian, cervical and testicular cancers.

Southern blot analysis shows that the STEAP-1 gene exists in several species including mouse (FIG. 19). Therefore, a mouse BAC library (Mouse ES 129-V release I, Genome Systems, FRAC-4431) was screened with the human cDNA for STEAP-1 (clone 10, Example 2). One positive clone, 12P11, was identified and confirmed by southern blotting (FIG. 20). The intron-exon boundary information for human STEAP may be used to identify the mouse STEAP-1 coding sequences.

The mouse STEAP-1 genomic clone may be used to study the biological role of STEAP-1 during development and tumorigenesis. Specifically, the mouse genomic STEAP-1 clone may be inserted into a gene knock-out (K/O) vector for targeted disruption of the gene in mice, using methods generally known in the art. In addition, the role of STEAP in metabolic processes and epithelial cell function may be elucidated. Such K/O mice may be crossed with other prostate cancer mouse models, such as the TRAMP model (Greenberg et al., 1995, PNAS 92:3439), to determine whether STEAP influences the development and progression of more or less aggressive and metastatic prostate cancers.

Throughout this application, various publications are referenced within parentheses. The disclosures of these publications are hereby incorporated by reference herein in their entireties.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. A method for detecting the presence of a STEAP-1 protein in a biological sample comprising
contacting the sample with (a) a monoclonal antibody or antibody fragment that immunospecifically binds to the polypeptide shown in FIG. 1A (SEQ ID NO: 2), or (b) a recombinant protein comprising the antigen binding domain of said monoclonal antibody or antibody fragment, and
detecting the binding of STEAP-1 protein in the sample thereto.

2. A method for determining an expression level for a STEAP-1 protein encoded by SEQ ID NO:1, comprising
determining the expression level of the STEAP-1 protein in a test sample obtained from a subject having or suspected of having a cancer cell expressing the STEAP-1 protein.

3. The method of claim 2, further comprising comparing the expression level of the STEAP-1 protein in the test sample with the expression level of the STEAP-1 protein in a normal sample.

4. The method of claim 2, wherein the test sample is peripheral blood.

5. A method for determining an expression level for STEAP-1 in a test sample, comprising:
contacting a test sample obtained from a subject having or suspected of having a cancer cell expressing a STEAP-1 protein with an antibody or antibody fragment that binds specifically to the polypeptide of SEQ ID NO:2 or an extracellular domain of SEQ ID NO:2; and
quantifying an amount of STEAP-1 from the test sample bound to said antibody or antibody fragment,
whereby the expression level of STEAP-1 in the test sample is assessed.

6. The method of claim 1, wherein the sample is from a human tissue.

7. The method of claim 6, wherein the human tissue is prostate, colon, bladder, pancreas, ovary, cervix, testis, breast, bone, lymph node, lung, liver or brain.

8. The method of claim 6 wherein the binding of the antibody or antibody fragment to the STEAP-1 protein in the sample is detected using a radioscintigraphic imaging apparatus.

9. The method of claim 1, wherein the sample is blood, urine, semen, prostate, colon, bladder, pancreas, ovary, cervix, testis, breast, bone, lymph node, lung, liver, brain, serum, or a cell preparation.

10. The method of claim 1 wherein the binding of the antibody or antibody fragment to the STEAP-1 protein in the sample is detected using fluorescence-activated cell sorting (FACS) or ELISA.

11. The method of claim 1, wherein the antibody or antibody fragment is humanized.

12. The method of claim 1, wherein the antibody fragment is an Fab, F(ab')2, Fv or Sfv fragment.

13. The method of claim 1, wherein the antibody is a human antibody.

14. The method of claim 1, wherein the antibody or antibody fragment is recombinantly produced.

15. The method of claim 1, wherein the antibody or antibody fragment binds immunospecifically to an extracellular domain of STEAP-1.

16. The method of claim 1, wherein the antibody or antibody fragment is labeled with a detectable marker.

17. The method of claim 16, wherein the detectable marker is a radioisotope, a metal chelator, an enzyme, a fluorescent compound, a bioluminescent compound or a chemiluminescent compound.

18. The method of claim 17, wherein the detectable marker is a radioisotope selected from $^{212}$Bi, $^{131}$I, $^{111}$In, $^{90}$Y, $^{186}$Re, $^{211}$At, $^{125}$I, $^{188}$Re, $^{153}$Sm, $^{213}$Bi, $^{32}$P, and $^{177}$Lu.

19. The method of claim 1, wherein the sample is bone tissue.

20. The method of claim 1, wherein the sample is peripheral blood.

21. The method of claim 1, wherein the sample is prostate tissue.

22. The method of claim 2, wherein the sample is bone tissue, prostate tissue, urine, or semen.

23. The method of claim 5, wherein the antibody or antibody fragment is humanized.

24. The method of claim 5, wherein the antibody fragment is an Fab, F(ab')2, Fv or Sfv fragment.

25. The method of claim 5, wherein the antibody is a human antibody.

26. The method of claim 5, wherein the antibody or antibody fragment is recombinantly produced.

27. The method of claim 5, wherein the antibody is a monoclonal antibody.

28. The method of claim 5, wherein the antibody or antibody fragment is conjugated to a detectable marker that comprises a radioisotope, a metal chelator, an enzyme, a fluorescent compound, a bioluminescent compound or a chemiluminescent compound.

29. The method of claim 28, wherein the detectable marker is a radioisotope selected from $^{212}$Bi, $^{131}$I, $^{111}$In, $^{90}$Y, $^{186}$Re, $^{211}$At, $^{125}$I, $^{188}$Re, $^{153}$Sm, $^{213}$Bi, $^{32}$P, and $^{177}$Lu.

30. The method of claim 5, wherein the test sample is bone tissue, prostate tissue, urine, peripheral blood, or semen.

31. The method of claim 30, wherein the test sample is bone tissue.

32. The method of claim 30, wherein the test sample is peripheral blood.

33. The method of claim 30, wherein the test sample is prostate tissue.

34. The method of claim 2, wherein the test sample is prostate tissue.

35. The method of claim 2, wherein the test sample is bone tissue.

36. The method of claim 4, wherein the peripheral blood comprises prostate cancer cells.

37. The method of claim 20, wherein the peripheral blood comprises prostate cancer cells.

38. The method of claim 32, wherein the peripheral blood comprises prostate cancer cells.

39. The method of claim 5, further comprising comparing the amount of STEAP-1 bound to said antibody or antibody fragment from the test sample with the amount of STEAP-1 from a control sample.

\* \* \* \* \*

UNITED STATES PATENT AND TRADEMARK OFFICE
CERTIFICATE OF CORRECTION

| | | |
|---|---|---|
| PATENT NO. | : 7,611,904 B2 | Page 1 of 1 |
| APPLICATION NO. | : 11/580538 | |
| DATED | : November 3, 2009 | |
| INVENTOR(S) | : Daniel E. Afar et al. | |

It is certified that error appears in the above-identified patent and that said Letters Patent is hereby corrected as shown below:

Cover Page, Related U.S. Application Data, second paragraph, (60):

Please delete: "provisional application No. 60/317,840, filed on Sep. 6, 2001, provisional application No. 60/370,387, filed on Apr. 5, 2002"

Signed and Sealed this

Third Day of August, 2010

David J. Kappos
*Director of the United States Patent and Trademark Office*

SEQUENCE LISTING

```
<160> NUMBER OF SEQ ID NOS: 39

<210> SEQ ID NO 1
<211> LENGTH: 1195
<212> TYPE: DNA
<213> ORGANISM: Homo sapiens

<400> SEQUENCE: 1
ccgagactca cggtcaagct aaggcgaaga gtgggtggct gaagccatac tattttatag     60
aattaatgga aagcagaaaa gacatcacaa accaagaaga actttggaaa atgaagccta    120
ggagaaattt agaagaagac gattatttgc ataaggacac gggagagacc agcatgctaa    180
aaagacctgt gcttttgcat ttgcaccaaa cagcccatgc tgatgaattt gactgccctt    240
cagaacttca gcacacacag gaactctttc cacagtggca cttgccaatt aaaatagctg    300
ctattatagc atctctgact tttctttaca ctcttctgag ggaagtaatt caccctttag    360
caacttccca tcaacaatat ttttataaaa ttccaatcct ggtcatcaac aaagtcttgc    420
caatggtttc catcactctc ttggcattgg tttacctgcc aggtgtgata gcagcaattg    480
```

-continued

```
tccaacttca taatggaacc aagtataaga agtttccaca ttggttggat aagtggatgt      540
taacaagaaa gcagtttggg cttctcagtt tcttttttgc tgtactgcat gcaatttata      600
gtctgtctta cccaatgagg cgatcctaca gatacaagtt gctaaactgg gcatatcaac      660
aggtccaaca aaataaagaa gatgcctgga ttgagcatga tgtttggaga atggagattt      720
atgtgtctct gggaattgtg ggattggcaa tactggctct gttggctgtg acatctattc      780
catctgtgag tgactctttg acatggagag aatttcacta tattcagagc aagctaggaa      840
ttgtttccct tctactgggc acaatacacg cattgatttt tgcctggaat aagtggatag      900
atataaaaca atttgtatgg tatacacctc caacttttat gatagctgtt ttccttccaa      960
ttgttgtcct gatatttaaa agcatactat tcctgccatg cttgaggaag aagatactga     1020
agattagaca tggttgggaa gacgtcacca aaattaacaa aactgagata tgttcccagt     1080
tgtagaatta ctgtttacac acattttgt tcaatattga tatatttat caccaacatt     1140 tcaagtttgt atttgttaat aaaatgatta ttcaaggaaa aaaaaaaaa aaaaa          1195
```

<210> SEQ ID NO 2
<211> LENGTH: 339
<212> TYPE: PRT
<213> ORGANISM: Homo sapiens

<400> SEQUENCE: 2

```
Met Glu Ser Arg Lys Asp Ile Thr Asn Gln Glu Leu Trp Lys Met
  1               5                  10                  15

Lys Pro Arg Arg Asn Leu Glu Glu Asp Asp Tyr Leu His Lys Asp Thr
                 20                  25                  30

Gly Glu Thr Ser Met Leu Lys Arg Pro Val Leu Leu His Leu His Gln
             35                  40                  45

Thr Ala His Ala Asp Glu Phe Asp Cys Pro Ser Glu Leu Gln His Thr
         50                  55                  60

Gln Glu Leu Phe Pro Gln Trp His Leu Pro Ile Lys Ile Ala Ala Ile
 65                  70                  75                  80

Ile Ala Ser Leu Thr Phe Leu Tyr Thr Leu Leu Arg Glu Val Ile His
                 85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
            115                 120                 125

Val Tyr Leu Pro Gly Val Ile Ala Ala Ile Val Gln Leu His Asn Gly
            130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
            195                 200                 205

Ile Glu His Asp Val Trp Arg Met Glu Ile Tyr Val Ser Leu Gly Ile
            210                 215                 220

Val Gly Leu Ala Ile Leu Ala Leu Leu Ala Val Thr Ser Ile Pro Ser
225                 230                 235                 240
```

-continued

```
Val Ser Asp Ser Leu Thr Trp Arg Glu Phe His Tyr Ile Gln Ser Lys
            245                 250                 255
Leu Gly Ile Val Ser Leu Leu Leu Gly Thr Ile His Ala Leu Ile Phe
        260                 265                 270
Ala Trp Asn Lys Trp Ile Asp Ile Lys Gln Phe Val Trp Tyr Thr Pro
        275                 280                 285
Pro Thr Phe Met Ile Ala Val Phe Leu Pro Ile Val Leu Ile Phe
    290                 295                 300
Lys Ser Ile Leu Phe Leu Pro Cys Leu Arg Lys Lys Ile Leu Lys Ile
305                 310                 315                 320
Arg His Gly Trp Glu Asp Val Thr Lys Ile Asn Lys Thr Glu Ile Cys
                325                 330                 335
Ser Gln Leu

<210> SEQ ID NO 3
<211> LENGTH: 111
<212> TYPE: DNA
<213> ORGANISM: Homo sapiens

<400> SEQUENCE: 3
ggcggaggcg gaggcggagg gcgaggggcg gggagcgccg cctggagcgc ggcaggtcat    60
attgaacatt ccagatacct atcattactc gatgctgttg ataacagcaa g           111

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
actttgttga tgaccaggat tgga                                           24

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
cagaacttca gcacacacag gaac                                           24

<210> SEQ ID NO 6
<211> LENGTH: 3627
<212> TYPE: DNA
<213> ORGANISM: Homo sapiens

<400> SEQUENCE: 6
ggggcccgca cctctgggca gcagcggcag ccgagactca cggtcaagct aaggcgaaga    60
gtgggtggct gaagccatac tattttatag aattaatgga aagcagaaaa gacatcacaa   120
accaagaaga actttggaaa atgaagccta ggagaaattt agaagaagac gattatttgc   180
ataaggacac gggagagacc agcatgctaa aaagacctgt gcttttgcat ttgcaccaaa   240
cagcccatgc tgatgaattt gactgccctt cagaacttca gcacacacag gaactctttc   300
cacagtggca cttgccaatt aaaatagctg ctattatagc atctctgact tttctttaca   360
ctcttctgag ggaagtaatt cacccccttag caacttccca tcaacaatat ttttataaaa   420
ttccaatcct ggtcatcaac aaagtcttgc caatggtttc catcactctc ttggcattgg   480
```

-continued

| | |
|---|---|
| tttacctgcc aggtgtgata gcagcaattg tccaacttca taatggaacc aagtataaga | 540 |
| agtttccaca ttggttggat aagtggatgt taacaagaaa gcagtttggg cttctcagtt | 600 |
| tcttttttgc tgtactgcat gcaatttata gtctgtctta cccaatgagg cgatcctaca | 660 |
| gatacaagtt gctaaactgg gcatatcaac aggtccaaca aaataaagaa gatgcctgga | 720 |
| ttgagcatga tgtttggaga atggagattt atgtgtctct gggaattgtg ggattggcaa | 780 |
| tactggctct gttggctgtg acatctattc catctgtgag tgactctttg acatggagag | 840 |
| aatttcacta tattcaggta ataatatat aaaataaccc taagaggtaa atcttctttt | 900 |
| tgtgtttatg atatagaata tgttgacttt accccataaa aaataacaaa tgtttttcaa | 960 |
| cagcaaagat cttatacttg ttccaattaa taatgtgctc tcctgttgtt ttccctattg | 1020 |
| cttctaatta ggacaagtgt ttcctagaca taaataaaag gcattaaaat attctttgtt | 1080 |
| tttttttttt tgtttgtttg ttttttgttt gtttgtttgt tttttgaga tgaagtctcg | 1140 |
| ctctgttgcc catgctggag tacagtggca cgatctcggc tcactgcaac ctgcgcctcc | 1200 |
| tgggttcagg cgattctctt gcctcagcct cctgagtagc tgggattaca ggcacccatc | 1260 |
| accatgtcca gctaattttt gtatttttag tagagacagg gttttcccat gttggccagg | 1320 |
| ctggtctcga tctcctgacc tcaaatgatc cgcccacctc ggcctcccaa agtgctggga | 1380 |
| tgacagttgt gagccaccac actcagcctg ctctttctaa tatttgaaac ttgttagaca | 1440 |
| atttgctacc catctaatgt gatattttag gaatccaata tgcatggttt attatttctt | 1500 |
| aaaaaaaata ttcttttacc tgtcacctga atttagtaat gccttttatg ttacacaact | 1560 |
| tagcactttc cagaaacaaa aactctctcc ttgaaataat agagttttta tctaccaaag | 1620 |
| atatgctagt gtctcatttc aaaggctgct ttttccagct tacatttat atacttactc | 1680 |
| acttgaagtt tctaaatatt cttgtaattt taaaactatc tcagatttac tgaggtttat | 1740 |
| cttctggtgg tagattatcc ataagaagag tgatgtgcca gaatcactct gggatccttg | 1800 |
| tctgacaaga ttcaaaggac taaatttaat tcagtcatga acactgccaa ttaccgttta | 1860 |
| tgggtagaca tctttggaaa tttccacaag gtcagacatt cgcaactatc ccttctacat | 1920 |
| gtccacacgt atactccaac actttattag gcatctgatt agtttggaaa gtatgcctcc | 1980 |
| atctgaatta gtccagtgtg gcttagagtt ggtacaacat tctcacagaa tttcctaatt | 2040 |
| ttgtaggttc agcctgataa ccactggagt tctttggtcc tcattaaata gctttcttca | 2100 |
| cacattgctc tgcctgttac acatatgatg aacactgctt tttagacttc attaggaatt | 2160 |
| taggactgca tcttgacaac tgagcctatt ctactatatg tacaatacct agcccataat | 2220 |
| aggtatacaa tacacatttg gtaaaactaa ttttcaacca atgacatgta tttttcaact | 2280 |
| agtaacctag aaatgtttca cttaaaatct gagaactggt tacactacaa gttaccttgg | 2340 |
| agattcatat atgaaaacgc aaacttagct atttgattgt attcactggg acttaagaat | 2400 |
| gcgcctgaat aattgtgagt tcgatttgtt ctggcaggct aatgaccatt tccagtaaag | 2460 |
| tgaatagagg tcagaagtcg tataaaagag gtgttgtcag aacaccgttg agattacata | 2520 |
| ggtgaacaac tatttttaag caactttatt tgtgtagtga caaagcatcc caatgcaggc | 2580 |
| tgaaatgttt catcacatct ctggatctct ctattttgtg cagacattga aaaaattgtt | 2640 |
| catattattt ccatgttatc agaatatttg attttttaaa aacataggcc aagttcattc | 2700 |
| acttcattat tcatttatca aaatcagagt gaatcacatt agtcgccttc acaactgata | 2760 |
| aagatcactg aagtcaaatt gattttttgct ataatcttca atctacctat atttaattga | 2820 |

-continued

```
gaatctaaaa tgtacaaatc attgtgttga ttctgcagtg atcctgctat aagtaagact    2880
cagtccctga ttttaggtat cctgtgaaaa gcagaattaa acaaatacaa caagagacaa    2940
agcacaaaaa ataaatatca taaggggatg aacaaaatgg tggagaaaga gtagacaaag    3000 ttttgatca cctgccttca aagaaaggct gtgaattttg ttcacttaga cagcttggag     3060
acaagaaatt acccaaaagt aaggtgagga ggataggcaa aaagagcaga agatgtgaa     3120 tggacattgt tgagaaatgt gataggaaaa caatcataga taaaggattt ccaagcaaca    3180
gagcatatcc agatgaggta ggatgggata aactcttatt gaaccaatct tcaccaattt    3240 tgttttctt ttgcagagca agctaggaat tgtttccctt ctactgggca aatacacgc      3300 attgattttt gcctggaata agtggataga tataaaacaa tttgtatggt atacacctcc    3360 aactttatg atagctgttt tccttccaat tgttgtcctg atatttaaaa gcatactatt     3420
cctgccatgc ttgaggaaga agatactgaa gattagacat ggttgggaag acgtcaccaa    3480
aattaacaaa actgagatat gttcccagtt gtagaattac tgtttacaca cattttttgtt 3540 caatattgat atattttatc accaacattt caagtttgta tttgttaata aatgattat    3600 tcaaggaaaa aaaaaaaaaa aaaaaaa                                       3627

<210> SEQ ID NO 7
<211> LENGTH: 519
<212> TYPE: DNA
<213> ORGANISM: Homo sapiens

<400> SEQUENCE: 7
gacttttaca aaattcctat agagattgtg aataaaacct tacctatagt tgccattact     60
ttgctctccc tagtatacct cgcaggtctt ctggcagctg cttatcaact ttattacggc    120
accaagtata ggagatttcc accttggttg gaaacctggt tacagtgtag aaaacagctt    180
ggattactaa gttttttctt cgctatggtc catgttgcct acagcctctg cttaccgatg    240
agaaggtcag agagatattt gtttctcaac atggcttatc agcaggttca tgcaaatatt    300
gaaaactctt ggaatgagga agaagtttgg agaattgaaa tgtatatctc ctttggcata    360
atgagccttg gcttactttc cctcctggca gtcacttcta tcccttcagt gagcaatgct    420
ttaaactgga gagaattcag ttttattcag tctacacttg gatatgtcgc tctgctcata    480
agtactttcc atgttttaat ttatggatgg aaacgagct                          519

<210> SEQ ID NO 8
<211> LENGTH: 173
<212> TYPE: PRT
<213> ORGANISM: Homo sapiens

<400> SEQUENCE: 8

Asp Phe Tyr Lys Ile Pro Ile Glu Ile Val Asn Lys Thr Leu Pro Ile
  1               5                  10                  15

Val Ala Ile Thr Leu Leu Ser Leu Val Tyr Leu Ala Gly Leu Leu Ala
                 20                  25                  30

Ala Ala Tyr Gln Leu Tyr Tyr Gly Thr Lys Tyr Arg Arg Phe Pro Pro
             35                  40                  45

Trp Leu Glu Thr Trp Leu Gln Cys Arg Lys Gln Leu Gly Leu Leu Ser
         50                  55                  60

Phe Phe Phe Ala Met Val His Val Ala Tyr Ser Leu Cys Leu Pro Met
 65                  70                  75                  80

Arg Arg Ser Glu Arg Tyr Leu Phe Leu Asn Met Ala Tyr Gln Gln Val
                 85                  90                  95
```

-continued

```
His Ala Asn Ile Glu Asn Ser Trp Asn Glu Glu Val Trp Arg Ile
                100                 105                 110
Glu Met Tyr Ile Ser Phe Gly Ile Met Ser Leu Gly Leu Leu Ser Leu
        115                 120                 125
Leu Ala Val Thr Ser Ile Pro Ser Val Ser Asn Ala Leu Asn Trp Arg
    130                 135                 140
Glu Phe Ser Phe Ile Gln Ser Thr Leu Gly Tyr Val Ala Leu Leu Ile
145                 150                 155                 160
Ser Thr Phe His Val Leu Ile Tyr Gly Trp Lys Arg Ala
                165                 170
```

<210> SEQ ID NO 9
<211> LENGTH: 322
<212> TYPE: DNA
<213> ORGANISM: Homo sapiens

<400> SEQUENCE: 9

| | | |
|---|---|---|
| ggtcgacttt tcctttattc ctttgtcaga gatctgattc atccatatgc tagaaaccaa | 60 |
| cagagtgact tttacaaaat tcctatagag attgtaataa aaaccttacc tatagttgcc | 120 |
| attactttgc tctccctagt ataccttgca ggtcttctgg cagctgctta tcaactttat | 180 |
| tacggcacca agtataggag atttccacct tggttgaaaa cctggttaca gtgtagaaaa | 240 |
| cagcttggat tactaagttg tttcttcgct atggtccatg ttgcctacag cctctgctta | 300 |
| ccgatgagaa ggtcagagag at | 322 |

<210> SEQ ID NO 10
<211> LENGTH: 183
<212> TYPE: DNA
<213> ORGANISM: Homo sapiens

<400> SEQUENCE: 10

| | | |
|---|---|---|
| tttgcagctt tgcagatacc cagactgagc tggaactgga atttgtcttc ctattgactc | 60 |
| tacttcttta aaagcggctg cccattacat tcctcagctg tccttgcagt taggtgtaca | 120 |
| tgtgactgag tgttggccag tgagatgaag tctcctcaaa ggaaggcagc atgtgtcctt | 180 |
| ttt | 183 |

<210> SEQ ID NO 11
<211> LENGTH: 448
<212> TYPE: DNA
<213> ORGANISM: Homo sapiens

<400> SEQUENCE: 11

| | | |
|---|---|---|
| aagaaggaga atccatttag cacctcctca gcctggctca gtgattcata tgtggctttg | 60 |
| ggaatacttg ggtttttttct gtttgtactc ttgggaatca cttctttgcc atctgttagc | 120 |
| aatgcagtca actggagaga gttccgattt gtccagtcca actgggtta tttgaccctg | 180 |
| atcttgtgta cagcccacac cctggtgtac ggtgggaaga gattcctcag cccttcaaat | 240 |
| ctcagatggt atcttcctgc agcctacgtg ttagggctta tcattccttg cactgtgctg | 300 |
| gtgatcaagt ttgtcctaat catgccatgt gtagacaaca cccttacaag gatccgccag | 360 |
| ggctgggaaa ggaactcaaa acactagaaa aagcattgaa tggaaaatca atatttaaaa | 420 |
| caaagttcaa tttagctgga aaaaaaaa | 448 |

<210> SEQ ID NO 12
<211> LENGTH: 401
<212> TYPE: DNA
<213> ORGANISM: Homo sapiens
<220> FEATURE:
<221> NAME/KEY: misc_feature
<222> LOCATION: 11, 56, 233, 250, 310, 326, 377, 398
<223> OTHER INFORMATION: n = a,t,c or g

<400> SEQUENCE: 12

```
ggccgcggca nccgctacga cctggtcaac ctggcagtca agcaggtctt ggccanacaa    60
gagccacctc tgggtgaagg aggaggtctg gcggatggag atctacctct ccctgggagt   120
gctggccctc ggcacgttgt ccctgctggc cgtgacctca ctgccgtcca ttgcaaactc   180
gctcaactgg agggagttca gcttcgttca gtcctcactg gctttgtgg ccntcgtgct   240
gagcacactn cacacgctca cctacggctg gacccgcgcc ttcgaggaga gccgctacaa   300
gttctacctn cctcccacct tcacgntcac gctgctggtg ccctgcgttc gttcatcctg   360
ggccaaagcc ctgtttntac tgccttgcat tcagccgnag a                      401
```

<210> SEQ ID NO 13
<211> LENGTH: 23
<212> TYPE: DNA
<213> ORGANISM: Artificial Sequence
<220> FEATURE:
<223> OTHER INFORMATION: RT-PCR Primer AI139607.1

<400> SEQUENCE: 13

```
ttaggacaac ttgatcacca gca                                            23
```

<210> SEQ ID NO 14
<211> LENGTH: 24
<212> TYPE: DNA
<213> ORGANISM: Artificial Sequence
<220> FEATURE:
<223> OTHER INFORMATION: RT-PCR primer AI139607.2

<400> SEQUENCE: 14

```
tgtccagtcc aaactgggtt attt                                           24
```

<210> SEQ ID NO 15
<211> LENGTH: 23
<212> TYPE: DNA
<213> ORGANISM: Artificial Sequence
<220> FEATURE:
<223> OTHER INFORMATION: RT-PCR primer R80991.1

<400> SEQUENCE: 15

```
agggagttca gcttcgttca gtc                                            23
```

<210> SEQ ID NO 16
<211> LENGTH: 24
<212> TYPE: DNA
<213> ORGANISM: Artificial Sequence
<220> FEATURE:
<223> OTHER INFORMATION: RT-PCR primer R80991.2

<400> SEQUENCE: 16

```
ggtagaactt gtagcggctc tcct                                           24
```

<210> SEQ ID NO 17
<211> LENGTH: 24
<212> TYPE: DNA

```
<213> ORGANISM: Artificial Sequence
<220> FEATURE:
<223> OTHER INFORMATION: RT-PCR primer 98P4B6.1

<400> SEQUENCE: 17
gactgagctg gaactggaat ttgt                                              24

<210> SEQ ID NO 18
<211> LENGTH: 24
<212> TYPE: DNA
<213> ORGANISM: Artificial Sequence
<220> FEATURE:
<223> OTHER INFORMATION: RT-PCR primer 98P4B6.2

<400> SEQUENCE: 18
tttgaggaga cttcatctca ctgg                                              24

<210> SEQ ID NO 19
<211> LENGTH: 22
<212> TYPE: PRT
<213> ORGANISM: Artificial Sequence
<220> FEATURE:
<223> OTHER INFORMATION: STEAP-1 peptide

<400> SEQUENCE: 19

Arg Glu Val Ile His Pro Leu Ala Thr Ser His Gln Gln Tyr Phe Tyr
 1               5                  10                  15

Lys Ile Pro Ile Leu Val
            20

<210> SEQ ID NO 20
<211> LENGTH: 34
<212> TYPE: PRT
<213> ORGANISM: Artificial Sequence
<220> FEATURE:
<223> OTHER INFORMATION: STEAP-1 peptide

<400> SEQUENCE: 20

Arg Arg Ser Tyr Arg Tyr Lys Leu Leu Asn Trp Ala Tyr Gln Gln Val
 1               5                  10                  15

Gln Gln Asn Lys Glu Asp Ala Trp Ile Glu His Asp Val Trp Arg Met
            20                  25                  30

Glu Ile

<210> SEQ ID NO 21
<211> LENGTH: 15
<212> TYPE: PRT
<213> ORGANISM: Artificial Sequence
<220> FEATURE:
<223> OTHER INFORMATION: STEAP-1 PEPTIDE

<400> SEQUENCE: 21

Trp Ile Asp Ile Lys Gln Phe Val Trp Tyr Thr Pro Pro Thr Phe
 1               5                  10                  15

<210> SEQ ID NO 22
<211> LENGTH: 14
<212> TYPE: DNA
<213> ORGANISM: Artificial Sequence
<220> FEATURE:
<223> OTHER INFORMATION: cDNA Synthesis primer
```

```
<400> SEQUENCE: 22
ttttgtacaa gctt                                                      14

<210> SEQ ID NO 23
<211> LENGTH: 44
<212> TYPE: DNA
<213> ORGANISM: Artificial Sequence
<220> FEATURE:
<223> OTHER INFORMATION: Adaptor 1 for human STEAP-1 gene isolation

<400> SEQUENCE: 23
ctaatacgac tcactatagg gctcgagcgg ccgcccgggc aggt                     44

<210> SEQ ID NO 24
<211> LENGTH: 10
<212> TYPE: DNA
<213> ORGANISM: Artificial Sequence
<220> FEATURE:
<223> OTHER INFORMATION: Adaptor 1 for human STEAP-1 gene isolation

<400> SEQUENCE: 24
ggcccgtcca                                                           10

<210> SEQ ID NO 25
<211> LENGTH: 42
<212> TYPE: DNA
<213> ORGANISM: Artificial Sequence
<220> FEATURE:
<223> OTHER INFORMATION: Adaptor 2 for human STEAP-1 gene isolation

<400> SEQUENCE: 25
gtaatacgac tcactatagg gcagcgtggt cgcggccgag gt                       42

<210> SEQ ID NO 26
<211> LENGTH: 8
<212> TYPE: DNA
<213> ORGANISM: Artificial Sequence
<220> FEATURE:
<223> OTHER INFORMATION: Adaptor 2 for human STEAP-1 gene isolation

<400> SEQUENCE: 26 cggctcca                                                              8

<210> SEQ ID NO 27
<211> LENGTH: 22
<212> TYPE: DNA
<213> ORGANISM: Artificial Sequence
<220> FEATURE:
<223> OTHER INFORMATION: PCR primer 1

<400> SEQUENCE: 27
ctaatacgac tcactatagg gc                                             22

<210> SEQ ID NO 28
<211> LENGTH: 22
<212> TYPE: DNA
<213> ORGANISM: Artificial Sequence
<220> FEATURE:
<223> OTHER INFORMATION: Nested primer (NP) 1

<400> SEQUENCE: 28
tcgagcggcc gcccgggcag gt                                             22
```

```
<210> SEQ ID NO 29
<211> LENGTH: 20
<212> TYPE: DNA
<213> ORGANISM: Artificial Sequence
<220> FEATURE:
<223> OTHER INFORMATION: Nested primer (NP) 2

<400> SEQUENCE: 29
agcgtggtcg cggccgaggt                                              20

<210> SEQ ID NO 30
<211> LENGTH: 24
<212> TYPE: DNA
<213> ORGANISM: Artificial Sequence
<220> FEATURE:
<223> OTHER INFORMATION: RT-PCR primer 1A

<400> SEQUENCE: 30
actttgttga tgaccaggat tgga                                         24

<210> SEQ ID NO 31
<211> LENGTH: 24
<212> TYPE: DNA
<213> ORGANISM: Artificial Sequence
<220> FEATURE:
<223> OTHER INFORMATION: RT-PCR primer 1B

<400> SEQUENCE: 31
cagaacttca gcacacacag gaac                                         24

<210> SEQ ID NO 32
<211> LENGTH: 15
<212> TYPE: PRT
<213> ORGANISM: Homo sapiens

<400> SEQUENCE: 32

Tyr Gln Gln Val Gln Gln Asn Lys Glu Asp Ala Trp Ile Glu His
 1               5                  10                  15

<210> SEQ ID NO 33
<211> LENGTH: 128
<212> TYPE: PRT
<213> ORGANISM: Homo sapiens

<400> SEQUENCE: 33

Lys Lys Glu Asn Pro Phe Ser Thr Ser Ser Ala Trp Leu Ser Asp Ser
 1               5                  10                  15

Tyr Val Ala Leu Gly Ile Leu Gly Phe Phe Leu Phe Val Leu Leu Gly
                20                  25                  30

Ile Thr Ser Leu Pro Ser Val Ser Asn Ala Val Asn Trp Arg Glu Phe
            35                  40                  45

Arg Phe Val Gln Ser Lys Leu Gly Tyr Leu Thr Leu Ile Leu Cys Thr
        50                  55                  60

Ala His Thr Leu Val Tyr Gly Gly Lys Arg Phe Leu Ser Pro Ser Asn
 65                  70                  75                  80

Leu Arg Trp Tyr Leu Pro Ala Ala Tyr Val Leu Gly Leu Ile Ile Pro
                85                  90                  95

Cys Thr Val Leu Val Ile Lys Phe Val Leu Ile Met Pro Cys Val Asp
                100                 105                 110

Asn Thr Leu Thr Arg Ile Arg Gln Gly Trp Glu Arg Asn Ser Lys His
            115                 120                 125
```

```
<210> SEQ ID NO 34
<211> LENGTH: 128
<212> TYPE: PRT
<213> ORGANISM: Homo sapiens
<220> FEATURE:
<221> NAME/KEY: VARIANT
<222> LOCATION: 15, 74, 105, 122
<223> OTHER INFORMATION: Xaa = Any Amino Acid

<400> SEQUENCE: 34

Ala Thr Thr Trp Ser Thr Trp Gln Ser Ser Arg Ser Trp Pro Xaa Lys
1               5                   10                  15
Ser His Leu Trp Val Lys Glu Glu Val Trp Arg Met Glu Ile Tyr Leu
            20                  25                  30
Ser Leu Gly Val Leu Ala Leu Gly Thr Leu Ser Leu Leu Ala Val Thr
        35                  40                  45
Ser Leu Pro Ser Ile Ala Asn Ser Leu Asn Trp Arg Glu Phe Ser Phe
    50                  55                  60
Val Gln Ser Ser Leu Gly Phe Val Ala Xaa Val Leu Ser Thr Leu His
65                  70                  75                  80
Thr Leu Thr Tyr Gly Trp Thr Arg Ala Phe Glu Glu Ser Arg Tyr Lys
                85                  90                  95
Phe Tyr Leu Pro Pro Thr Phe Thr Xaa Thr Leu Leu Val Pro Cys Val
            100                 105                 110
Arg Ser Ser Trp Ala Lys Ala Leu Phe Xaa Leu Pro Cys Ile Gln Pro
        115                 120                 125

<210> SEQ ID NO 35
<211> LENGTH: 25
<212> TYPE: DNA
<213> ORGANISM: Artificial Sequence
<220> FEATURE:
<223> OTHER INFORMATION: Primer

<400> SEQUENCE: 35
atatcgccgc gctcgtcgtc gacaa                                         25

<210> SEQ ID NO 36
<211> LENGTH: 26
<212> TYPE: DNA
<213> ORGANISM: Artificial Sequence
<220> FEATURE:
<223> OTHER INFORMATION: Primer

<400> SEQUENCE: 36
agccacacgc agctcattgt agaagg                                        26

<210> SEQ ID NO 37
<211> LENGTH: 22
<212> TYPE: DNA
<213> ORGANISM: Artificial Sequence
<220> FEATURE:
<223> OTHER INFORMATION: RT-PCR primer R80991.3

<400> SEQUENCE: 37
acaagagcca cctctgggtg aa                                            22

<210> SEQ ID NO 38
<211> LENGTH: 23
<212> TYPE: DNA
<213> ORGANISM: Artificial Sequence
<220> FEATURE:
<223> OTHER INFORMATION: RT-PCR primer R80991.4
```

```
-continued

<400> SEQUENCE: 38
agttgagcga gtttgcaatg gac                                               23

<210> SEQ ID NO 39
<211> LENGTH: 15
<212> TYPE: PRT
<213> ORGANISM: Homo sapiens

<400> SEQUENCE: 39

Trp Lys Met Lys Pro Arg Arg Asn Leu Glu Glu Asp Asp Tyr Leu
1               5                   10                  15
```